United States Patent
Willand et al.

(10) Patent No.: US 9,920,042 B2
(45) Date of Patent: Mar. 20, 2018

(54) COMPOUNDS FOR USE IN THE TREATMENT OF MYCOBACTERIAL INFECTIONS

(71) Applicant: Universite de Droit et de la Sante de Lille 2, Lille (FR)

(72) Inventors: Nicolas Willand, Lille (FR); Benoit Deprez, Lille (FR); Alain Baulard, Tournai (BE); Priscille Brodin, Paris (FR); Olivier Sperando, Villeneuve-la-Garenne (FR); Vincent Villeret, Wannebecq (BE); Baptiste Villemagne, Saint-Rambert (FR)

(73) Assignee: UNIVERSITE DE DROIT ET DE LA SANTE DE LILLE 2, Lille (FR)

( * ) Notice: Subject to any disclaimer, the term of this patent is extended or adjusted under 35 U.S.C. 154(b) by 0 days.

(21) Appl. No.: 14/430,604

(22) PCT Filed: Sep. 27, 2013

(86) PCT No.: PCT/EP2013/070169
§ 371 (c)(1),
(2) Date: Mar. 24, 2015

(87) PCT Pub. No.: WO2014/049107
PCT Pub. Date: Apr. 3, 2014

(65) Prior Publication Data
US 2015/0225388 A1     Aug. 13, 2015

(30) Foreign Application Priority Data
Sep. 27, 2012   (FR) ...................................... 12 02568

(51) Int. Cl.
| | | |
|---|---|---|
| C07D 277/26 | (2006.01) |
| C07D 277/30 | (2006.01) |
| C07D 417/04 | (2006.01) |
| C07D 213/81 | (2006.01) |
| C07D 249/06 | (2006.01) |
| C07D 249/08 | (2006.01) |
| C07D 271/06 | (2006.01) |
| C07D 277/56 | (2006.01) |
| C07D 277/66 | (2006.01) |

(Continued)

(52) U.S. Cl.
CPC .......... *C07D 417/04* (2013.01); *A61K 31/155* (2013.01); *A61K 31/175* (2013.01); *A61K 31/277* (2013.01); *A61K 31/4192* (2013.01); *A61K 31/421* (2013.01); *A61K 31/426* (2013.01); *A61K 31/428* (2013.01); *A61K 31/4245* (2013.01); *A61K 31/433* (2013.01); *A61K 31/44* (2013.01); *A61K 31/4436* (2013.01); *A61K 31/4439* (2013.01); *A61K 45/06* (2013.01); *C07C 247/18* (2013.01); *C07C 255/57* (2013.01); *C07C 255/60* (2013.01); *C07C 311/37* (2013.01); *C07D 213/81* (2013.01); *C07D 249/06* (2013.01); *C07D 249/08* (2013.01); *C07D 263/32* (2013.01); *C07D 271/06* (2013.01); *C07D 277/26* (2013.01); *C07D 277/28* (2013.01); *C07D 277/30* (2013.01); *C07D 277/56* (2013.01); *C07D 277/66* (2013.01); *C07D 285/08* (2013.01); *C07D 285/12* (2013.01); *C07D 291/04* (2013.01)

(58) Field of Classification Search
CPC ... C07D 277/26; C07D 277/31; C07D 277/30
USPC .................. 548/204, 205; 514/365
See application file for complete search history.

(56) References Cited

U.S. PATENT DOCUMENTS

| | | |
|---|---|---|
| 6,420,427 B1 | 7/2002 | Takahashi et al. |
| 2005/0192275 A1 | 9/2005 | Arora et al. |

(Continued)

FOREIGN PATENT DOCUMENTS

| | | |
|---|---|---|
| EP | 0 915 086 | 5/1999 |
| EP | 1 024 134 | 8/2000 |

(Continued)

OTHER PUBLICATIONS

International Search Report dated Oct. 21, 2013 in International (PCT) Application No. PCT/EP2013/070169.

*Primary Examiner* — Patricia L Morris
(74) *Attorney, Agent, or Firm* — Wenderoth, Lind & Ponack, L.L.P.

(57) ABSTRACT

The present invention concerns compounds of general formula (I):

(I)

in which Y and Z are chosen from CH and N; T is chosen from CO or $SO_2$; n is 1 to 3; R1 represents a group chosen, for example, from C1-C3 alkyl chains unsubstituted or substituted by fluorine, the unsubstituted or substituted cyclic, cyano, azido, alkoxy and phenyl groups; and R is chosen from the azido, cyano, alkinyl and 2-benzothiazolyl groups and an optionally substituted aromatic heterocycle with five vertices; and the use thereof in the treatment of bacterial and mycobacterial infections such as, for example, tuberculosis, leprosy and atypical mycobacterial infections. The present invention also concerns pharmaceutical compositions comprising, as the active ingredient, at least one of the abovementioned compounds and optionally an antibiotic activatable via the EthA pathway.

9 Claims, No Drawings

(51) Int. Cl.

| | | |
|---|---|---|
| *C07D 285/08* | (2006.01) | |
| *C07D 285/12* | (2006.01) | |
| *C07D 291/04* | (2006.01) | |
| *C07C 255/57* | (2006.01) | |
| *C07C 311/37* | (2006.01) | |
| *C07C 247/18* | (2006.01) | |
| *A61K 31/155* | (2006.01) | |
| *A61K 31/175* | (2006.01) | |
| *A61K 31/4192* | (2006.01) | |
| *A61K 31/421* | (2006.01) | |
| *A61K 31/4245* | (2006.01) | |
| *A61K 31/426* | (2006.01) | |
| *A61K 31/428* | (2006.01) | |
| *A61K 31/433* | (2006.01) | |
| *A61K 31/44* | (2006.01) | |
| *A61K 31/4436* | (2006.01) | |
| *A61K 31/277* | (2006.01) | |
| *A61K 31/4439* | (2006.01) | |
| *A61K 45/06* | (2006.01) | |
| *C07C 255/60* | (2006.01) | |
| *C07D 263/32* | (2006.01) | |
| *C07D 277/28* | (2006.01) | |

(56) References Cited

U.S. PATENT DOCUMENTS

| | | |
|---|---|---|
| 2009/0239810 A1 | 9/2009 | Sundaresan et al. |
| 2009/0286791 A1 | 11/2009 | Kitamura et al. |
| 2012/0214785 A1 | 8/2012 | Roth et al. |

FOREIGN PATENT DOCUMENTS

| | | |
|---|---|---|
| WO | 2004/024702 | 3/2004 |
| WO | 2004/026848 | 4/2004 |
| WO | 2008/011131 | 1/2008 |
| WO | 2012/028676 | 3/2012 |

COMPOUNDS FOR USE IN THE TREATMENT OF MYCOBACTERIAL INFECTIONS

The present invention concerns compounds for their use in the treatment of bacterial and mycobacterial infections such as, for example, tuberculosis, leprosy and atypical mycobacterial infections.

The present invention also concerns new compounds that can be used as medicament in particular in the treatment of bacterial and mycobacterial infections such as, for example, tuberculosis, leprosy and atypical mycobacterial infections.

The present invention also concerns pharmaceutical compositions comprising, as the active ingredient, at least one of the abovementioned compounds and optionally an antibiotic activatable via the EthA pathway.

The present invention also concerns products (kits) containing at least one of the aforementioned compounds and at least one antibiotic activatable via the EthA pathway as combination products for use simultaneously, separately or spread out in time, in the therapy of tuberculosis leprosy or general mycobacterial infections.

Tuberculosis kills 2 million people every year in the world. The AIDS epidemics and the emergence of strains that are multi-resistant to antibiotics contribute to exacerbating the impact of this illness, considered by the World Health Organization as responsible for an increasingly dangerous worldwide epidemic and as a health emergency on a global scale.

An increasing number of *Mycobacterium tuberculosis* strains is characterized nowadays by multi-resistance to first-line antibiotics such as isoniazid (INH) and rifampicin (RIF). These antibiotics have a high therapeutic index (the therapeutic index of an active ingredient is the ratio of therapeutic dose to toxic dose) and must thus be replaced by second-line antibiotics such as ethionamide (ETH) to which the strains are not resistant but which have the disadvantage of having a lower therapeutic index.

One strategy consisting in increasing the activity of ethionamide (ETH) by associating it to a specific compound has already been considered. In fact, ETH is a prodrug that is transformed in vivo into a therapeutically active form by the EthA enzyme (see the article "Activation of the prodrug ethionamide is regulated in mycobacteria" 2000 Journal of Biological Chemistry). The resistances to ETH observed arise from the fact that the transcriptional repressor EthR of *M. tuberculosis* controls the expression, of the EthA enzyme and restricts or even prevents the transformation of ETH into a therapeutically active substance. The aforementioned strategy is based on the combination of ETH and of a compound that inhibits EthR and thus suppresses the control of *M. tuberculosis* over EthA. Thus, the document "Ethionamide Boosters Combining Bioisosteric Replacement and Structure-Based Drug Design to Solve Pharmacokinetic Issues in a series of potent 1,2,4-Oxadiazole EthR Inhibitors", published in 2012 in the Journal of Medicinal Chemistry, discloses compounds likely to potentiate the efficiency of ethionamide by inhibiting EthR of *M. tuberculosis*.

One aim of the present invention is to propose new compounds likely to potentiate the activity of antibiotics activatable via the EthA pathway, in particular ethionamide, by inhibition of EthR.

Another aim of the present invention is to propose compounds such as previously mentioned that, in combination with an antibiotic activatable via the EthA pathway, and at identical antibiotics dosage, enable a greater efficiency to be achieved or that enable the aforementioned antibiotics dosage to be reduced whilst achieving a given efficiency.

Another aim of the present invention is to propose compounds such as previously mentioned that are simple and inexpensive to produce.

Another aim of the present invention is to propose compounds such as previously mentioned that are satisfactorily soluble in a biologic fluid.

Another aim of the present invention is to propose compounds such as previously mentioned that are likely to be active in particular orally and/or that cause fewer side effects.

To achieve at least one of the aforementioned aims, the present invention thus proposes compounds of the general formula (I):

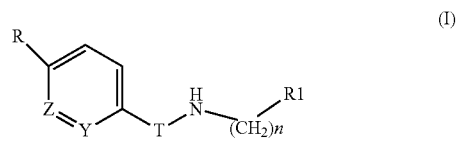

(I)

in which

Y and Z are chosen, independently from one another, from CH and N;

T is chosen from CO or $SO_2$;

n is an integer greater than or equal to 1 and lower than or equal to 3;

R1 represents a group chosen from linear or branched C1-C3 alkyl chains, linear or branched and substituted C1-C3 alkyl chains, in particular linear or branched C1-C3 alkyl chains substituted by at least one fluorine atom, C3-C6 cyclic groups, the cyano group, the azido group, C1-C3 alkoxy chains, an unsubstituted phenyl group, a phenyl group substituted by one, two or three substituents chosen, independently from one another, from linear or branched C1-C3 alkyl chains, trifluoromethyl, linear or branched C1-3 alkoxy chains, halogens (F, Cl, Br, I), 6-membered heterocycles comprising 1 or 2 nitrogen atoms in the ring and aromatic 5-membered heterocycles;

R is chosen from the azido, cyano, 2-benzothiazolyl groups and the following groups (R-1) to (R-10):

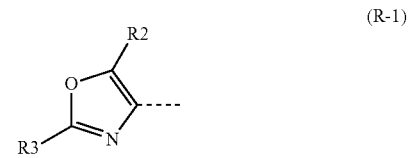

(R-1)

(R-2)

(R-3)

(R-4)

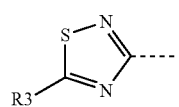
(R-5)

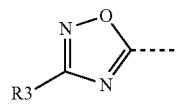
(R-6)

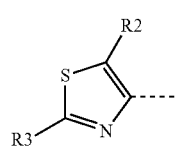
(R-7)

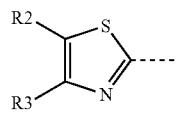
(R-8)

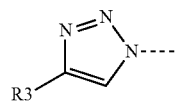
(R-9)

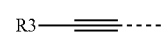
(R-10)

in which:

$R2$ is chosen from H, F, Cl, Br, I;

$R3$ is a group chosen from H, linear or branched C1-C6 alkyl chains, linear or branched C1-C6 alkyl chains substituted by at least one fluorine atom, C3-C6 cyclic groups, the cyanomethyl group, the azidomethyl group, linear or branched C1-C4 alkoxy chains, C1-C4 hydroxyalkyl groups, C1-C4 alkyl methyl ester groups, C1-C4 methylcarbonylamino alkyl groups, C1-C4 methylsulfone alkyl groups, the unsubstituted phenyl group, a phenyl group substituted by one, two or three substituents chosen, independently from one another, from C1-C3 alkyl chains, trifluoromethyl, C1-3 alkoxy chains, aromatic heterocycles such as for example 2-pyridinyl, 3-pyridinyl, 4-pyridinyl, substituted aromatic heterocycles, in particular heterocycles substituted by a linear or branched C1-C5 alkyl chain, aromatic heterocycles substituted by at least one fluorine atom, in particular aromatic heterocycles substituted by one, by two or by three fluorine atoms or by a group chosen among the following groups (II-a and II-b):

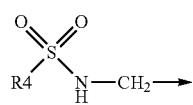
(II-a)

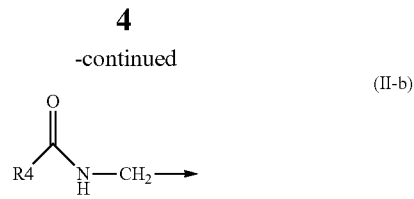
(II-b)

in which $R4$ is a group chosen from H, linear or branched C1-C4 alkyl chains, the phenyl group, a phenyl group substituted by at least one halogen atom, in particular substituted by one halogen atom, a phenyl group substituted by a linear or branched C1-C4 alkyl chain, a phenyl group substituted by a linear or branched C1-C4 alkoxy chain and a phenyl group substituted by a trifluoromethyl group;

for their use as medicament, in particular for their use in the treatment of bacterial and mycobacterial infections, notably in the treatment of tuberculosis, leprosy or atypical mycobacterial infections.

"C1-C4 alkyl methyl ester groups" in the sense of the present invention is understood to mean that the alkyl radical comprises 1 to 4 carbon atoms and that the methyl radical is bonded to anyone of the groups R-1 to R-10.

In the entire description of the present invention, the terms "substituted alkyl chains" represent, regardless of the number of carbons of the chain under consideration, alkyl chains of which at least one hydrogen bound to a carbon atom is substituted; when the chain comprises at least two substituents, these substituents can be bound to the same carbon atom or to different carbon atoms.

When the substituent of the alkyl chain is explicitly indicated, the latter's position is not limited according to the present invention.

When at least two substituents of the alkyl chain are explicitly indicated, the latter can be bound to the same carbon or to different carbons.

The terms "alkoxy chains" denote all alkoxy chains comprising the number of carbons indicated and one oxygen atom binding two carbon atoms of the chain, regardless of the latter's position.

Atypical mycobacterial infections are defined here as mycobacterial infections caused by at least one *mycobacterium* other than *M. Tuberculinum* and in particular mycobacterial infections involving *M. Kansasii*.

In the entire present application, the aforementioned chains that are substituted by at least one halogen atom can in particular be substituted by one halogen atom, two halogen atoms or three halogen atoms. The halogen atoms can be different from one another on a same chain. Halogenated substituents are chosen independently from one another. They can substitute a same carbon atom or different carbon atoms.

The present invention also concerns compounds of the general formula (II):

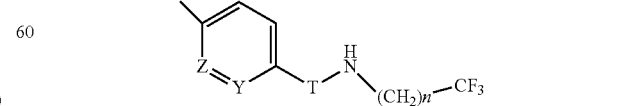
(II)

in which Y, Z, T, R and n are defined as previously.

The present invention also concerns compounds that correspond to the following formula (III):

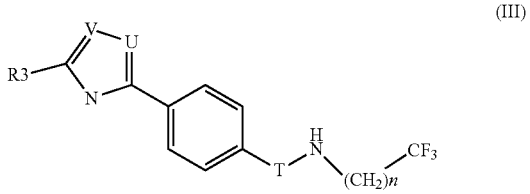

(III)

in which U is chosen from CH and N; and V is chosen from O or S; n, T and R3 being such as previously defined.

The present invention also concerns compounds of the following formula (IV):

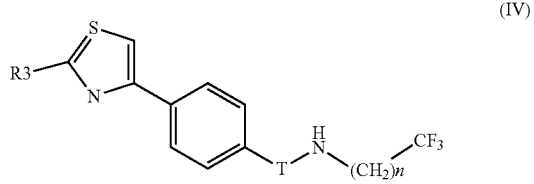

(IV)

in which n, T and R3 are defined as previously.

Advantageously, T=CO and R3 is chosen from the following groups: —CH$_2$SO$_2$R' wherein the radical R' is a group tert-butyl, methyl, isobutyl, isopentyl, isohexyl, 4-pyridinyl and 4-pyridinyl substituted by a linear C1-C4 alkyl chain.

Advantageously, R3 can be, whatever n and T, a 4-pyridinyl group substituted by a methyl group or ethyl chain. In this case, the cycle is advantageously substituted in position 3, i.e. in ortho position relative to the nitrogen atom of the pyridinyl group.

The present invention also concerns the aforementioned compounds for use as medicament, in particular for their use in the treatment of bacterial and mycobacterial infections, notably in the treatment of tuberculosis, leprosy or atypical mycobacterial infections.

The present invention also concerns a pharmaceutical composition comprising, as the active ingredient, at least one of the compounds as previously mentioned, in particular a compound of general formula (II), (III) or (IV) and/or at least one compound of general formula (I) as previously mentioned and one pharmaceutically acceptable excipient.

Within the pharmaceutical compositions according to the invention, the compound or compounds used as active ingredient can be used in a quantity that enables unit doses comprised between 0.3 mg and 1 g approximately to be administered. Within the pharmaceutical compositions according to the invention, the antibiotic or antibiotics activatable via the enzymatic EthA pathway, when present, are advantageously used in a quantity enabling the administration of unit doses equal to or lower than the doses usually recommended by the World Health Organization (WHO, Treatment of tuberculosis: Guidelines for National Programmes. 2003; WHO/CDS/TB2003.313.), national or non-governmental health organizations or the competent pharmaceutical laboratories.

The one skilled in the art is able to choose one or several pharmaceutically acceptable excipients depending on the route of administration of the pharmaceutical composition. The one skilled in the art will of course ensure in doing so that the excipient or excipients used are compatible with the intrinsic properties attached to the composition according to the present invention. Furthermore, the form of the medicament or pharmaceutical composition (for example a solution, a suspension, an emulsion, tablets, capsules, suppositories etc.) will depend on the chosen administration route.

Thus, in the sense of the present invention, the medicament or pharmaceutical composition can be administered by any appropriate route, for example oral, anal, local (topical for example), systemic, intravenous, intramuscular or mucosal route, or else by using a patch, or else in encapsulated form in or immobilized on liposomes, microparticles, microcapsules, associated to nanoparticles and similar. By way of non-limiting examples of excipients suitable for administration by the oral route, one can notably cite talcum, lactose, starch and its derivatives, cellulose and its derivatives, polyethylene glycols, acrylic acid polymers, gelatin, magnesium stearate, animal, vegetal or synthetic fats, paraffin derivatives, glycols, stabilizers, preservatives, antioxidants, wetting agents, anti-caking agents, dispersants, emulsifiers, taste modifying agents, penetrating agents, solubilizing agents etc. The formulation and administration techniques for the medicaments and pharmaceutical compositions are well known in the art here under consideration, the one skilled in the art can notably refer to the work Remington's Pharmaceutical Sciences, latest edition.

The present invention also has the aim of using at least one compound according to the invention for the manufacture of a medicament intended for the prevention and/or treatment of bacterial infections, preferably mycobacterial infections, and more, particularly of tuberculosis, leprosy or atypical mycobacterial infections.

Advantageously, the pharmaceutical composition further comprises, as active ingredient, at least one antibiotic chosen from antibiotics activatable via the enzymatic EthA pathway. Ethionamide, prothionamide, isoxyl and thioacetazone are examples of antibiotics activatable via the EthA pathway. However, the invention is, not limited to these antibiotics.

The present invention also concerns a kit or product containing at least one compound of formula (II) and/or at least one compound of general formula (I) and at least one antibiotic chosen from antibiotics activatable via the enzymatic EthA pathway as combination products for use, simultaneously, separately or spread out in time, in the therapy of tuberculosis, leprosy or general mycobacterial infections.

According to the present invention, the term "treatment" designates the curative treatment and/or prophylactic treatment of the aforementioned infections. The term "treatment" includes all improvement of the patient's state, in particular any diminution of the number of bacteria present in at least one infection site of the patient.

In the present invention, an antibiotic activatable via the EthA pathway is defined as any substance that at least in vitro reacts with the EthA enzyme to produce a substance having antibiotic properties. The one skilled in the art is able to determine if an antibiotic is activatable by the EthA pathway for example by applying the method described in the following publication: "Activation of the prodrug ethionamide is regulated in mycobacteria" 2000, Journal of Biological Chemistry.

EXPERIMENTAL SECTION

Microwave Synthesis

Microwave synthesis was performed in a CEM Discover™ microwave oven.

Analysis by Thin-Layer Chromatography

The thin-layer chomatographies (TLC) were performed on aluminum plates covered with a layer of 0.25 mm thickness of silica gel 60 $F_{254}$ Merck.

LC-MS Analyses

The LC-MS analyses were performed on two systems:
A triple quadrupole Varian 1200 ws system. UV detection is performed at wave lengths of 215 and 254 nm.
A Waters Alliance Micromass ZQ 2000 system. Detection is performed by means of Waters 2996 diode array system.

These apparatus are equipped with a C18 TSK-gel Super ODS 2 μm (50×4.6 mm) column or an XBridge C18 (Waters) 5 μm (50×4.6 mm) column. The injection volumes are 20 μL.

Two gradients were used
10 min: 100% $H_2O$/0.1% HCOOH up to 95% ACN/0.1% HCOOH in 7 minutes at a rate of 1 mL·min$^{-1}$.
5 min: 100% $H_2O$/0.1% HCOOH up to 95% ACN/0.1% HCOOH in 3 minutes at a rate of 2 mL.min$^{-1}$.

Method a: Varian, gradient 10 min, column SODS
Method b: Waters, gradient 10 min, column SODS
Method c: Waters, gradient 5 min, column XBridge
Method d: Waters, gradient 10 min, column XBridge NMR Analyses Nuclear magnetic resonance spectra (NMR) were performed on a Brücker DRX 300 MHz spectrometer. The chemical shifts δ are expressed in ppm relative to TMS and the coupling constants J in Hz (Hertz). The peaks are described according to the model: δ (splitting pattern, number of protons per integration, J).

The following abbreviations have been used for the multiplicity of the: s=singulet, d=doublet, t=triplet, q=quadruplet, qn=quintuplet, sx=sextuplet, sp=septuplet, n=nonuplet, br=broad (large).

Purification by Chromatography on a Pre-Packed Silica Column

The chromatographies on a pre-packed silica column were performed on columns of the brand AIT Chromato with a grain size from 20 to 40 μm or Grace Reveleris with a grain size of 40 μm, using a Flashmart pump.

Purification by High Pressure Liquid Chromatography (HPLC)

The purifications by preparative HPLC were performed by means of a Varian ProStar apparatus using an Omnisphere 10 $C_{18}$ 250 mm×41.4 mm Dynamax column. The gradient used starts from a mixture (20% acetonitrile/80% water/0.1% formic acid) up to a mixture (100% acetonitrile/0.1% formic acid). Detection is performed at wavelengths of 215 and 254 nm.

Melting Point

The melting points of the recrystallized products were measured using the capillaries method, on Büchi B-540 apparatus.

Scheme 1:

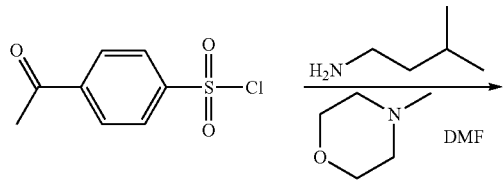

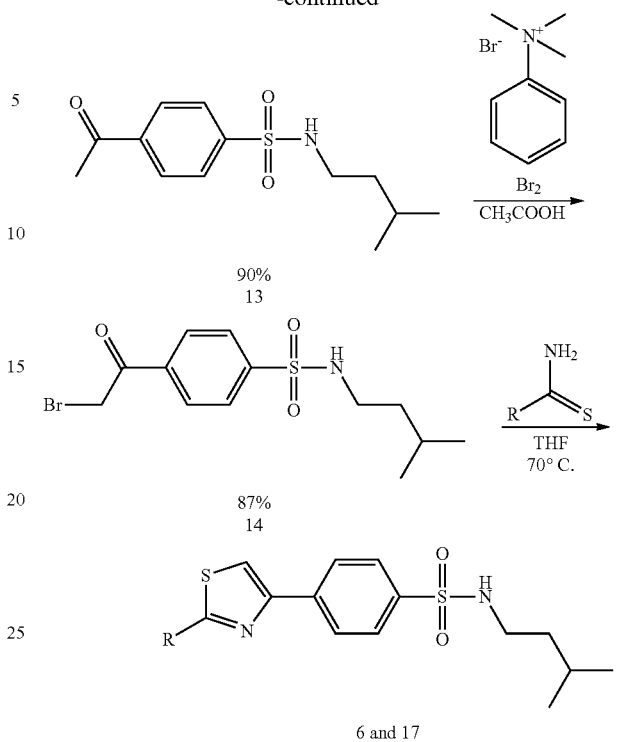

Compound 13: 4-acetyl-N-isopentyl benzene sulfonamide

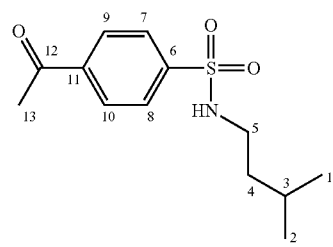

3 g (1 eq.) 4-acetyl benzene sulfonic acid chloride are added to a solution of 2.39 mL (1.5 eq.) 3-methyl-butylamine and 7.54 mL (5 eq.) N-methylmorpholine in 200 mL DMF on a molecular sieve. The mixture is agitated during 3 h at AT. The DMF is evaporated under reduced pressure. The residue is taken over in the ethyl acetate and then washed by means of an aqueous solution of HCl 1N (2×) and in brine (1×). The organic phases are dried on magnesium sulfate and then concentrated under reduced pressure to yield 3.34 g (90%) of beige powder.

LC-MS: $t_R$=5.61 min (method a); m/z: [M+H]$^+$=270

CCM: $R_f$=0.44 (AcOEt 3:7 petroleum ether)

NMR $^1$H (CD$_3$OD, 300 MHz): δ ppm=8.16 (d, 2H, $^3$J=8.67 Hz, 9+10); 7.95 (d, 2H, $^3$J=8.67 Hz, 7+8); 2.89 (t, 2H, $^3$J=7.16 Hz); 2.65 (s, 3H, 13); 1.61 (n, 1H, $^3$J=6.72 Hz, 3); 1.32 (q, 2H, $^3$J=7.08 Hz, 4); 0.84 (d, 6H, $^3$J=6.62 Hz, 1+2)

Compound 14: 4-(2-bromoacetyl)-N-isopentyl benzene sulfonamide

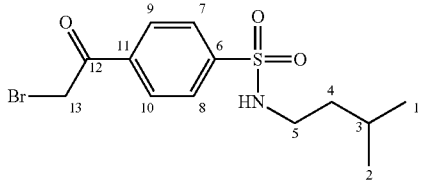

4.466 g (1 eq.) trimethylphenyl ammonium tribromide are added to a solution of 3.2 g (1 eq.) of 4-acetyl-N-isopentyl benzene sulfonamide (13) in 150 mL glacial acetic acid. The reaction mixture is agitated during 3 h at AT. The acetic acid is evaporated under reduced pressure, the yellow solid thus obtained is taken over in the ethyl acetate and then washed using water (2×) and in brine (1×). The organic phase is dried on magnesium sulfate and then evaporated under reduced pressure to yield 4.02 g (quantitative) of a yellow oil.

LC-MS: $t_R$=6.26 min (method a); m/z: [M+H]$^+$=349

NMR $^1$H (CD$_3$OD, 300 MHz): δ ppm=8.18 (d, 2H, $^3$J=8.70 Hz, 7-8); 7.98 (d, 2H, $^3$J=8.70 Hz, 9-10); 4.71 (s, 2H, 13); 2.90 (t, 2H, $^3$J=7.10 Hz, 5); 1.62 (n, 1H, $^3$J=6.70 Hz, 3); 1.32 (q, 2H, $^3$J=6.90 Hz, 4); 0.84 (d, 6H, $^3$J=6.60 Hz, 1+2)

Compound 6: 4-(2-methylthiazol-4-yl)-N-isopentyl benzene sulfonamide

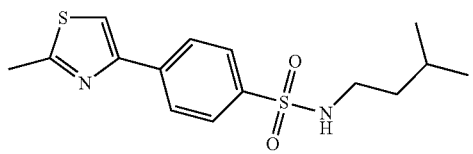 [SMILES: Cc1nc(-c2ccc(S(=O)(=O)NCCC(C)C)cc2)cs1]

LC-MS: $t_R$=6.4 min (method a); m/z: [M+H]$^+$=325
CCM: $R_f$=0.34 (AcOEt 3:7 petroleum ether)

NMR $^1$H (CD$_2$Cl$_2$, 300 MHz): δ ppm=8.07 (d, 2H, J=8.5 Hz), 7.9 (d, 2H, J=8.5 Hz), 7.56 (s, 1H), 4.48 (t, 1H, J=5.7 Hz), 2.98 (m, 2H), 2.8 (s, 3H), 1.59 (n, 1H, J=6.7 Hz), 1.13 (sextuplet, 2H, J=7.22 Hz), 0.86 (d, 6H, J=6.78 Hz)

Compound 17: 4-(2-(cyanomethyl)thiazol-4-yl)-N-isopentyl benzene sulfonamide

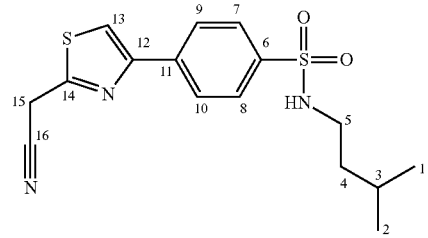

575 mg (1 eq.) 2-cyanothioacetamide are added to a solution of 2 g (1 eq.) 4-(2-bromoacetyl)-N-isopentyl benzene sulfonamide (14) in 200 mL of THF on a molecular sieve. The reaction mixture is agitated under THF reflux during 28 h. The THF is then evaporated under reduced pressure then the solid thus obtained is taken over in the ethyl acetate, washed using water (2×) and then in brine (1×). The organic phase is dried on magnesium sulfate and then evaporated under reduced pressure. The brown solid is recrystallized in 5 mL ethanol to yield 946 mg (47%) of pale yellow powder.

LC-MS: $t_R$=5.67 min (method a); m/z: [M+H]$^+$=350

NMR $^1$H (CD$_3$OD, 300 MHz): δ ppm=8.15 (d, 2H, $^3$J=8.70 Hz, 9+10); 8.05 (s, 1H, 13); 7.90 (d, 2H, $^3$J=8.70 Hz, 7+8); 4.43 (s, 1H, 15); 2.90 (t, 2H, $^3$J=7.20 Hz, 5); 1.52-1.68 (m, 1H, 3): 1.33 (q, 2H, $^3$J=7.10 Hz, 4); 0.84 (d, 6H, $^3$J=6.65 Hz, 1+2)

NMR $^{13}$C (CD$_3$OD, 75 MHz): δ ppm=159.4 (14); 153.7 (12); 139.9 (11); 137.5 (6); 127.2 (7+8); 126.5 (9+10); 117.0 (13); 115.9 (16); 41.0 (5); 38.1 (4); 25 (3); 21.2 (1+2); 20.9 (15)

Scheme 2:

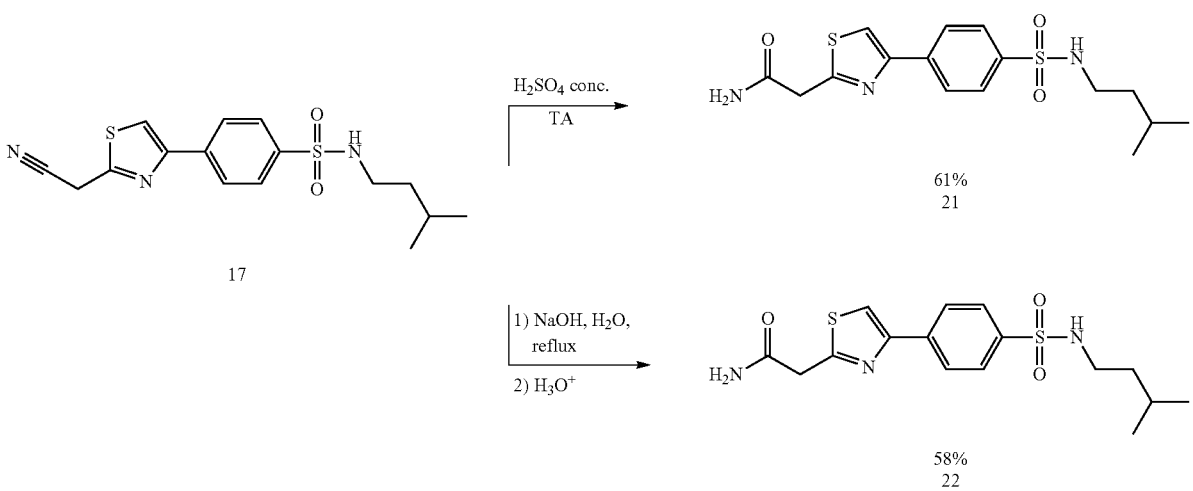

Compound 21: 2-(4-(4-(N-isopentylsulfamoyl)phenyl)thiazol-2-yl)acetamide

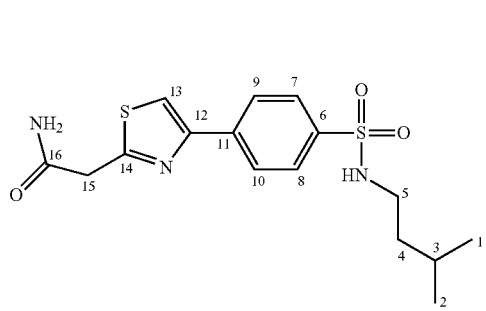

100 mg 4-(2-(cyanomethyl)thiazol-4-yl)-N-isopentyl benzene sulfonamide (17) are solubilized in 100 μL sulfuric acid at 96%. The solution is agitated at AT during 12 h. The reaction medium is then poured into 100 μL of ammonia solution at 28% at 0° C. Ammonia is then added until a pH of 9 is reached. The solution is then filtered, the filtrate pH is neutralized with HCl 1N and then extracted using ethyl acetate. The organic phases are collected, dried on magnesium sulfate and then evaporated under reduced pressure to yield 64 mg (61%) of white powder.

LC-MS: $t_R$=5.20 min (method a); m/z: $[M+H]^+$=368

NMR $^1$H (CD$_3$OD, 300 MHz): δ ppm=8.12 (d, 2H, $^3$J=8.61 Hz, 9+10); 7.97 (s, 1H, 13); 7.89 (d, 2H, $^3$J=8.61 Hz, 7+8); 4.05 (s, 1H, 15); 2.90 (t, 2H, $^3$J=7.18 Hz, 5); 1.62 (n, 1H, $^3$J=6.40 Hz, 3); 1.34 (q, 2H, $^3$J=7.08 Hz, 4); 0.84 (d, 6H, $^3$J=6.62 Hz, 1+2)

NMR $^{13}$C (CD$_3$OD, 75 MHz): δ ppm=173.2 (16); 165.9 (14); 154.4 (12); 141.2 (11); 139.6 (6); 128.7 (7+8); 127.9 (9+10); 118.1 (13); 42.5 (5); 39.7 (4); 26.6 (3); 22.8 (1+2)

Compound 22: 2-(4-(4-(N-isopentylsulfamoyl)phenyl)thiazol-2-yl) acetic acid

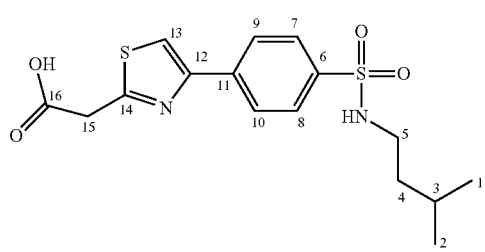

A solution of 200 mg (1 eq.) 4-(2-(cyanomethyl)thiazol-4-yl)-N-isopentyl benzene sulfonamide (17) in 2.5 mL water and 45.8 mg (2 eq.) NaOH is heated under reflux during 15 h. The pH is then adjusted to 4-5 at AT by means of a solution of glacial acetic acid. The produce is extracted using ethyl acetate. The organic phases are collected, washed with an aqueous solution of HCl with a pH=4, dried on magnesium sulfate and then evaporated under reduced pressure to yield 122 mg (58%) of beige powder.

LC-MS: $t_R$=5.07 min (method a); m/z: $[M+H]^+$=369

NMR $^1$H (CD$_3$OD, 300 MHz): δ ppm=8.11 (d, 2H, $^3$J=8.80 Hz, 9+10); 7.97 (s, 1H, 13); 7.89 (d, 2H, $^3$J=8.80 Hz, 7+8); 2.90 (t, 2H, $^3$J=7.30 Hz, 5); 1.61 (n, 1H, $^3$J=6.70 Hz, 3); 1.34 (q, 2H, $^3$J=7.20 Hz, 4); 0.84 (d, 6H, $^3$J=6.60 Hz, 1+2)

Scheme 3:

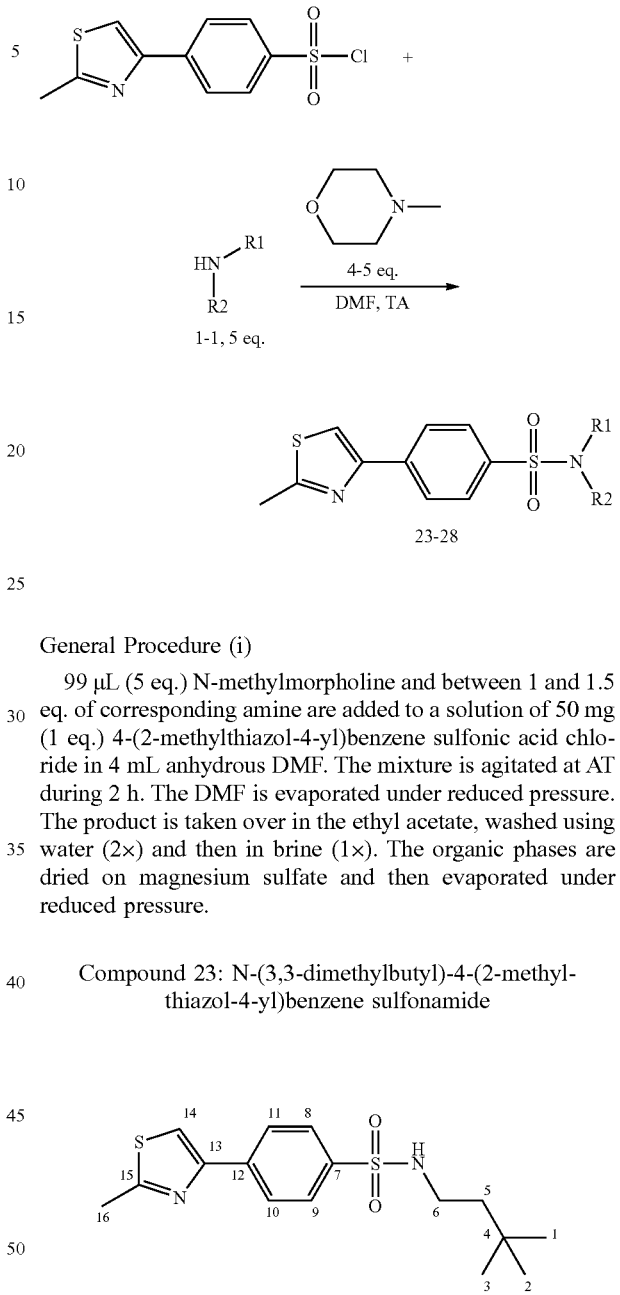

General Procedure (i)

99 μL (5 eq.) N-methylmorpholine and between 1 and 1.5 eq. of corresponding amine are added to a solution of 50 mg (1 eq.) 4-(2-methylthiazol-4-yl)benzene sulfonic acid chloride in 4 mL anhydrous DMF. The mixture is agitated at AT during 2 h. The DMF is evaporated under reduced pressure. The product is taken over in the ethyl acetate, washed using water (2×) and then in brine (1×). The organic phases are dried on magnesium sulfate and then evaporated under reduced pressure.

Compound 23: N-(3,3-dimethylbutyl)-4-(2-methylthiazol-4-yl)benzene sulfonamide

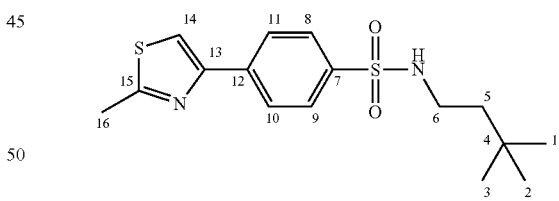

Procedure (i) with 38.7 μL (1.5 eq.) 3,3-dimethylbutylamine.

26.5 mg (44%) of beige powder.

LC-MS: $t_R$=6.79 min (method a); m/z: $[M+H]^+$=339

NMR $^1$H (DMSO-d$_6$, 300 MHz): δ ppm=8.09 (d, 2H, $^3$J=8.70 Hz, 10+11); 7.89 (d, 2H, $^3$J=8.70 Hz, 8+9); 7.84 (s, 1H, 14); 2.86-2.92 (m, 2H, 6); 2.77 (s, 3H, 16); 1.35-1.40 (m, 2H, 5); 0.85 (s, 9H, 1+2+3)

NMR $^{13}$C (DMSO-d$_6$, 75 MHz): δ ppm=168.7 (15); 154.4 (13); 140.9 (7); 139.5 (12); 128.6 (8+9); 127.8 (10+11); 116.9 (14); 44.3 (5); 40.8 (6); 30.5 (4); 29.7 (1+2+3); 18.9 (16).

Compound 24: 4-(2-methylthiazol-4-yl)-N-(2,2,2-trifluoropropyl)benzene sulfonamide

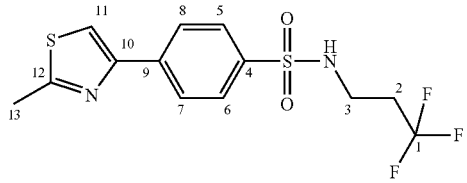

Procedure (i) with 26.9 mg (1 eq.) 2,2,2-trifluoropropylamine hydrochloride.

26.6 mg (39%) of beige powder.

LC-MS: $t_R$=5.80 min (method a); m/z: [M+H]$^+$=351

NMR $^1$H (CD$_3$OD, 300 MHz): δ ppm=8.10 (d, 2H, $^3$J=8.80 Hz, 7+8); 7.90 (d, 2H, $^3$J=8.80 Hz, 5+6); 7.86 (s, 1H, 11); 3.12 (t, 2H, $^3$J=7.3) Hz, 3); 2.77 (s, 3H, 13); 0.2.39 (qt, 2H, $^3$J$_{2-1}$=10.80 Hz, $^3$J$_{2-3}$=7.30 Hz, 2)

NMR $^{13}$C (CD$_3$OD, 75 MHz): δ ppm=168.7 (12); 154.3 (10); 140.5 (4); 139.8 (9); 128.6 (5+6); 127.9 (7+8); 127.6 (q, $^1$J$_{C-F}$=276.1 Hz, 1); 117.1 (11); 37.39 (d, $^3$J$_{C-F}$=3.10 Hz; 3); 35.21 (q, $^2$J$_{C-F}$=27.9 Hz, 2); 18.9 (13).

Compound 25: 4-(2-methylthiazol-4-yl)-N-(2,2,3,3,3-pentafluoropropyl)benzene sulfonamide

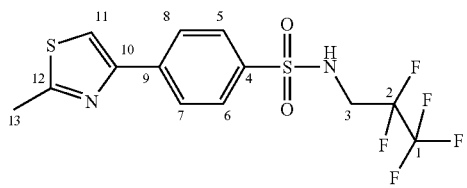

Procedure (i) with 38.9 μL (1 eq.) 2,2,3,3,3-pentafluoropropylamine, 100 mg sulfonic acid chloride, 8 mL anhydrous DMF and 198 μL N-methylmorpholine.

40.1 mg (29%) of beige powder.

LC-MS: $t_R$=6.22 min (method a); m/z: [M+H]$^+$=387

NMR $^1$H (CD$_3$OD, 300 MHz): δ ppm=8.10 (d, 2H, $^3$J=8.80 Hz, 7+8); 7.91 (d, 2H, $^3$J=8.80 Hz, 5+6); 7.86 (s, 1H, 11); 3.70 (td, 2H, $^3$J$_{3-2}$=15.80 Hz, $^4$J$_{3-1}$=0.8 Hz, 3); 2.77 (s, 3H, 13).

Compound 26: 4-(2-methylthiazol-4-yl)-N-(2,2,2-trifluoroethyl)benzene sulfonamide

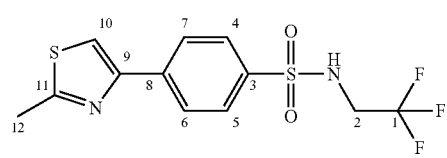

Procedure (i) with 24.4 mg (1 eq.) 2,2,2-trifluoroethylamine hydrochloride.

19.8 mg (31%) of beige powder.

LC-MS: $t_R$=5.53 min (method a); m/z: [M+H]$^+$=337

NMR $^1$H (CD$_3$OD, 300 MHz): δ ppm=8.09 (d, 2H, $^3$J=8.80 Hz, 6+7); 7.91 (d, 2H, $^3$J=8.80 Hz, 4+5); 7.85 (s, 1H, 10); 3.68 (q, 2H, $^3$J=9.00 Hz, 2); 2.80 (s, 3H, 12)

NMR $^{13}$C (CD$_3$OD, 75 MHz): δ ppm=168.7 (11); 154.3 (9); 141.2 (8); 139.8/8); 125.0 (q. $^1$J$_{C-F}$=277 Hz, 1); 117.1 (10); 45.06 (q, $^2$J$_{C-F}$=35.0 Hz, 2); 12.9 (12).

Compound 27: 4-(2-methylthiazol-4-yl)-N-(4,4,4-trifluorobutyl)benzene sulfonamide

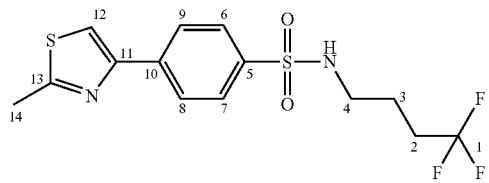

Procedure (i) with 55.7 mg (1.2 eq.) 4,4,4-trifluorobutylamine, 100 mg sulfonic acid chloride, 5 mL anhydrous DMF and 198 μL N-methylmorpholine.

75.1 mg (54%) of beige powder.

LC-MS: $t_R$=6.13 min (method b); m/z: [M+H]$^+$=365

NMR $^1$H (CD$_3$OD, 300 MHz): δ ppm=8.02 (d, 2H, $^3$J=8.74 Hz, 8+9); 7.89 (d, 2H, $^3$J=8.74 Hz, 6+7); 7.46 (s, 1H, 12); 5.10 (t, 1H, $^3$J=6.39 Hz, NH); 3.03 (q, 2H, $^3$J=6.64 Hz, 4); 2.22-2.06 (m, 2H, 2); 1.76 (qn, 2H, $^3$J=7.33 Hz, 3)

NMR $^{13}$C (CDCl$_3$, 75 MHz): δ ppm=166.8 (13); 153.2 (11); 138.8 (10); 138.5 (5); 127.6 (6+7); 127.0 (8+9); 126.9 (q, $^1$J$_{C-F}$=276 Hz, 1); 115.2 (12); 42.0 (4); 30.9 (q, $^2$J$_{C-F}$=29.0 Hz, 2); 22.6 (3); 19.4 (14).

Compound 28: N-(2,2,3,3,4,4,4-heptafluorobutyl)-4-(2-methylthiazol-4-yl)benzene sulfonamide

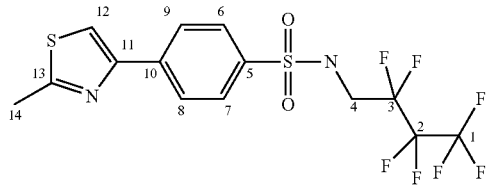

Procedure (i) with 29.2 μL (1.2 eq.) 2,2,3,3,4,4,4-heptafluorobutylamine.

34 mg (44%) of beige powder.

LC-MS: $t_R$=6.65 min (method b); m/z: [M+H]$^+$=437

NMR $^1$H (CDCl$_3$ 300 MHz): δ ppm=8.02 (d, 2H, $^3$J=8.70 Hz, 8+9); 7.88 (d, 2H, $^3$J=8.70 Hz, 6+7); 7.49 (s, 1H, 12); 5.50 (br s, 1H, NH); 3.75 (td, 2H, $^3$J$_{4-3}$=15.30 Hz, $^4$J$_{4-2}$=5.10 Hz, 4); 2.80 (s, 3H, 14)

NMR $^{19}$F uncoupled $^1$H (CDCl$_3$, 282 MHz): δ ppm=−127.36/−127.51 (m, 2F, 3); −118.74 (qt, 2F, $^3$J$_{2-1}$=9.30 Hz, $^3$J$_{2-3}$=5.60 Hz, 2); −80.71, (t, 3F, $^3$J=9.30 Hz, 1).

Scheme 4:

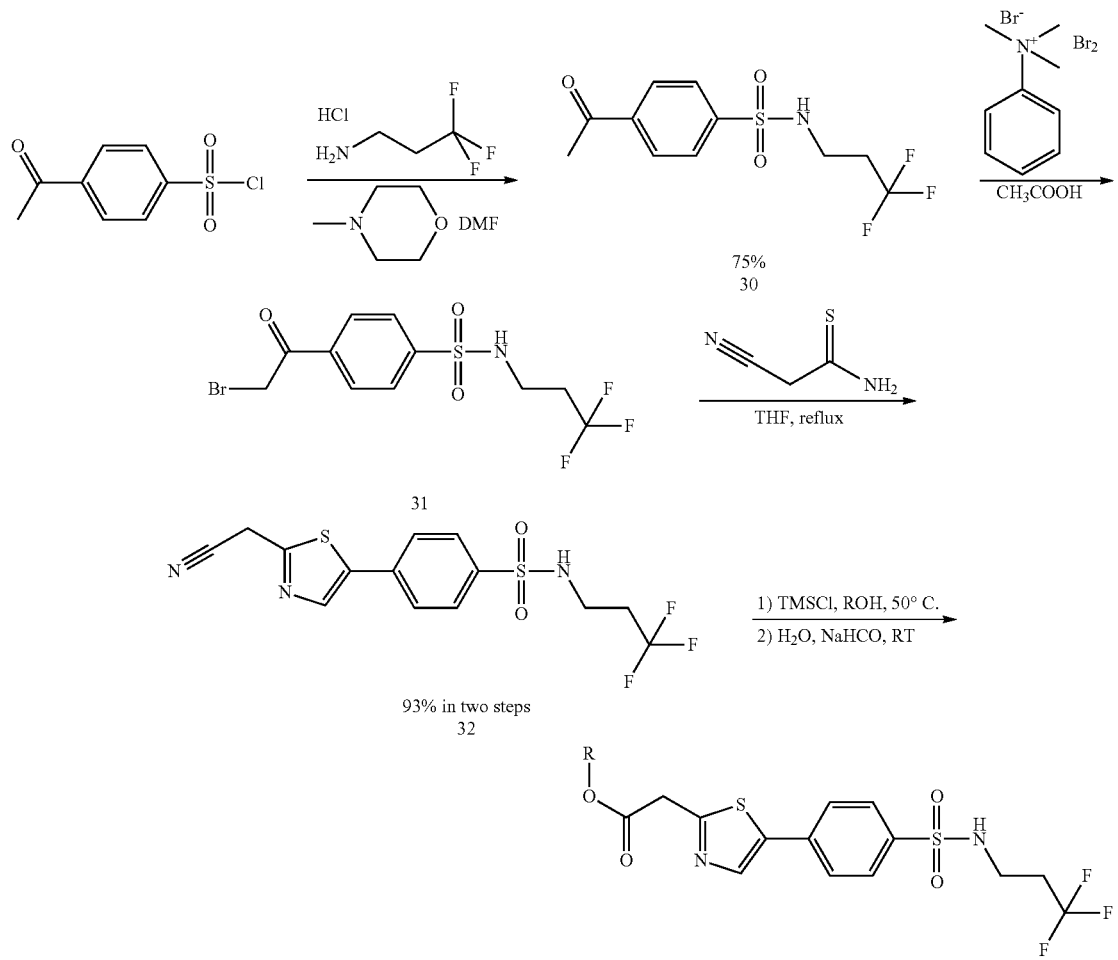

R = Me 33 47%
    Et 34 59%
    iPr 35 26%

Compound 30: 4-acetyl-N-(3,3,3-trifluoropropyl)benzene sulfonamide

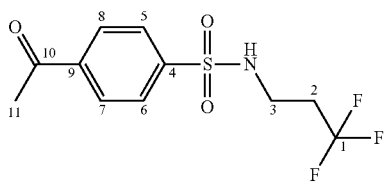

754 μL (5 eq.) N-methylmorpholine and 300 mg (1 eq.) 4-acetylbenzene sulfonic acid chloride are successively added to a solution of 186 mg (1.2 eq.) 3,3,3-trifluoropropylamine hydrochloride in 10 mL anhydrous DMF. The mixture is agitated during 2 h at AT. The DMF is evaporated under reduced pressure. The product is taken over in the ethyl acetate and then washed by means of an aqueous solution of HCl 1N (2×) and then in brine (1×). The organic phases are dried on magnesium sulfate and then concentrated under reduced pressure to yield 303 mg (75%) of pale yellow powder.

LC-MS: $t_R$=5.33 min (method a); m/z: $[M+H]^+$=296

NMR $^1$H (DMSO-$d_6$, 300 MHz): δ ppm=8.15 (d, 2H, $^3J$=8.60 Hz, 7+8); 8.09 (br s, 1H, NH); 7.93 (d, 2H, $^3J$=8.60 Hz, 5+6); 2.99 (t, 2H, $^3J$=6.90 Hz, 3); 2.43 (qt, 2H, $^3J_{2-1}$=11.22 Hz, $^3J_{2-3}$=6.96 Hz, 2)

Compound 31: 4-(2-bromoacetyl)-N-isopentyl benzene sulfonamide

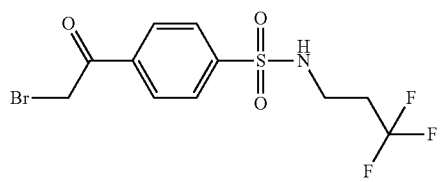 [SMILES: O=C(CBr)c1ccc(S(=O)(=O)NCCC(F)(F)F)cc1]

A solution of 303 mg (1 eq.) 4-acetyl-N-(3,3,3-trifluoropropyl)benzene sulfonamide (30) in 35 mL of glacial acetic acid is added drop by drop to a solution of 386 mg (1 eq.) trimethylphenylammonium tribromide in 30 mL of glacial acetic acid. The reaction mixture is agitated during 4 h at AT. 0.1 eq. brominating reagent are added to consume completely the residual non-brominated ketone. The acetic acid is evaporated under reduced pressure, the yellow solid thus obtained is taken over in the ethyl acetate and then washed using water (2×) and in brine (1×). The organic phase is dried on magnesium sulfate and then evaporated under reduced pressure to yield 358 mg (93%) of beige solid.

LC-MS: $t_R$=5.85 min (method a); m/z: [M+H]$^+$=372

Compound 32: 4-(2-(cyanomethyl)thiazol-4-yl)-N-(3,3,3-trifluoropropyl)benzene sulfonamide

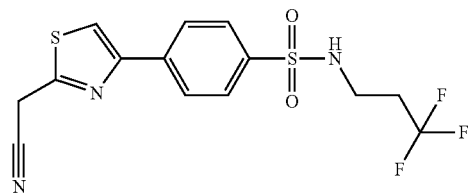 [SMILES: N#CCc1nc(-c2ccc(S(=O)(=O)NCCC(F)(F)F)cc2)cs1]

105.4 mg (1.1 eq.) 2-cyanothioacetamide are added to a solution of 358 mg (1 eq.) 4-(2-bromoacetyl)-N-isopentyl benzene sulfonamide (31) in 25 mL THF on a molecular sieve. The reaction mixture is left under THF reflux during 24 h. An additional 0.1 eq 2-cyanothioacetamide are added, the medium is agitated for a further 1 h at 70° C. The THF is then evaporated under reduced pressure and then the solid thus obtained is taken over in the ethyl acetate and washed in brine (2×). The organic phase is dried on magnesium sulfate and then evaporated under reduced pressure. The olive-green oil thus obtained is agitated for 1 h at AT in methanol in the presence of MgSO$_4$ and activated charcoal. The medium is filtrated to yield a cloudy yellow filtrate. The methanol is evaporated under reduced pressure. The yellow solid is taken over in the ethanol and then filtrated again to yield 270 mg (75%) of yellow solid used as is in the following steps.

LC-MS: $t_R$=5.35 min (method a); m/z: [M+H]$^+$=376

Compound 33: 2-(4-(4-(N-(3,3,3-trifluoropropyl) sulfamoyl)phenyl)thiazol-2-yl)methyl acetate

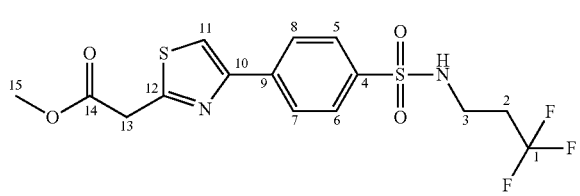

1.05 mL (36 eq.) anhydrous methanol, 1.60 mL (18 eq.) TMSCl and 270 mg (1 eq.) 4-(2-(cyanomethyl)thiazol-4-yl)-N-(3,3,3-trifluoropropyl)benzene sulfonamide (32) are successively added at AT in a dry flask and under argon. The mixture is then agitated at 50° C. during 15 h and then left to return to AT. 1 mL water is then added and the pH is neutralized by means of an aqueous solution saturated with NaHCO$_3$. The mixture is agitated 10 min at AT and then extracted using ethyl acetate. The organic phases are washed in brine (2×), dried on magnesium sulfate and evaporated. The orange solid thus obtained is purified on a pre-packed silica column (EtOAc 1:9 petroleum ether→EtOAc 3:7 petroleum ether) to yield 137 mg (47%) of pale beige powder.

LC-MS: $t_R$=6.22 min (method b); m/z: [M+H]$^+$=409

NMR $^1$H (CDCl$_3$, 300 MHz): δ ppm=8.06 (d, 2H, $^3$J=8.40 Hz, 7+8); 7.91 (d, 2H, $^3$J=8.40 Hz, 5+6); 7.64 (s, 11); 4.81 (t, 1H, $^3$J=6.50 Hz, NH); 4.17 (s, 2H, 13); 3.81 (s, 3H, 15); 3.25 (q, 2H, $^3$J=6.70 Hz, 3); 2.37 (qt, 2H, $^3$J$_{2-1}$=10.50 Hz, $^3$J$_{2-3}$=6.80 Hz, 2)

NMR $^{13}$C (CDCl$_3$, 75 MHz): δ ppm=169.4 (14); 162.3 (12); 153.0 (10); 138.7 (4 or 9); 138.5 (4 or 9); 127.6 (5+6); 127.0 (7+8); 125.9 (q, $^1$J$_{C-F}$=276.7 Hz, 1); 116.6 (11); 52.7 (15); 38.6 (13); 36.7 (3); 34.5 (q, $^2$J$_{C-F}$=29.0 Hz, 2).

Compound 34: 2-(4-(4-(N-(3,3,3-trifluoropropyl) sulfamoyl)phenyl)thiazol-2-yl)ethyl acetate

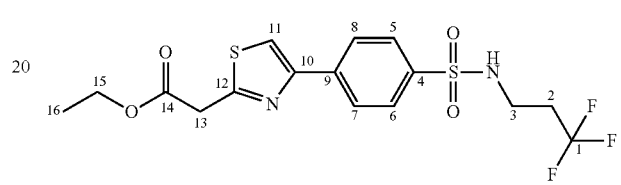

186 µL (12 eq.) absolute ethanol, 195 µL TMSCl (6 eq.) and 100 mg (1 eq.) 4-(2-(cyanonnethyl)thiazol-4-yl)-N-(3,3,3-trifluoropropyl)benzene sulfonamide (32) are successively added at AT in a dry flask and under argon. The mixture is then agitated at 30° C. during 48 h. The nitrile is then converted to 67% in the desired ester and to 33% in carboxylic acid (HPLC analysis, 215 nm). 99 µL (3 eq.) SOCl$_2$ are then added in 466 µL (30 eq.) absolute ethanol. The reaction medium is agitated at 40° C. during 48 h and then left to return to AT 1 mL water is then added and the pH is neutralized by means of an aqueous solution saturated with NaHCO$_3$. The mixture is agitated 10 min at AT and then extracted using ethyl acetate. The organic phases are washed in brine, dried on magnesium sulfate and evaporated. The orange solid thus obtained is purified on a pre-packed silica column (AcOEt 1:9 petroleum ether→AcOEt 3:7 petroleum ether) to yield 66 mg (59%) of pale beige powder.

LC-MS: $t_R$=6.22 min (method b); m/z: [M+H]$^+$=423

NMR $^1$H (CDCl$_3$ 300 MHz): δ ppm=8.04 (d, 2H, $^3$J=8.70 Hz, 7+8); 7.90 (d, 2H, $^3$J=8.70 Hz, 5+6); 7.63 (s, 1H, 11); 5.11 (t, 1H, $^3$J=6.50 Hz, NH); 4.27 (q, 2H, $^3$J=7.20 Hz, 3); 4.14 (s, 2H, 13); 3.24 (q, 2H, $^3$J=6.80 Hz, 15); 2.36 (qt, 2H, $^3$J$_{2-1}$=10.60 Hz, $^3$J$_{2-3}$=6.90 Hz, 2); 1.33 (t, 3H, $^3$J=7.10 Hz, 16)

NMR $^{13}$C (CDCl$_3$, 75 MHz): δ ppm=169.0 (14); 162.6 (12); 153.0 (10); 138.8 (4); 128.6 (9); 127.7 (5+6); 127.1 (7+8); 126 (q, $^1$J$_{C-F}$=276 Hz, 1); 116.7 (11); 61.9 (15); 39.0 (13); 36.7 (3); 34.6 (q, $^2$J$_{C-F}$=28.3 Hz, 2); 14.2 (16)

Compound 35: 2-(4-(4-(N-(3,3,3-trifluoropropyl) sulfamoyl)phenyl)thiazol-2-yl) isopropyl acetate

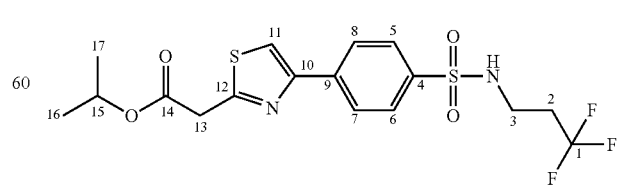

244 µL (12 eq.) anhydrous isopropanol, 195 µL (6 eq.) TMSCl and 100 mg (1 eq.) 4-(2-(cyanomethyl)thiazol-4- yl)-N-(3,3,3-trifluoropropyl)benzene sulfonamide (32) are successively added at AT in a dry flask and under argon. The mixture is then agitated at 30° C. during 48 h. 197 μL (6 eq.) SOCl$_2$ are then added in 466 μL (30 eq.) anhydrous isopropanol. The reaction medium is agitated at 40° C. during 48 h and then left to return to AT. 1 mL water is then added and the pH is neutralized by means of an aqueous solution saturated with NaHCO$_3$. The mixture is agitated for 10 min at AT and then extracted using ethyl acetate. The organic phases are washed in brine (2×), dried on magnesium sulfate and evaporated. The orange solid thus obtained is purified on a pre-packed silica column (AcOEt 1:9 petroleum ether→AcOEt 3:7 petroleum ether). The product is purified a second time on HPLC to yield 29 mg (25%) of pale beige powder.

LC-MS: $t_R$=6.50 min (method b); m/z: [M+H]$^+$=437

NMR $^1$H(CDCl$_3$, 300 MHz): δ ppm=8.04 (d, 2H, $^3$J=8.70 Hz, 7+8); 7.90 (d, 2H, $^3$J=8.70 Hz, 5+6); 7.63 (s, 1H, 11); 5.06-5.18 (m, 15+NH); 4.11 (s, 2H, 13); 3.23 (q, 2H, $^3$J=6.8 Hz, 3); 2.36 (tq, 2H, $^3$J$_{2-1}$=10.60 Hz, $^3$J$_{2-3}$=6.90 Hz, 2); 1.30 (d, 6H, $^3$J=6.30 Hz, 16+17)

NMR $^{13}$C (CDCl$_3$, 75 MHz): δ ppm=168.6 (14); 162.8 (12); 152.9 (10); 138.8 (4 or 9); 138.5 (4 or 9); 127.7 (5+6); 127.1 (7+8); 125.9 (q, $^1$J$_{C-F}$=277.5 Hz, 1); 116.7 (11); 69.7 (15); 39.4 (13); 36.7 (3); 34.5 (q, $^2$J$_{C-F}$=28.3 Hz, 2); 21.8 (16+17)

Scheme 5:

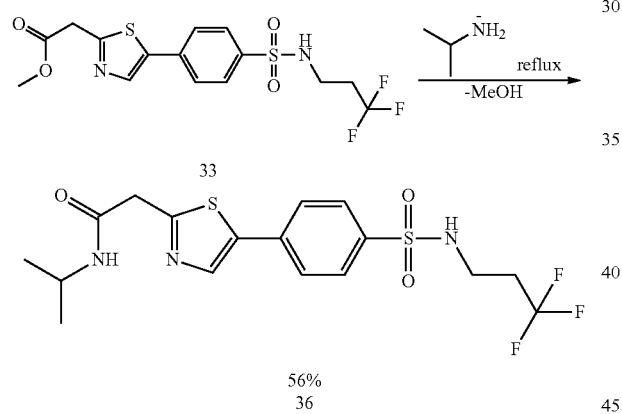

Compound 36: N-isopropyl-2-(4-(4-(N-(3,3,3-trifluoropropyl)sulfamoyl)phenyl) thiazol-2-yl)acetamide

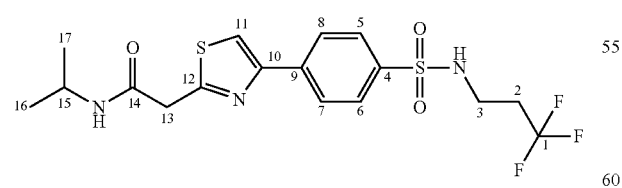

54 mg 2-(4-(4-(N-(3,3,3-trifluoropropyl)sulfamoyl)phenyl)thiazol-2-yl) methyl acetate (33) and 1 mL isopropylamine are introduced in a 5 mL dry flask. The mixture is heated under isopropylamine reflux during 5 h. An additional 0.5 mL isopropylamine are added and the mixture is heated under reflux for a further 4 h. The isopropylamine is then evaporated under reduced pressure. The product is taken over in ethyl acetate and washed in brine (2×). The organic phase is dried on magnesium sulfate and then evaporated under reduced pressure. The orange solid thus obtained is purified on a pre-packed silica column (DCM 98:2 MeOH) to yield 32 mg (56%) of beige powder.

LC-MS: $t_R$=5.57 min (method b); m/z: [M+H]$^+$=436

NMR $^1$H DMSO-d$_6$ 300 MHz): δ ppm=8.22 (s, 1H, 11); 8.14 (d, 2H, $^3$J=8.51 Hz, 7+8); 7.89 (d, 2H, $^3$J=8.51 Hz, 5+6); 4.07 (s, 2H, 13); 3.92-3.79 (m, 1H, 15); 2.99 (t, 2H, $^3$J=6.91 Hz, 3); 2.43 (qt, 2H, $^3$J$_{2-1}$=11.21 Hz, $^3$J$_{2-3}$=6.96 Hz, 2); 1.08 (d, 6H, $^3$J=6.58 Hz)

Scheme 6:

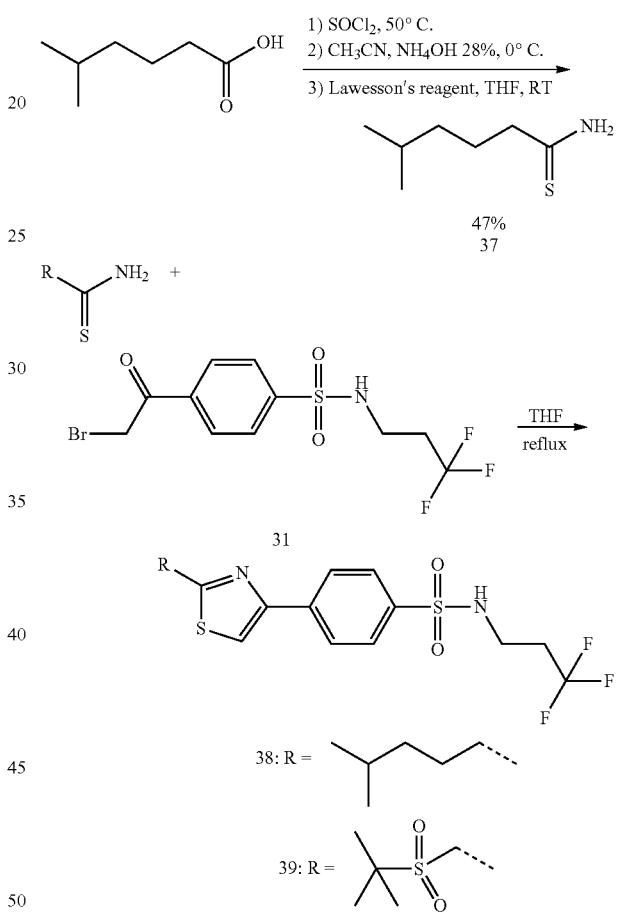

Compound 37: 5-methylhexanethioamide

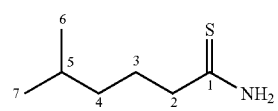

2 mL 5-methylhexanoic acid and 5 mL thionyl chloride are introduced in a 25 mL flask. The mixture is heated at 50° C. during 1 h and then the thionyl chloride is evaporated under reduced pressure. A mixture CH$_3$CN (5 mL) (10 mL) NH$_4$OH (28%) is then added at 0° C. The solution is then agitated during 15 min at 0° C. The product is extracted using ethyl acetate. The organic phases are collected, dried on magnesium sulfate and then evaporated under reduced pressure to yield a white powder.

2.9 g (0.5 eq.) Lawesson reagent and 50 mL anhydrous THF are then added to the product. The solution is agitated at AT during 4 h. The THF is evaporated under reduced pressure and the product is purified on a pre-packed silica column (Cyclohexane 85:15 AcOEt→Cyclohexane 80:20 AcOEt) to yield 950 mg (47%) of transparent oil that then crystallizes.

LC-MS: $t_R$=3.03 min (method c); m/z: [M+H]$^+$=146

NMR 1H (CDCl$_3$ 300 MHz): δ ppm=8.35+7.46 (NH$_2$); 2.58 (t, 2H, $^3$J=7.60 Hz, 2); 1.64-1.74 (m, 2H, 3 or 4); 1.50 (sp, 1H, $^3$J=6.70 Hz, 5); 1.12-1.21 (m, 2H, 3 or 4); 0.82 (d, 6H, $^3$J=6.60 Hz, 6+7)

Compound 38: 4-(2-(4-methylpentyl)thiazol-4-yl)-N-(3,3,3-trifluoropropyl)benzene sulfonamide

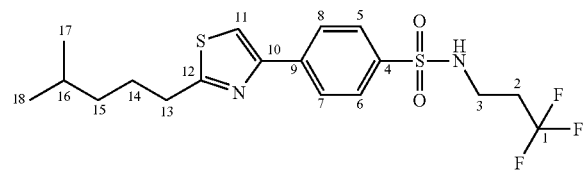

232 mg (1 eq.) 4-(2-bromoacetyl)-N-isopentyl benzene sulfonamide (31) are added to a solution of 90 mg (1 eq.) 5-methylhexanethioamide (37) in 20 mL anhydrous THF. The reaction medium is heated under reflux during 3 h. The THF is then evaporated under reduced pressure. The product is taken over in the ethyl acetate, washed in water (2×) and then in brine (1×). The organic phase is dried on magnesium sulfate and then evaporated under reduced pressure. The yellow oil thus obtained is purified on a pre-packed silica column (Cyclohexane 9:1 AcOEt 4 Cyclohexane 8:2 AcOEt) to yield 60 mg (24%) of beige powder.

LC-MS: $t_R$=7.60 min (method d); m/z: [M+H]$^+$=421

NMR $^1$H (CDCl$_3$ 300 MHz): δ ppm=8.07 (d, 2H, $^3$J=8.60 Hz, 5+6); 7.91 (d, 2H, $^3$J=8.60 Hz, 7+8); 7.51 (s, 1H, 11); 4.89 (t, 1H, $^3$J=6.50 Hz, NH); 3.26 (q, 2H, $^3$J=6.70 Hz, 3); 3.06 (t, 2H, $^3$J=7.70 Hz, 13); 2.37 (qt, 2H, $^3$J$_{2-1}$=10.70 Hz $^3$J$_{2-3}$=6.70 Hz, 2); 1.85 (q, 2H, $^3$J=7.80 Hz, 14); 1.63 (n, 1H, $^3$J=6.70 Hz, 16); 1.30-1.38 (m, 4H, 15+fat); 0.92 (d, 6H, $^3$J=6.6 Hz, 17+18)

NMR $^{13}$C (CDCl$_3$ 75 MHz): δ ppm=172.6 (12); 153.0 (10); 139.2 (9); 138.3 (4); 127.7 (7+8); 127.2 (5+6); 120.5-131.5 (q, $^1$J$_{C-F}$=277.2 Hz, 1); 114.9 (11); 38.5 (15); 36.8 (3); 34.6 (q, $^2$J$_{C-F}$=28.4 Hz, 2); 34.0 (13); 28.1 (14); 28.0 (16); 22.7 (17+18)

Compound 39: 4-(2-(tert-butylsulfonylmethyl)thiazol-4-yl)-N-(3,3,3-trifluoropropyl)-benzene sulfonamide

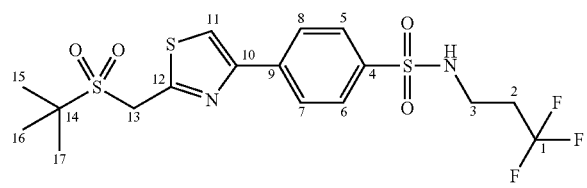

150 mg (1 eq.) 4-(2-bromoacetyl)-N-isopentyl benzene sulfonamide (31) are added to a solution of 78.3 mg (1 eq.) 2-(tert-butylsulfonyl)ethanethioamide in 7 mL anhydrous THF. The reaction medium is heated under reflux during 72 h. The THF is then evaporated under reduced pressure. The product is taken over in the ethyl acetate, washed in water and then in brine. The organic phase is dried on magnesium sulfate and then evaporated under reduced pressure. The product thus obtained is purified by HPLC to yield 119 mg (63%) of beige powder.

LC-MS: $t_R$=5.67 min (method d); m/z: [M+H]$^+$=471

NMR $^1$H DMSO-d$_6$ 300 MHz): δ ppm=8.44 (s, 1H, 11); 8.19 (d, 2H, $^3$J=8.70 Hz, 7+8); 7.94 (t, 1H, $^3$J=6.0 Hz, NH); 7.90 (d, 2H, $^3$J=8.70 Hz, 5+6); 5.09 (s, 2H, 13); 3.00 (q, 2H, $^3$J=6.60 Hz, 3); 2.44 (qt, 2H, $^3$J$_{2-1}$=11.2 Hz, $^3$J$_{2-3}$=7.0 Hz, 2); 1.38 (s, 9H, 15+16+17)

NMR $^{13}$C DMSO-d$_6$ 75 Hz: δ ppm=157.1 (12); 152.5 (10); 139.0 (4); 137.4 (9); 127.2 (5+6); 126.6 (7+8); 126.4 (q, $^1$J$_{C-F}$=277.0 Hz, 1); 120.0 (11); 60.2 (14); 50.3 (13); 36.03 (q, $^3$J$_{C-F}$=3.70 Hz, 3); 66.3 (q, $^2$J$_{C-F}$=27.2 Hz, 2); 22.9 (15+16+17)

Scheme 7:

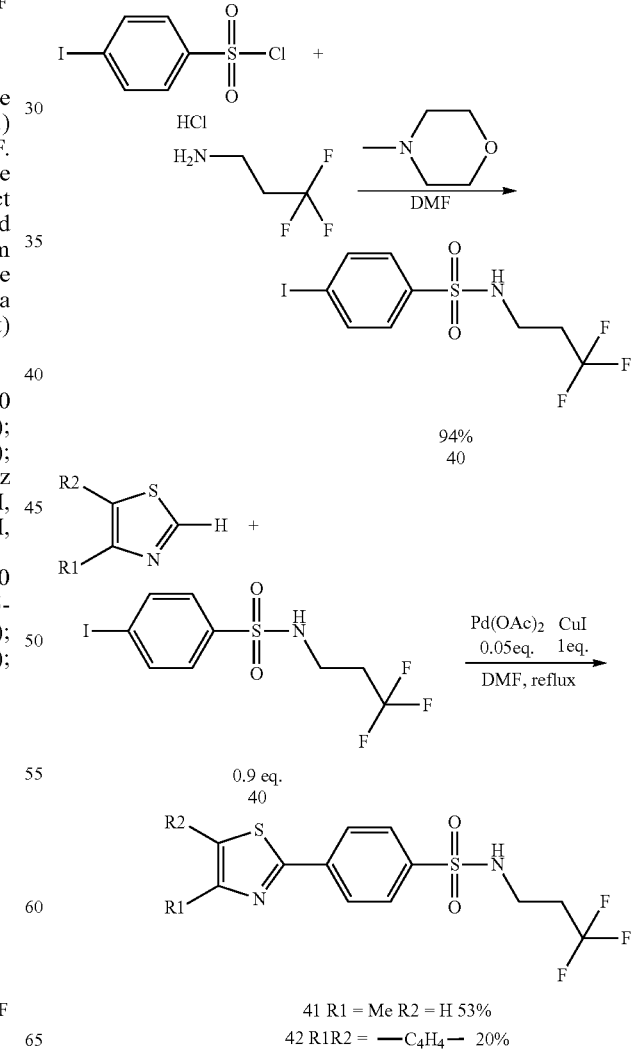

41 R1 = Me R2 = H 53%

42 R1R2 = —C$_4$H$_4$— 20%

Compound 40: 4-iodo-N-(3,3,3-trifluoropropyl)benzene sulfonamide

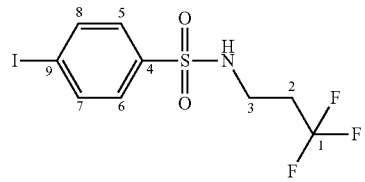

1.82 mL (5 eq.) N-methylmorpholine are added to a solution of 593.2 mg (1.2 eq.) 3,3,3-trifluoropropylamine hydrochloride in 50 mL DMF. The mixture is agitated for 5 min at AT and then 1 g (1 eq.) 4-iodobenzene sulfonic acid chloride is added. The reaction medium is agitated at AT during 2 h. The DMF is evaporated under reduced pressure and then the product is taken over in the ethyl acetate, washed in water (2×) and in brine (1×). The organic phase is dried on magnesium sulfate and then evaporated under reduced pressure to yield 1.17 g (94%) of pale yellow solid.

LC-MS: $t_R$=6.22 min (method b); m/z: [M−H]⁻=378

NMR ¹H (CD₂Cl₂, 300 MHz): δ ppm=7.96 (d, 2H, ³J=8.70 Hz, 5+6 or 7+8); 7.60 (d, 2H, ³J=8.70 Hz, 5+6 or 7+8); 4.81 (m, 1H, NH); 3.25 (q, 2H, ³J=6.70 Hz, 3); 2.43 (qt, 2H, ³J$_{2-1}$=10.60 Hz, ³J$_{2-3}$=6.80 Hz, 2)

Compound 41: 4-(4-methylthiazol-2-yl)-N-(3,3,3-trifluoropropyl)benzene sulfonamide

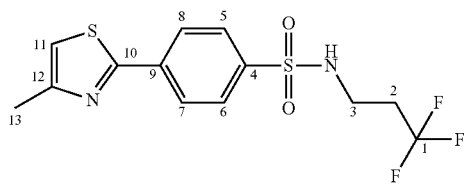

40.0 µL (1 eq.) 4-methylthiazole, 4.9 mg (0.05 eq.) palladium acetate, 83.7 mg (1 eq.) copper iodide and 150 mg (0.9 eq.) 4-iodo-N-(3,3,3-trifluoropropyl)-benzene sulfonamide (40) are placed successively in a schlenk under an argon flow. 1.5 mL anhydrous DMF are added via a cannula under argon at ambient temperature. The schlenk is drawn three times under vacuum and filled successively with argon. The reaction mixture is agitated at 140° C. under argon during 48 h. The reaction medium is diluted at AT with 2 mL of a mixture of ethyl acetate and of an aqueous solution saturated with NH₄Cl (1:1 by volume). The medium is then filtrated and the solid washed using ethyl acetate. The organic phase is washed in brine (2×), dried on magnesium sulfate, filtrated on celite and then evaporated under reduced pressure. The product is then purified on a pre-packed silica column (AcOEt 1:9 Petroleum ether→AcOEt 2:8 petroleum ether) to yield 73 mg (53%) of white powder.

LC-MS: $t_R$=6.07 min (method b); m/z: [M+H]⁺=351

NMR ¹H (CD₂Cl 300 MHz): δ ppm=8.11 (d, 2H, ³J=8.70 Hz, 7+8); 7.91 (d, 2H, ³J=8.70 Hz, 5+6); 7.04 (s, 1H, 11); 4.83 (m, 1H, NH); 3.26 (q, ³J=6.70 Hz, 3); 2.51 (s, 3H, 13); 2.39 (tq, 2H, ³J$_{2-1}$=10.60 Hz, ³J$_{2-3}$=6.80 Hz, 2)

NMR ¹³C (CD₂Cl₂ 75 MHz): δ ppm=164.8 (10); 154.4 (12); 141.0 (4); 137.0 (9); 128.0 (5+6); 127.2 (7+8); 126.85 (q, ¹J$_{C-F}$=277.1 Hz, 1); 116.9 (11); 36.4 (q, ³J$_{C-F}$=3.8 Hz, 3); 33.6 (q, ²J$_{C-F}$=27.4 Hz, 2); 17.3 (13)

Compound 42: 4-(benzo[d]thiazol-2-yl)-N-(3,3,3-trifluoropropyl)benzene sulfonamide

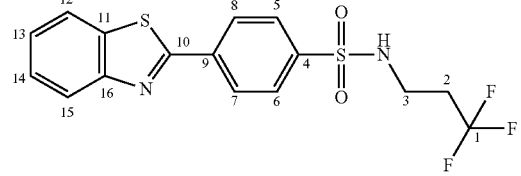

48.0 µL (1 eq.) 4-methylthiazole, 4.9 mg (0.05 eq.) palladium acetate, 83.7 mg (1 eq.) copper iodide and 150 mg (0.9 eq.) 4-iodo-N-(3,3,3-trifluoropropyl)-benzene sulfonamide (40) are successively placed in a schlenk under an argon flow. 1.5 mL anhydrous DMF are added via a cannula under argon at ambient temperature. The schlenk is drawn three times under vacuum and filled successively with argon. The reaction mixture is agitated at 140° C. under argon during 48 h. The reaction medium is diluted at AT with 2 mL of a mixture of ethyl acetate and of an aqueous solution saturated with NH₄Cl (1:1 by volume). The medium is then filtrated and the solid washed using ethyl acetate. The organic phase is washed in brine (2×), dried on magnesium sulfate, filtrated on celite and then evaporated under reduced pressure The product is then purified on a pre-packed silica column (AcOEt 1:9 petroleum ether→AcOEt 2:8 petroleum ether). The product is then recrystallized in 2 mL ethanol to yield 31 mg (20%) of transparent crystals.

LC-MS: $t_R$=6.73 min (method b); m/z: [M+H]⁺=387

NMR ¹H (DMSO-d₆, 300 MHz): δ ppm=8.34 (d, 2H, ³J=8.50 Hz, 7+8); 8.21-8.23 (m; 1H, 12 or 15); 8.09-8.14 (m, 2H, NH+12 or 15); 8.00 (d, 2H, ³J=8.50 Hz, 5+6); 7.60 (td, 1H, ³J=7.40 Hz, ⁴J=1.20 Hz, 13 or 14); 7.53 (td, 1H, ³J=7.40 Hz, ⁴J=1.20 Hz, 13 or 14); 3.04 (t, 2H, ³J=6.90 Hz, 3); 2.39 (qt, 2H, ³J$_{2-1}$=10.60 Hz, ³J$_{2-3}$=6.80 Hz, 2)

NMR ¹³C (CD₂Cl₂, 75 MHz): δ ppm=166.0 (10); 154.0 (16); 142.4 (9); 136.7 (16); 135.3 (11); 128.5 (5+6); 128.1 (7+8); 127.5 (13 or 14); 126.6 (13 or 14); 126.9 (q, ¹J$_{C-F}$=273.4 Hz, 1); 123.8 (15 or 12); 123.1 (15 or 12); 36.5 (3); 33.7 (q, ²J$_{C-F}$=27.5 Hz, 2)

Scheme 8:

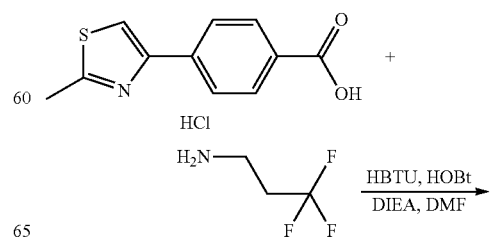

-continued

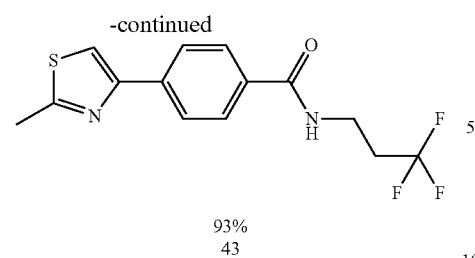

93%
43

Compound 43: 4-(2-methylthiazol-4-yl)-N-(3,3,3-trifluoropropyl)benzamide

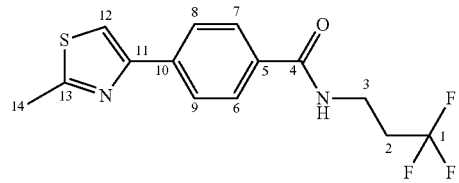

50 mg (1 eq.) 4-(2-methylthiazol-4-yl)benzoic acid, 37 mg (1.1 eq.) 3,3,3-trifluoropropylamine hydrochloride (1.1 eq), 103 mg (1.2 eq.) HBTU, 52 mg (1.5 eq.) HOBt, 118 µL (3 eq.) DIEA and 2.5 mL DMF are introduced in this particular order in a 10 mL flask. The solution is agitated during 2 h at AT. The DMF is evaporated under reduced pressure. The product is taken over in the ethyl acetate and then washed successively by means of an aqueous solution saturated with $K_2CO_3$ (2×), an aqueous solution of HCl 1N (2×), of water (1×) and of brine (1×). The organic phase is dried on magnesium sulfate and then evaporated under reduced pressure to yield 67 mg (93%) of beige powder.

LC-MS: $t_R$=3.10 min (method c); m/z; $[M+H]^+$=315

NMR $^1$H (CD$_3$OD, 300 MHz): δ ppm=7.99 (d, 2H, $^3$J=8.50 Hz, 8+9); 7.87 (d, 2H, $^3$J=8.50 Hz, 6+7); 7.76 (s, 1H, 12); 3.64 (t, 2H, $^3$J=7.00 Hz, 3); 2.76 (s, 3H, 14); 2.54 (qt, 2H, $^3J_{2-1}$=10.60 Hz, $^3J_{2-3}$=6.80 Hz, 2)

NMR $^{13}$C (CD$_3$OD, 75 MHz): δ ppm=168.4 (4); 167.1 (13); 153.6 (11); 137.4 (10); 133.1 (5); 127.4 (6+7); 126.7 (q, $^1J_{C-F}$=277.8 Hz, 1); 125.9 (8+9); 114.7 (12); 33.1 (3); 32.7 (q, $^2J_{C-F}$=27.5 Hz, 2); 17.5 (14)

Scheme 9:

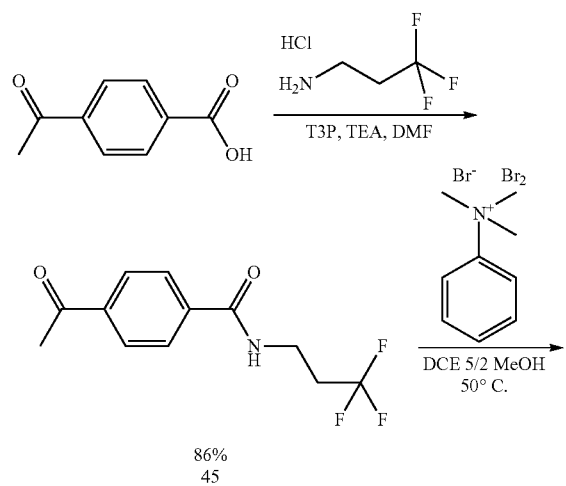

86%
45

-continued

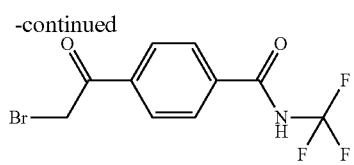

99%
46

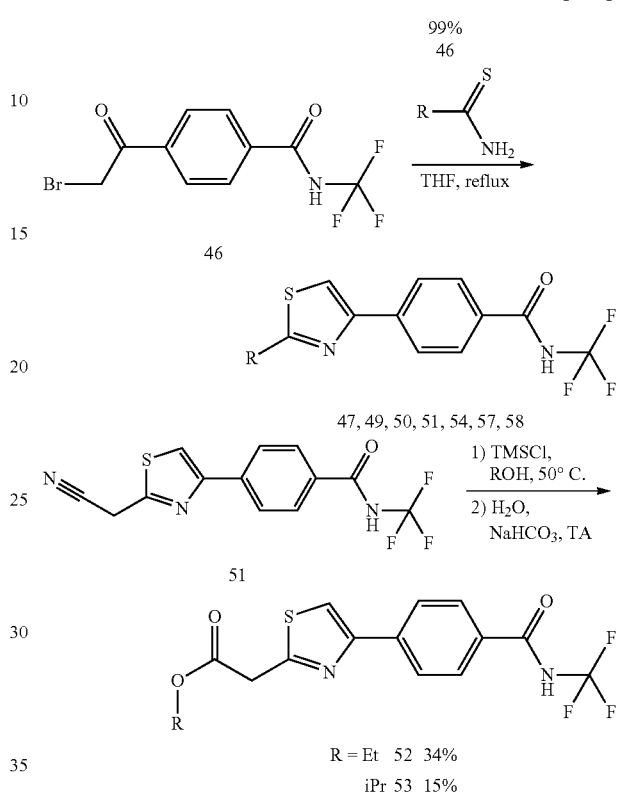

R = Et  52  34%
iPr  53  15%

Compound 45:
4-acetyl-N-(3,3,3-trifluoropropyl)benzamide

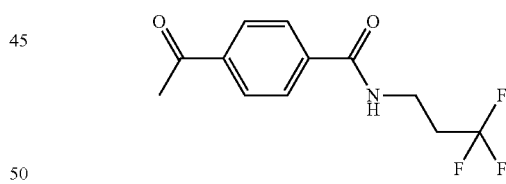

546.6 mg (1 eq.) 3,3,3-trifluoropropylamine hydrochloride are added to a solution of 600 mg (1 eq.) 4-acetylbenzoic acid, 1.66 g (1.2 eq.) HBTU, 98 mg (0.2 eq.) HOBt, and 2.53 mL (4 eq.) DIEA in 15 mL DMF. The reaction medium is then agitated during 2 h at AT. The DMF is then evaporated under reduced pressure. The orange oil thus obtained is taken over in the ethyl acetate and then washed by means of an aqueous solution of HCl 1N (2×), an aqueous solution saturated with $Na_2CO_3$ (2×) and then in brine (1×). The organic phase is dried on magnesium sulfate and then evaporated under reduced pressure. The product thus obtained is purified on a pre-packed silica column (Cyclohexane 85:15 AcOEt→80:20→70:30) to yield 837 mg (88%) of white powder.

LC-MS: $t_R$=2.70 min (method c); m/z; $[M+H]^+$=260

Compound 46: 4-(2-bromoacetyl)-N-(3,3,3-trifluoropropyl)benzamide

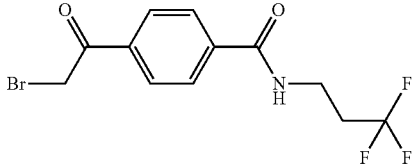 [SMILES: O=C(CBr)c1ccc(C(=O)NCCC(F)(F)F)cc1]

436.1 mg (1 eq.) trimethylphenylammonium tribromide are added to a solution of 300 mg (1 eq.) 4-acetyl-N-(3,3,3-trifluoropropyl)benzamide (45) in a mixture of 15 mL DCE and 6 mL methanol. The solution is agitated at 50° C. 43.6 mg (0.1 eq) brominating reagent are added after 1 h and 3 h of reaction. The DCE and the methanol are evaporated under reduced pressure. The product is taken over in the ethyl acetate and then washed using water (2×) and in brine (1×). The organic phase is dried on magnesium sulfate and then evaporated under reduced pressure to yield 387 mg (99%) of beige powder.

LC-MS: $t_R$=2.93 min (method c); m/z: $[M+H]^+$=340

Compound 47: 4-(2-(4-methylpentyl)thiazol-4-yl)-N-(3,3,3-trifluoropropyl)benzamide

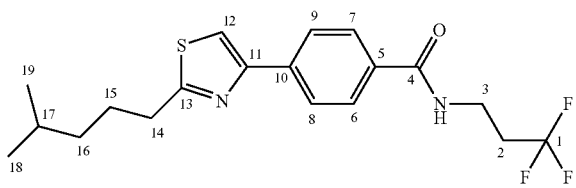

100 mg (1 eq.) 4-(2-bromoacetyl)-N-(3,3,3-trifluoropropyl)benzamide (46) are added to a solution of 43 mg (1 eq.) 5-methylhexanethioamide (37) in 10 mL anhydrous THF. The reaction medium is heated under reflux during 3 h. The THF is then evaporated under reduced pressure. The product is taken over in the ethyl acetate, washed in water (2×) and then in brine (1×). The organic phase is dried on magnesium sulfate and then evaporated under reduced pressure. The beige solid thus obtained is purified on a pre-packed silica column (Cyclohexane 9:1 AcOEt) to yield 25 mg (22%) of powder beige.

LC-MS: $t_R$=3.77 min (method c); m/z: $[M+H]^+$=385

NMR $^1$H (CD$_2$Cl$_2$, 300 MHz): δ ppm=7.99 (d, 2H, $^3$J=8.66 Hz, 8+9); 7.84 (d, 2H, $^3$J=8.66 Hz, 6+7); 7.51 (s, 1H, 12); 6.83 (t, 1H, $^3$J=5.70 Hz, NH); 3.73 (q, 2H, $^3$J=6.50 Hz, 3); 3.06 (t, 2H, $^3$J=7.77 Hz, 14); 2.53 (qt, 2H, $^3$J$_{2-1}$=10.92 Hz $^3$J$_{2-3}$=6.78 Hz, 2); 1.87 (qn, 2H, $^3$J=7.85 Hz, 15); 1.66 (n, 1H, $^3$J=6.65 Hz, 17); 1.36 (q, 2H, $^3$J=7.51 Hz, 16); 0.95; (d, 6H, $^3$J=6.63 Hz, 18+19)

Compound 48: 3-methylbutanethioamide

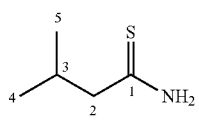

1.01 g (0.5 eq.) Lawesson reagent and 16 mL anhydrous THF are added to 505.8 mg (1 eq.) isovaleramide. The solution is agitated at AT during 4 h and then THF is evaporated under reduced pressure. The product is taken over in the diisopropylic ether and then filtrated. The filtrate is then purified on a pre-packed silica column (DCM 100%) to yield 396 mg (70%) of transparent oil that then crystallizes.

LC-MS: $t_R$=1.92 min (method c); m/z: $[M+H]^+$=118

NMR $^1$H (CDCl$_3$, 300 MHz): δ ppm=7.65 (br s, 1H, NH); 6.85 (br s, 1H, NH); 2.52 (d, 2H, $^3$J=7.28 Hz, 2); 2.25 (n, 1H, $^3$J=6.95 Hz, 3); 1.00 (d, 6H, $^3$J=6.59 Hz, 4+5)

Compound 49: 4-(2-isobutylthiazol-4-yl)-N-(3,3,3-trifluoropropyl)benzamide

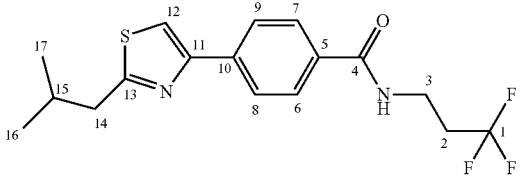 [SMILES: CC(C)Cc1nc(-c2ccc(C(=O)NCCC(F)(F)F)cc2)cs1]

100 mg (1 eq.) 4-(2-bromoacetyl)-N-(3,3,3-trifluoropropyl)benzamide (46) are added to a solution of 34.7 mg (1 eq.) 3-methylbutanethioamide (48) in 6 mL anhydrous THF. The reaction medium is heated under reflux during one night. 3.5 mg (0.1 eq) thioamide are added and the solution is agitated for a further 1 h under reflux. The THF is then evaporated under reduced pressure. The product is taken over in the ethyl acetate, washed in water (2×) and then in brine (1×). The organic phase is dried on magnesium sulfate and then evaporated under reduced pressure. The residue is purified using preparative HPLC to yield 78 mg (74%) of beige powder.

LC-MS: $t_R$=3.17 min (method c); m/z: $[M+H]^+$=357

NMR $^1$H (CD$_2$Cl$_2$, 300 MHz): δ ppm=8.01 (d, 2H, $^3$J=8.60 Hz, 8+9); 7.82 (d, 2H, $^3$J=8.60 Hz, 6+7); 7.53 (s, 1H, 12); 6.47 (br s, 1H, NH); 3.74 (t, 2H, $^3$J=6.50 Hz, 3); 2.95 (d, 2H, $^3$J=6.70 Hz, 14); 2.53 (qt, 2H, $^3$J$_{2-1}$=10.80 Hz, $^3$J$_{2-3}$=6.50 Hz, 2); 2.19 (n, 1H, $^3$J=6.70 Hz, 15); 1.05 (d, 6H, $^3$J=6.60 Hz, 16+17)

NMR $^{13}$C(CD$_2$Cl$_2$, 75 MHz): δ ppm=171.0 (13); 167.4 (4); 154.0 (11); 138.2 (10); 133.6 (5); 127.8 (6+7); 127.1 (q, $^1$J$_{C-F}$=277.8 Hz, 1); 126.7 (8+9); 114.2 (12); 42.8 (14); 34.0 (q, $^2$J$_{C-F}$=27.5 Hz, 2); 33.8 (3); 30.2 (15); 22.4 (16+17)

Compound 50: 4-(2-(tert-butylsulfonylmethyl)thiazol-4-yl)-N-(3,3,3-trifluoropropyl)-benzamide

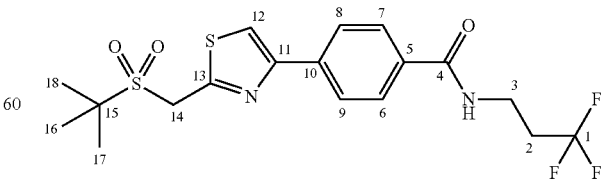

10 mg (1 eq.) 4-(2-bromoacetyl)-N-(3,3,3-trifluoropropyl)benzamide (46) are added to a solution of 57.8 mg (1 eq.) 2-(tert-butylsulfonyl)ethanethioamide in 6 mL anhydrous THF. The reaction medium is agitated and heated under reflux during one night. An additional 11.7 mg (0.2 eq.) thioamide are added and the mixture is agitated for 2 h under reflux. The THF is then evaporated under reduced pressure. The product is taken over in the ethyl acetate, washed in water (2×) and then in brine (1×). The organic phase is dried and then evaporated under reduced pressure. The residue is purified on the pre-packed silica column (Cyclohexane 85:15 Isopropanol→Cyclohexane 1:1 Isopropanol) to yield 98 mg (76%) of white powder.

LC-MS: $t_R$=5.23 min (method c); m/z: [M+H]$^+$=435

NMR $^1$H (DMSO-d$_6$, 300 MHz): δ ppm=8.76 (t, 1H, $^3J$=5.60 Hz, NH); 8.37 (s, 1H, 12); 8.08 (d, 2H, $^3J$=8.40 Hz, 8+9); 7.93 (d, 2H, $^3J$=8.40 Hz, 6+7); 5.09 (s, 2H, 14); 3.52 (q, 2H, $^3J$=6.50 Hz, 3); 2.57 (qt, 2H, $^3J_{2-1}$=10.94 Hz, =6.62 Hz, 2); 1.39 (s, 9H, 16+17+18)

NMR $^{13}$C (DMSO-d$_6$, 75 MHz): δ ppm=166.3 (4); 157.2 (13); 153.7 (11); 136.8 (5); 133.9 (10); 128.3 (6+7); 127.5 (q, $^1J_{C-F}$=267 Hz, 1); 126.3 (8+9); 119.3 (12); 60.6 (15); 50.8 (14); 33.3 (q, $^3J_{C-F}$=3.5 Hz, 3); 32.9 (q, $^2J_{C-F}$=27.0 Hz, 2); 23.4 (16+17+18)

Compound 51: 4-(2-(cyanomethyl)thiazol-4-yl)-N-(3,3,3-trifluoropropyl)benzamide

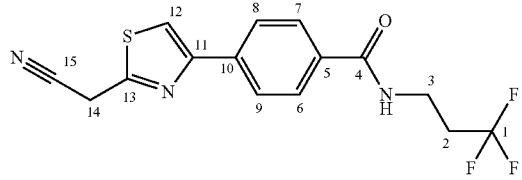

107 mg (1.2 eq.) 2-cyanothioacetamide are added to a solution of 300 mg (1 eq.) 4-(2-bromoacetyl)-N-(3,3,3-trifluoropropyl)benzamide (46) in 25 mL THF. The medium is agitated during 24 h under reflux. The THF is then evaporated under reduced pressure. The residue is taken over in the ethyl acetate and then washed in brine (2×). The organic phase is dried on magnesium sulfate and then evaporated under reduced pressure to yield 302 mg of orange solid. The raw product brut is thus used in the following reaction.$ LC-MS: $t_R$=2.96 min (method c); m/z: [M−H]$^-$=296

Compound 52: 2-(4-(4-(3,3,3-trifluoropropylcarbamoyl)phenyl)thiazol-2-yl)ethyl acetate

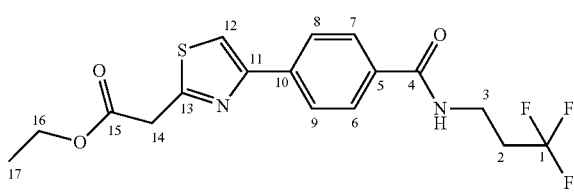 [SMILES: CCOC(=O)Cc1nc(-c2ccc(C(=O)NCCC(F)(F)F)cc2)cs1]

150 mg (1 eq.) 4-(2-bromoacetyl)-N-(3,3,3-trifluoropropyl)benzamide (46) are added to a solution of 44.4 mg (1 eq.) 2-cyanoethanethioamide in 10 mL THF. The mixture is agitated during 15 h under reflux. The THF is evaporated under reduced pressure and the residue thus obtained is used as is. Under argon, 515 μL (20 eq.) absolute ethanol and 545 μL (10 eq.) TMSCl are successively added at AT in a dry flask. The mixture is then agitated at 40° C. during 2 h. 200 μL SOCl$_2$ are then added in 1 mL absolute ethanol. The reaction medium is agitated at 40° C. during 2 h and then left to return to AT. 1 mL water is then added and the pH is neutralized by means of an aqueous solution saturated with NaHCO$_3$. The mixture is agitated for 15 min at AT and then extracted using ethyl acetate. The organic phases are washed in brine (2×), dried on magnesium sulfate and evaporated. The orange solid thus obtained is recrystallized in 2 mL absolute ethanol to yield 58 mg (34%) of light brown crystals.

LC-MS: $t_R$=2.77 min (method c); m/z: [M+H]$^+$=387

NMR $^1$H (CD$_2$Cl$_2$, 300 MHz): δ ppm=8.01 (d, 2H, $^3J$=8.50 Hz, 8+9); 7.83 (d, 2H, $^3J$=8.50 Hz, 6+7); 7.65 (s, 1H, 12); 6.47 (br s, 1H, NH); 4.26 (q, $^3J$=7.10 Hz, 16); 4.14 (s, 2H, 14); 3.73 (q, 2H, $^3J$=6.40 Hz, 3); 2.53 (qt, 2H, $^3J_{2-1}$=10.9 Hz, $^3J_{2-3}$=6.60 Hz, 2); 1.32 (t, 3H, $^3J$=7.10 Hz, 17)

Compound 53: 2-(4-(4-(3,3,3-trifluoropropylcarbamoyl)phenyl)thiazol-2-yl(isopropyl acetate

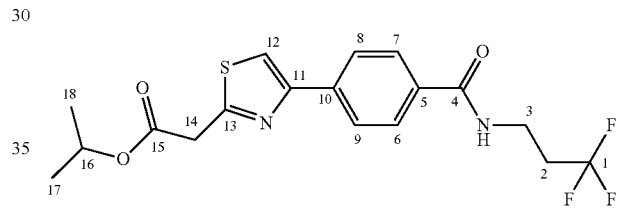

Under argon, 3.23 mL (48 eq.) isopropanol, 2.66 mL (24 eq.) TMSCl and 300 mg (1 eq.) 4-(2-(cyanomethyl)thiazol-4-yl)-N-(3,3,3-trifluoropropyl)benzamide (51) are successively added at AT in a dry flask. The solution is agitated during 10 min at AT and then 16 μL (1 eq.) water are added. The mixture is then agitated at 40° C. during one night. The pH is neutralized by means of an aqueous solution saturated with NaHCO$_3$. The mixture is agitated 15 min at AT and then extracted using ethyl acetate. The organic phases are washed in brine (2×), dried on magnesium sulfate and evaporated. The residue thus obtained is then purified on a pre-packed silica column (AcOEt 3:7 Cyclohexane) to yield 51 mg (15%) of white solid.

LC-MS: $t_R$=5.87 min (method d); m/z: [M+H]$^+$=387

NMR $^1$H (CDCl$_3$ 300 MHz): δ ppm=7.99 (d, 2H, $^3J$=8.60 Hz, 8+9); 7.83 (d, 2H, $^3J$=8.60 Hz, 6+7); 7.58 (s, 1H, 12); 6.44 (m, 1H, NH); 5.14 (sp, 1H, $^3J$=6.30 Hz, 16); 4.13 (s, 2H, 14); 3.77 (q, 2H, $^3J$=6.30 Hz, 3); 2.52 (tq, 2H, $^3J_{2-1}$=10.8 Hz, $^3J_{2-3}$=6.30 Hz, 2); 1.32 (d, 6H, $^3J$=6.20 Hz, 17+18)

NMR $^{13}$C (CD$_2$Cl$_2$, 75 MHz): δ ppm=168.9 (4); 167.4 (13); 163.0 (15); 154.0 (11); 137.9 (6); 133.9 (5); 127.9 (6+7); 127.3 (q, $^1J_{C-F}$=277.0 Hz, 1); 126.8 (8+9); 116.1 (12); 69.8 (16); 39.8 (14); 34.1 (q, $^2J_{C-F}$=27.5 Hz, 2); 33.9 (3); 22.0 (17+18)

NMR $^{19}$F (CDCl$_3$, 282.4 MHz): δ ppm=−64.95 (t, $^3J$=10.8 Hz)

Compound 57: 4-(2-(pyridin-4-yl)thiazol-4-yl)-N-(3,3,3-trifluoropropyl)benzamide

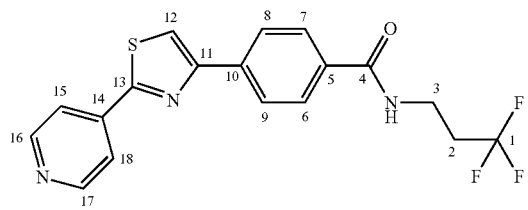

32.7 mg (1 eq.) thioisonicotinamide are added to a solution of 100 mg (1 eq.) 4-(2-bromoacetyl)-N-(3,3,3-trifluoropropyl)benzamide (46) in 6 mL THF. The mixture is agitated during one night under reflux. The formed precipitate is filtrated and then washed using di-ethylic ether. The orange solid thus obtained is then taken over using ethyl acetate in a separating funnel, washed with a solution saturated with $K_2CO_3$ and then with water (2×) and in brine (1×). The organic phase is dried on magnesium sulfate and then evaporated under reduced pressure. The residue is purified on a pre-packed silica column (Cyclohexane 8:2 Isopropanol) to yield 59 mg (66%) of yellow solid.

LC-MS: $t_R$=2.32 min (method c); m/z: [M+H]$^+$=378

NMR $^1$H (CD$_3$OD, 300 MHz): δ ppm=8.70 (m, 2H, 16+17); 8.20 (s, 1H, 12); 8.18 (d, 2H, $^3$J=8.80 Hz, 8+9); 8.08 (m, 2H, 15+18); 7.94 (d, 2H, $^3$J=8.80 Hz, 6+7); 3.67 (t, 2H, $^3$J=7.00 Hz, 3); 2.57 (qt, 2H, $^3$J$_{2-1}$=11.0 Hz, $^3$J$_{2-3}$=7.00 Hz, 2)

NMR $^{13}$C (CD$_3$OD, 75 MHz): δ ppm=168.5 (4); 164.7 (13); 155.9 (11); 149.9 (16+17); 141.2 (14); 137.1 (5); 133.7 (10); 127.5 (6+7); 126.6 (q, $^1$J$_{C-F}$=278.1 Hz, 1); 126.2 (8+9); 120.6 (15+48); 117.2 (12); 33.1 (q, $^3$J$_{C-F}$=3.3 Hz, 3); 32.7 (q, $^2$J$_{C-F}$=27.8 Hz)

Compound 58: 4-(2-(2-ethylpyridin-4-yl)thiazol-4-yl)-N-(3,3,3-trifluoropropyl)benzamide

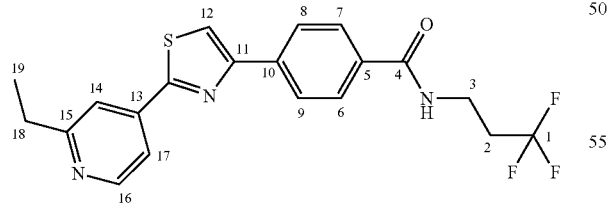

45 mg (1.1 eq.) ethionamide are added to a solution of 100 mg (1 eq.) 4-(2-bromoacetyl)-N-(3,3,3-trifluoropropyl)benzamide (46) in 10 mL THF. The mixture is agitated under reflux during 24 h. The formed precipitate is filtrated and then washed using a solution of diethyl ether. The yellow solid thus obtained is then taken over in the ethyl acetate in a separating funnel, washed with a solution saturated with $K_2CO_3$ and then using water (2×) and in brine (1×). The organic phase is dried on magnesium sulfate and then evaporated under reduced pressure to yield 75 mg (63%) of yellow solid.

LCMS: $t_R$=3.12 min (method c); (m/z); [M+H]$^+$=406

NMR $^1$H (CDCl$_3$, 300 MHz): δ ppm=8.66 (d, 1H, $^3$J=5.30 Hz, 16); 8.09 (d, 2H, $^3$J=8.50 Hz, 8+9); 7.86 (d, 2H, $^3$J=8.5 Hz, 6+7); 7.78 (s, 1H, 12); 7.69 (m, 2H, 15+17); 6.45 (m, 1H, NH); 3.77 (q, 2H, $^3$J=6.30 Hz, 3); 2.94 (q, 2H, $^3$J=7.60 Hz, 19); 2.52 (qt, 2H, $^3$J$_{2-1}$=10.80 Hz, $^3$J$_{2-3}$=6.40 Hz, 2); 1.40 (t, 3H, $^3$J=7.60 Hz, 20)

NMR $^{13}$C (CD$_2$Cl$_2$, 75 MHz): δ ppm=167.5 (4); 166.5 (13); 165.4 (18); 156.1 (16); 150.6 (16); 140.9 (14); 137.6 (10); 134.4 (5); 128.1 (q, $^1$J$_{C-F}$=276.9 Hz, 1); 128.0 (6+7); 127.0 (8+9); 119.1 (17); 118.2 (15); 116.4 (12); 34.26 (q, $^2$J$_{C-F}$=27.7 Hz, 2); 34.1 (3); 32.0 (19); 14.2 (20)

Scheme 9:

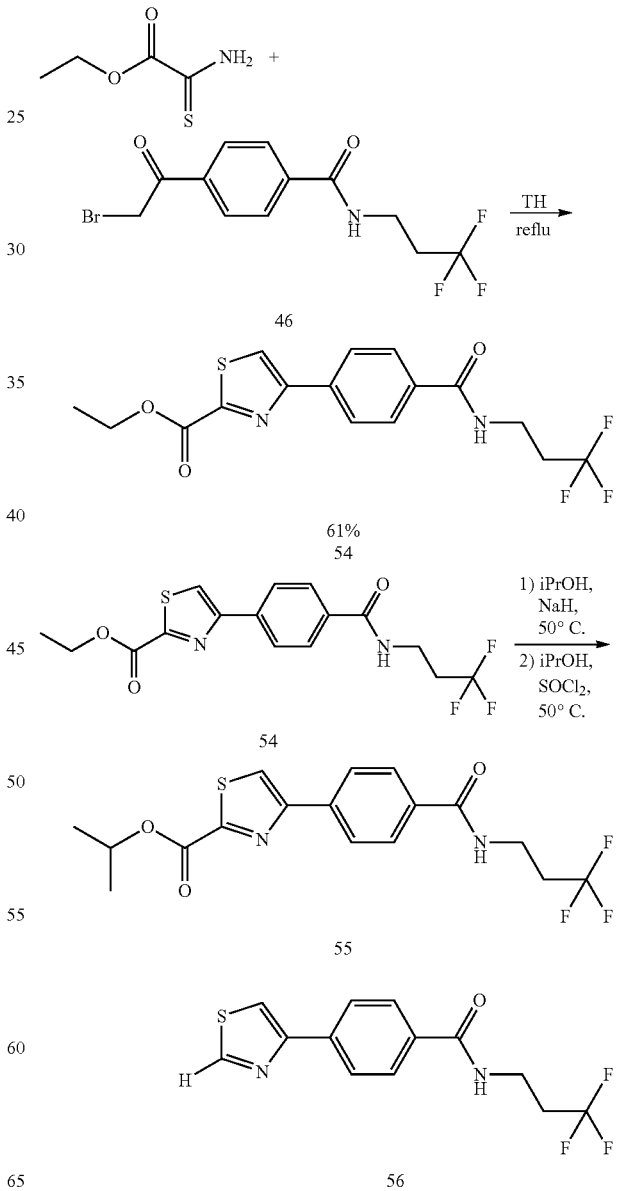

Compound 54: 4-(4-(3,3,3-trifluoropropylcarbamoyl)phenyl)thiazole-2-ethyl carboxylate

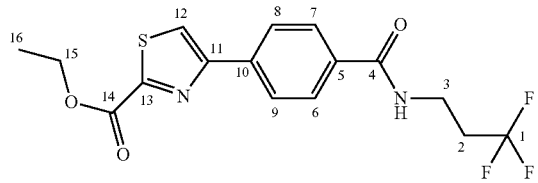

150 mg (1 eq.) 4-(2-bromoacetyl)-N-(3,3,3-trifluoropyl)benzamide (46), 71 mg (1.2 eq.) ethyl thiooxamate and 15 mL THF are introduced in a 50 mL flask. The mixture is heated under reflux during 24 h. 11.5 mg (0.2 eq) thioamide are added and the solution is again agitated during 24 h under reflux. 350 mg (3 eq.) PS-Tos-NHNH$_2$ resin are added and the reaction medium is agitated at AT during one night. The solution is then filtrated and the THF is then evaporated under reduced pressure. The residue is taken over in the ethyl acetate and then washed by means of an aqueous solution saturated with K$_2$CO$_3$ (2×) and in brine (1×). The organic phase is dried on magnesium sulfate and then concentrated under reduced pressure. The residue thus obtained is purified on a pre-packed silica column (Cyclohexane 8:2 AcOEt→Cyclohexane 7:3 AcOEt) to yield 100.1 mg (61%) of powder beige.

LC-MS: $t_R$=3.22 min (method c); m/z: [M+H]$^+$=373

NMR $^1$H (CDCl$_3$ 300 MHz): δ ppm=8.05 (d, 2H, $^3$J=8.60 Hz); 7.81-7.85 (m, 3H, 6+7+12); 6.44 (m, 1H, $^3$J=5.90 Hz, NH); 4.53 (q, 2H, $^3$J=7.10 Hz, 15); 3.75 (q, $^3$J=6.30 Hz, 3); 2.50 (qt, 2H, $^3$J$_{2-1}$=10.80 Hz, $^3$J$_{2-3}$=6.60 Hz, 2); 1.47 (t, 3H, $^3$J=7.10 Hz, 16)

Compounds 55: 4-(4-(3,3,3-trifluoropropylcarbamoyl)phenyl)thiazole-2-isopropyl carboxylate and 56: 4-(thiazol-4-yl)-N-(3,3,3-trifluoropropyl)benzamide

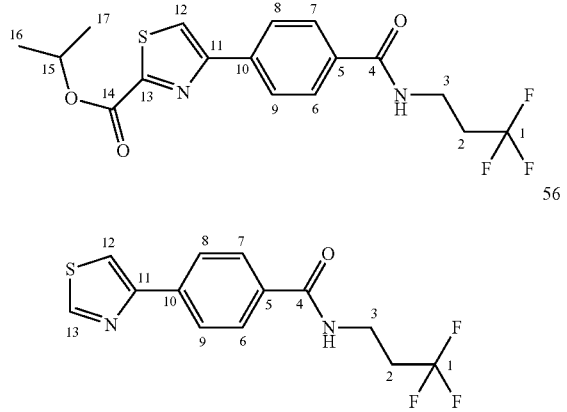

100 mg (1 eq.) 4-(2-bromoacetyl)-N-(3,3,3-trifluoropyl)benzamide (46), 40 mg (1.1 eq.) ethyl thiooxamate and 10 mL THF are introduced in a 25 mL flask. The mixture is agitated during 24 h under reflux. The THF is evaporated under reduced pressure. The product is then solubilized in 2.5 mL isopropanol.

In a flask cooled at 0° C., 20.4 mg (3 eq.) sodium are dissolved under argon in 2.5 mL isopropanol. The mixture is heated at 30° C. until complete dissolution of the sodium. The solution in the isopropanol previously obtained is added drop by drop to this solution. The mixture is then agitated during one night under reflux. 500 μL SOCl$_2$ are then added. The solution is agitated during one night at 50° C. The reaction medium is evaporated under reduced pressure and both compounds 55 and 56 formed in identical proportions are separated by preparative HPLC to yield 24 mg of 55 and 21.7 mg of 56.

Compound 55

LC-MS: $t_R$=4.90 min (method d); m/z: [M+H]$^+$=387

NMR $^1$H (CDCl$_3$, 300 MHz): δ ppm=8.07 (d, 2H, $^3$J=8.50 Hz); 7.84 (s, 1H, 12); 7.85 (d, 2H, $^3$J=8.50 Hz, 6+7); 6.42 (m, 1H, NH); 5.37 (sp, 1H, $^3$J=6.30 Hz, 15); 3.77 (q, 2H, $^3$J=6.30 Hz, 3); 2.52 (qt, 2H, $^3$J$_{2-1}$=10.70 Hz, $^3$J$_{2-3}$=6.40 Hz, 2); 1.46 (d, 6H, $^3$J=6.30 Hz, 16+17)

NMR $^{13}$C (CD$_2$Cl$_2$, 75 MHz): δ ppm=166.7 (4); 159.2 (13 or 14); 159.0 (13 or 14); 156.0 (11); 136.6 (10); 134.1 (5); 127.5 (6+7); 126.7 (q, $^1$J$_{C-F}$=276.8 Hz, 1); 126.6 (8+9); 120.2 (12); 70.8 (15); 33.6 (q, $^2$J$_{C-F}$=27.5 Hz, 2); 33.5 (q, $^3$J$_{C-F}$=3.6 Hz, 3); 21.5 (16+17)

Compound 56

LC-MS: $t_R$=5.82 min (method d); m/z: [M+H]$^+$=301

NMR $^1$H(CDCl$_3$, 300 MHz): δ ppm=8.92 (d, 1H, $^4$J=1.80 Hz, 13); 8.03 (d, 2H, $^3$J=8.40 Hz, 8+9); 7.85 (d, 2H, $^3$J=8.40 Hz, 6+7); 7.64 (d, 1H, $^4$J=1.80 Hz, 12); 3.77 (q, 2H, $^3$J=6.30 Hz, 3); 2.51 (qt, 2H, $^3$J$_{2-1}$=10.80 Hz, $^3$J$_{2-3}$=6.40 Hz, 2)

NMR $^{13}$C (CD$_2$Cl$_2$, 75 MHz): δ ppm=166.8 (4); 155.0 (11); 153.3 (13); 137.3 (10); 133.5 (5); 127.4 (6+7); 126.5 (8+9); 114.4 (12); 33.6 (q, $^2$J$_{C-F}$=27.3 Hz, 2); 33.4 (3)

Scheme 10

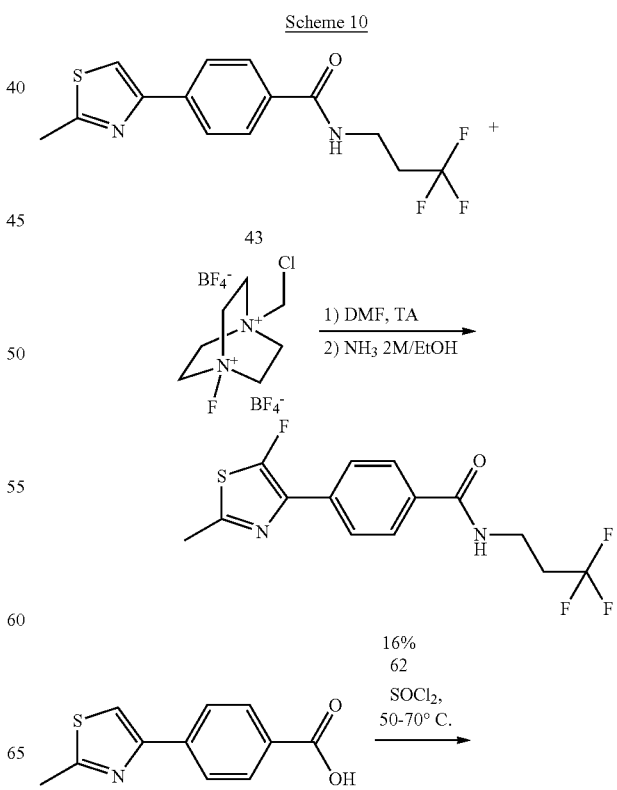

-continued

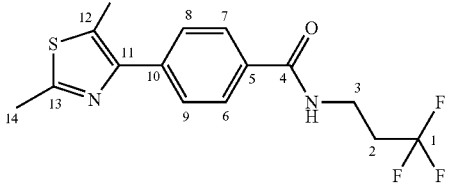

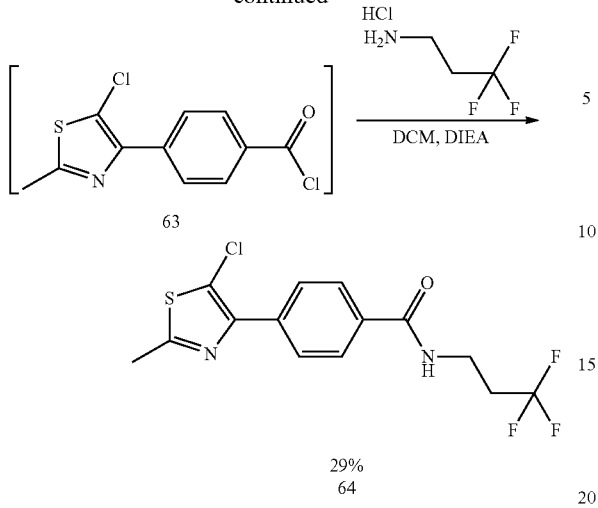

29%
64

Compound 62: 4-(5-fluoro-2-mthylthiazol-4-yl)-N-(3,3,3-trifluoropropyl)benzamide

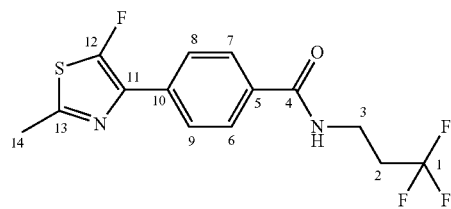 [SMILES: Cc1nc(-c2ccc(C(=O)NCCC(F)(F)F)cc2)c(F)s1]

101 mg (1 eq.) Selectfluor are added to a solution of 90 mg 4-(2-methylthiazol-4-yl)-N-(3,3,3-trifluoropropyl)benzamide (43) in 1.1 mL anhydrous DMF. The solution is agitated during 15 h at 5° C. The LCMS analysis of the reaction medium shows a very weak conversion of the initial product. 0.5 eq Selectfluor are then added at 0° C. and the solution is agitated during one night at 15° C. An additional 1 eq. Selectfluor is then added at 0° C. and the solution is then agitated during 24 h at AT. A conversion >70% is thus obtained. 1 mL of an ammonia solution 2M in the ethanol as well as 0.5 mL of water are added at 0° C. and the solution is agitated at AT during one night. The solvent is then evaporated under reduced pressure. The yellow oil thus obtained is taken over in the ethyl acetate and then washed using water (2×) and in brine (1×). The organic phase is dried on magnesium sulfate and then concentrated under reduced pressure. The yellow solid thus obtained is purified by preparative HPLC to yield 15 mg (16%) of white powder.

LC-MS: $t_R$=2.93 min (method c), 5.32 min (method d); m/z: [M+H]$^+$=333

NMR $^1$H (CD$_2$Cl$_2$ 300 MHz): δ ppm=7.97 (d, 2H, $^3$J=8.30 Hz, 8+9); 7.81 (d, 2H, $^3$J=8.30 Hz, 6+7); 6.52 (br s, 1H, NH); 3.70 (q, 2H, $^3$J=6.50 Hz, 3); 3.63 (d, 3H, $^5$J=2.30 Hz, 14); 2.50 (qt, $^3$J$_{2-1}$=10.90 Hz, $^3$J$_{2-3}$=6.70 Hz, 2)

NMR $^{13}$C (CD$_2$Cl$_2$, 75 MHz): δ ppm=167.4 (4); 158.2 (d, $^1$J$_{C-F}$=302.1 Hz, 12); 154.5 (d, $^3$J$_{C-F}$=10.X Hz, 13); 135.7 (d, $^3$J$_{C-F}$=5.8 Hz, 10); 133.6 (5); 133.5 (d, $^2$J$_{C-F}$=12.7 Hz, 11); 127.8 (6+7); 127.3 (d, $^4$J$_{C-F}$=6.1 Hz, 8+9); 127.2 (q, $^1$J$_{C-F}$=275.4 Hz 1); 34.2 (q, $^2$J$_{C-F}$=27.0 Hz, 2), 34.0 (3); 20.7 (14)

Compound 64: 4-(5-chloro-2-methylthiazol-4-yl)-N-(3,3,3-trifluoropropyl)benzamide

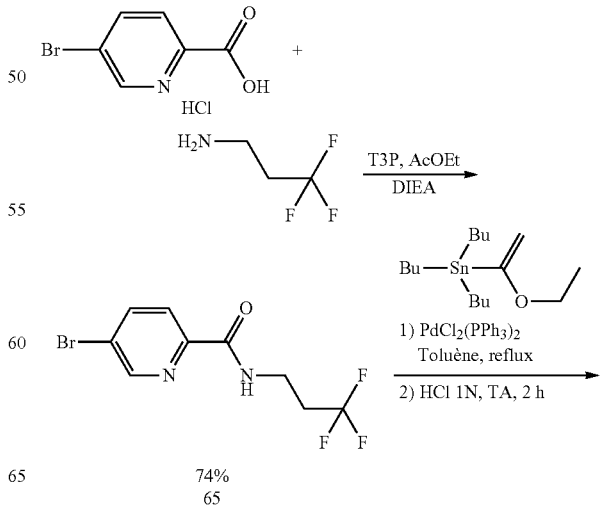

50 mg (1 eq.) 4-(2-methylthiazol-4-yl)benzoic acid are added to a solution of 5 mL thionyle chloride. The mixture is agitated at 50° C. during 2 h. 2 mL thionyle chloride are then added and the solution is agitated for a further 2 h at 50° C. A third adjunction of 2 mL SOCl$_2$ is then performed and the solution is agitated for a further 2 h at 50° C. The reaction medium is then evaporated under reduced pressure and the residue thus obtained (compound 63) is taken over in the dichloromethane. 34 mg (1 eq.) 3,3,3-trifluoropropylamine hydrochloride and 158 µL (4 eq.) DIEA are added to the reaction medium and the solution is agitated during one night at AT. The dichloromethane is then evaporated under reduced pressure and the residue is then taken over in the ethyl acetate. The organic phase is washed in brine (2×), dried on magnesium sulfate and then evaporated under reduced pressure. The beige oil thus obtained is then purified a first time on a pre-packed silica column (Cyclohexane 85:15 iPrOH). The recovered white powder is not pure. The product is then purified on preparative HPLC to yield 23.5 mg (29%) of white powder.

LCMS: $t_R$=3.37 min (method c); m/z: [M+H]$^+$=349, [M−H]$^-$=347

NMR $^1$H (CD$_2$Cl$_2$, 300 MHz): δ ppm=8.08 (d, 2H, $^3$J=8.40 Hz, 8+9); 7.84 (d, 2H, $^3$J=8.40 Hz, 6+7); 6.50 (m, 1H, NH); 3.74 (q, 2H, $^3$J=6.40 Hz, 3); 2.70 (s, 3H, 14); 2.53 (qt, 2H, $^3$J$_{2-1}$=10.90 Hz, $^3$J$_{2-3}$=6.40 Hz, 2)

NMR $^{13}$C (CD$_2$Cl$_2$, 75 MHz): δ ppm=167.4 (4); 163.6 (13); 148.2 (11); 136.7 (10); 134.1 (5); 128.8 (6+7); 127.4 (8+9); 127.3 (q, $^1$J$_{C-F}$=277 Hz, 1); 121.1 (12); 34.1 (q, $^2$J$_{C-F}$=27.6 Hz, 2); 34.0 (q, $^3$J$_{C-F}$=3.1 Hz, 3); 20.1 (14)

Scheme 11:

-continued

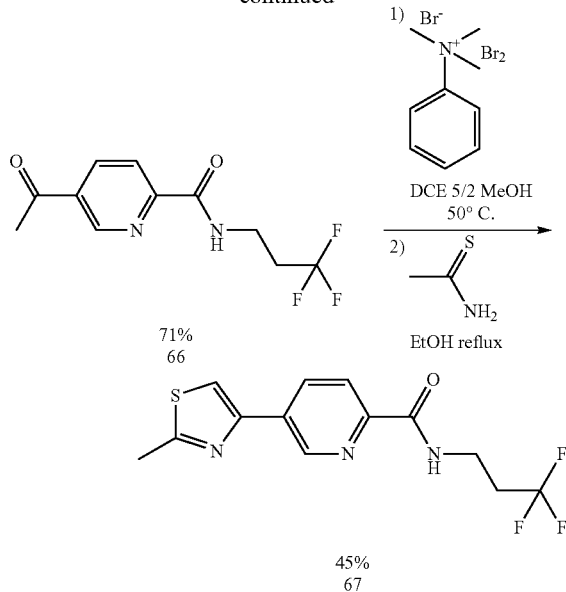

Compound 65:
5-bromo-N-(3,3,3-trifluoropropyl)picolinamide

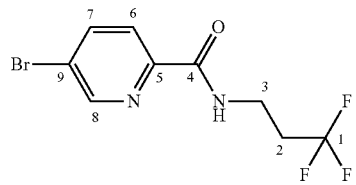

296 mg (1 eq.) 3,3,3-trifluoropropylamine hydrochloride are added to a solution of 400 mg (1 eq.) 5-bromopicolinic acid, 1.40 mL (1.2 eq.) of T3P solution at 50% in l'AcOEt and 1.03 mL (3 eq.) DIEA in 10 mL d'AcOEt. The mixture is agitated during 3 h at AT. Water and ethyl acetate are then added. The organic phase is washed using water (2×) and then in brine (1×), dried on magnesium sulfate and evaporated under reduced pressure to yield 433 mg (74%) of white solid.

LC-MS: $t_R$=2.58 min (method c); m/z: [M+H]$^+$=297

NMR $^1$H (CD$_3$OD, 300 MHz): δ ppm=8.73 (dd, 1H, $^4J_{7-8}$=2.25 Hz, $^5J_{8-6}$=0.52 Hz, 8); 8.16 (dd, 1H, $^3J_{7-6}$=8.39 Hz, $^4J_{7-8}$=2.27 Hz, 7); 8.01 (dd, 1H, $^3J_{6-7}$=8.33 Hz, $^5J_{6-8}$=0.59 Hz, 6); 3.67 (q, 2H, $^3J$=6.79 Hz, 3); 2.53 (qt, 2H, $^3J_{2-1}$=10.99 Hz, $^3J_{2-3}$=7.11 Hz, 2)

Compound 66:
5-acetyl-N-(3,3,3-trifluoropropyl)picolinamide

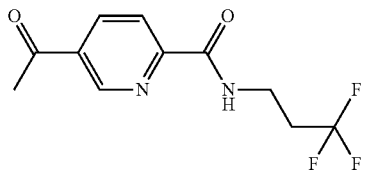 [SMILES: CC(=O)c1ccc(C(=O)NCCC(F)(F)F)nc1]

400 mg (1 eq.) 5-bromo-N-(3,3,3-trifluoropropyl)picolinamide (65) are added to a solution of 95 mg (0.1 eq.) PdCl$_2$(PPh$_3$)$_2$ in 3.5 mL toluene in a tube of Schlenk type under argon. The mixture is agitated during 5 min at AT and then 545 μL (1.2 eq.) tributyl(1-ethoxyvinyl)stannane are added, still under argon. The reaction medium is then agitated during one night at 90° C. The solution is cooled at AT and then 1 mL of an aqueous solution of hydrochloric acid 1N are added. The mixture is then agitated during 1 h at AT. The reaction medium is neutralized by means of an aqueous solution saturated with NaHCO$_3$ and then extracted using ethyl acetate. The organic phases are collected, washed in brine (2×), dried on magnesium sulfate and filtrated on celite. The yellow residue thus obtained is purified on a pre-packed silica column (Cyclohexane 95:5 AcOEt→9:1→85:15→75:25→7:3) to yield 250 mg (71%) of white solid.

LC-MS: $t_R$=1.57 min (method c); m/z: [M+H]$^+$=261

Compound 67: 5-(2-methylthiazol-4-yl)-N-(3,3,3-trifluoropropyl)picolinamide

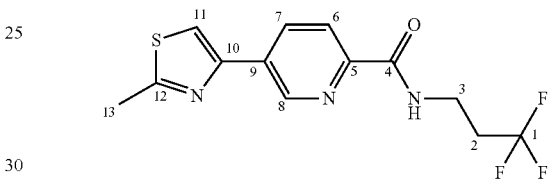

332 mg (1 eq.) trimethylphenylammonium tribromure are added to a solution of 230 mg (1 eq.) 5-acetyl-N-(3,3,3-trifluoropropyl)picolinamide (66) in a mixture of DCE (12.5 mL)/MeOH (5 mL). The mixture is agitated during 24 h at 70° C. The mixture of solvent is then evaporated under reduced pressure. The residue is taken over in the ethyl acetate and washed in water and then in brine. The organic phase is dried on magnesium sulfate and evaporated under reduced pressure to yield a yellow solid that is then solubilized in 2 mL absolute EtOH. 101 mg (1.5 eq.) thioacetamide are then added and the reaction medium is agitated during 4 h under reflux. The EtOH is evaporated under reduced pressure and the residue is taken over in the ethyl acetate. The organic phase is washed using water (2×) and in brine (1×), dried on magnesium sulfate and then evaporated under reduced pressure. The residue is purified by preparative HPLC to yield 125 mg (45%) of white powder.

LC-MS: $t_R$=2.53 min (method c); m/z: [M+H]$^+$=316

NMR $^1$H (CD$_3$OD, 300 MHz): δ ppm=9.15 (dd, 1H, $^4J_{8-7}$=2.20 Hz, $^5J_{8-6}$=0.75 Hz, 8); 8.40 (dd, 1H, $^3J_{7-6}$=8.18 Hz, $^4J_{7-8}$=2.23 Hz, 7); 8.12 (dd, 1H, $^3J_{6-7}$=8.18 Hz, $^5J_{6-8}$=0.74 Hz, 6); 7.94 (s, 1H, 11); 3.69 (t, 2H, $^3J$=7.11 Hz, 3); 2.78 (s, 3H, 13); 2.55 (qt, $^3J_{2-1}$=10.97 Hz, $^3J_{2-3}$=7.22 Hz, 2)

NMR $^{13}$C (CD$_3$OD, 75 MHz): δ ppm=167.7 (12); 165.2 (4); 150.7 (10); 148.2 (5); 146.2 (8); 134.3 (7); 132.7 (9); 126.5 (q, $^1J_{C-F}$=275.9 Hz, 1); 121.7 (6); 116.2 (11); 32.8 (q, $^2J_{C-F}$=27.8 Hz, 2); 32.6 (q, $^3J_{C-F}$=3.7 Hz, 3); 17.5 (13)

Scheme 12:

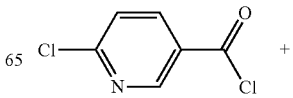

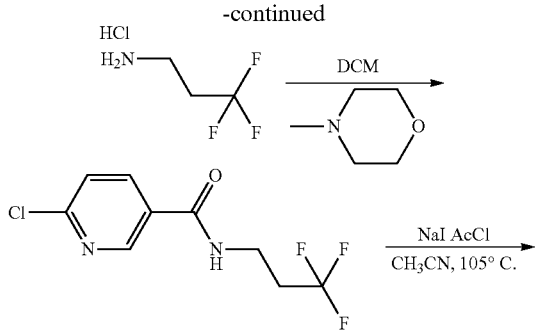

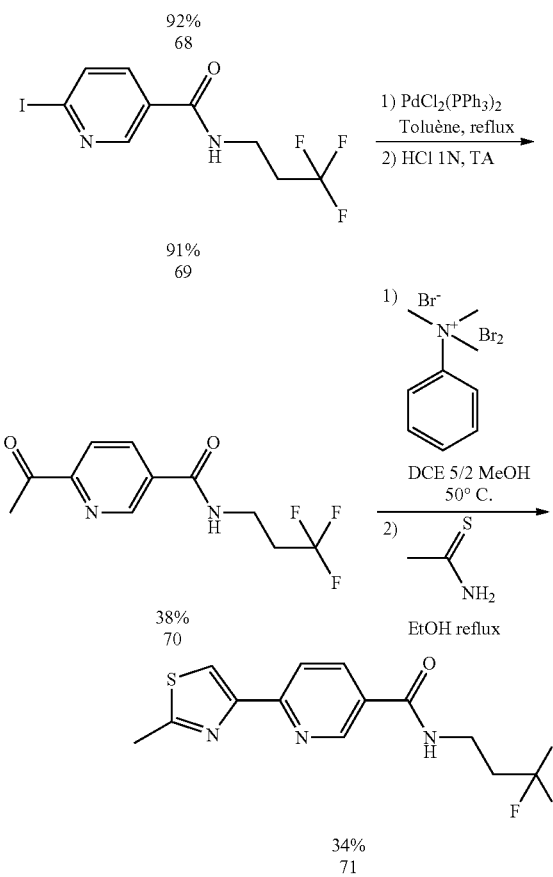

Compound 68:
6-chloro-N-(3,3,3-trifluoropropyl)nicotinamide

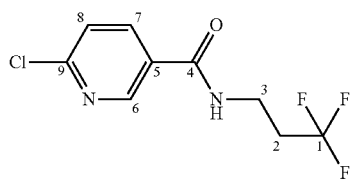

700 mg (1 eq.) 6-chloro-nicotinic acid chloride are added to a solution of 595 mg (1 eq.) 3,3,3-trifluoropropylamine hydrochloride and 1.75 mL (4 eq.) N-methylmorpholine in 40 mL anhydrous DCM. The reaction medium is agitated during 1 h at AT. An additional equivalent (700 mg) of acid chloride is added and the solution is agitated during one night at AT. The DCM is evaporated under reduced pressure. The solid thus obtained is taken over in a mixture of Cylohexane 1:1 Ethyl acetate and then filtrated on silica. The product is then purified on a pre-packed silica column (Cyclohexane 7:3 AcOEt) to yield 918 mg (92%) of white powder.

LC-MS: $t_R$=2.32 min (method c); m/z: [M+H]$^+$=253, [M−H]$^-$=251

Compound 69:
6-iodo-N-(3,3,3-trifluoropropyl)nicotinamide

28 μL (0.2 eq.) acetic acid chloride are added under argon to a solution of 500 mg (1 eq.) 6-chloro-N-(3,3,3-trifluoropropyl)nicotinamide (68), 1.48 g (5 eq.) NaI in 15 mL acetonitrile in a carrousel tube. The solution is agitated at 105° C. during one night. The acetonitrile is evaporated under reduced pressure, the product is then taken over in the ethyl acetate, filtrated, washed with an aqueous solution of Na$_2$SO$_3$ at 10% and then with an aqueous solution of Na$_2$CO$_3$ at 5% and then in brine. The organic phase is then dried on magnesium sulfate and then evaporated under reduced pressure to yield 619 mg (91%) of white powder.

LC-MS: $t_R$=2.33 min (method c); m/z: [M+H]$^+$=345, [M−H]$^-$=343

Compound 70:
6-acetyl-N-(3,3,3-trifluoropropyl)nicotinamide 300 mg (1 eq.) 6-iodo-N-(3,3,3-trifluoropropyl)nicotinamide (69) are added to a solution of 61 mg (0.1 eq.) PdCl$_2$(PPh$_3$)$_2$ in 2.6 mL toluene. The reaction medium is agitated for 5 min at AT and then 353 μL (1.2 eq.) tributyl (1-ethoxyvinyl)stannane are added under argon. The reaction medium is then agitated under argon during one night at 110° C. The reaction medium is cooled at AT, and then 8 mL of an aqueous solution of HCl 1N are added and the solution is agitated during 2 h at AT. The reaction medium is neutralized by means of an aqueous solution saturated with NaHCO$_3$. The medium is extracted using ethyl acetate. The organic phases are collected, washed in brine (2×), dried on magnesium sulfate and filtrated on celite. The brown residue thus obtained is solubilized in 5 mL acetonitrile and then filtrated. The filtrate is then purified by preparative HPLC to yield 89 mg (35%) of white powder.

LC-MS: $t_R$=4.10 min (method d); m/z: [M+H]$^+$=261, [M−H]$^-$=259

Compound 71: 6-(2-methylthiazol-4-yl)-N-(3,3,3-trifluoropropyl)nicotinamide

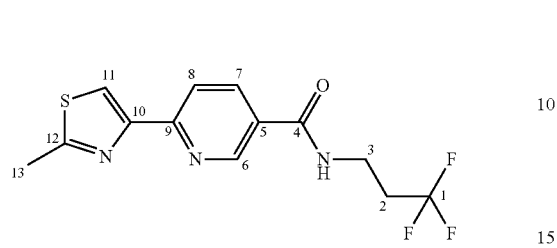

129 mg (1 eq.) trimethylphenylammonium tribromide are added to a solution of 89 mg (1 eq.) 6-acetyl-N-(3,3,3-trifluoropropyl)nicotinamide (70) in 5.9 mL of a mixture DCE 5:2 MeOH. The reaction medium is agitated at 50° C. during 2 h. The LCMS analysis of the milieu shows a conversion rate close to zero, the reaction is then heated at 70° C. during 72 h. The LCMS analysis of the milieu shows an incomplete conversion of the reaction medium and the formation of two majority products: mono-brominated ketone and mono-chlorinated ketone, as well as a little di-chlorinated ketone. The reaction is however stopped, and the solvent mixture is evaporated under reduced pressure. The residue is taken over in 1 mL absolute ethanol. 26 mg (1 eq.) thioacetamide are then added and the solution is agitated during 1 h under reflux. An additional 13 mg (0.5 eq.) are added and the reaction medium is agitated during 3 h under reflux and then cooled at AT. 6 mL diethyl ether are added and the solution is cooled in a refrigerator during one night. The formed precipitate is filtrated and then washed using diethyl ether. The precipitate is taken over in the ethyl acetate and then washed with an aqueous solution saturated with NaHCO$_3$ (2×) and then in brine (1×). The organic phase is then dried on magnesium sulfate and then evaporated under reduced pressure in order to yield 39 mg (34%) of white powder.

LC-MS: $t_R$=2.28 min (method c); m/z: [M+H]$^+$=316, [M−H]$^-$=314

NMR $^1$H (CD$_3$OD, 300 MHz): δ ppm=8.97 (dd, 1H, $^4J_{6-7}$=2.29 Hz, $^5J_{6-8}$=0.84 Hz, 6); 8.24 (dd, 1H, $^3J_{7-8}$=8.27 Hz, $^4J_{7-6}$=2.30 Hz, 7); 8.13 (dd, 1H, $^3J_{8-7}$, =8.30 Hz, $^5J_{8-6}$=0.81 Hz, 8); 8.11 (s, 1H, 11); 3.65 (t, 2H, $^3$J=7.00 Hz, 3); 2.76 (s, 3H, 13); 2.55 (qt, 2H, $^3J_{2-1}$=10.84 Hz, $^3J_{2-3}$=7.13 Hz, 2)

NMR $^{13}$C (CD$_3$OD, 75 MHz): δ ppm=167.3 (12); 166.4 (4); 154.4 (9); 153.4 (10); 148.1 (6); 136.1 (7); 128.5 (5); 126.6 (q, $^1J_{C-F}$=276.3 Hz, 1); 120.3 (8); 118.8 (11); 33.1 (q,=9.74 Hz, 3); 32.6 (q, $^2J_{C-F}$=27.7 Hz, 2); 17.6 (13)

Scheme 13:

a/

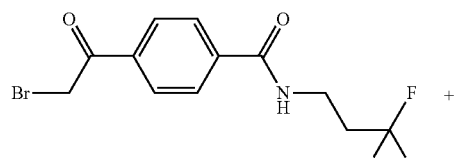

46 b/

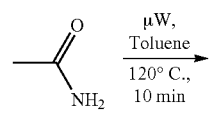

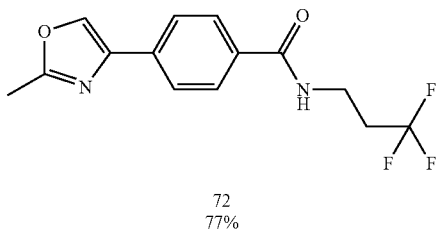

72
77%

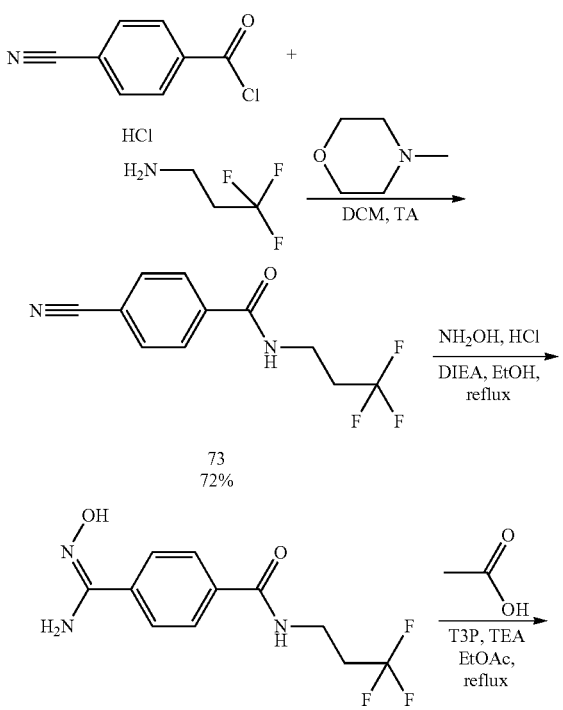

73
72%

74
97%

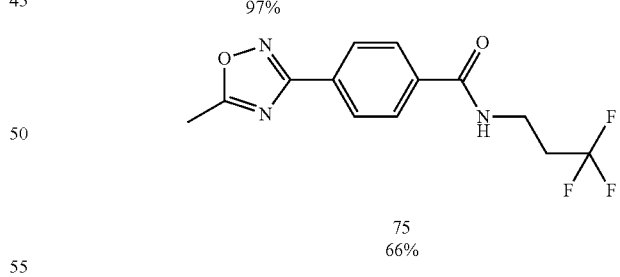

75
66% c/

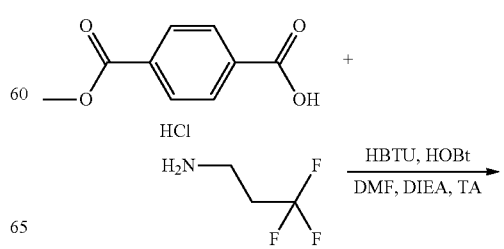

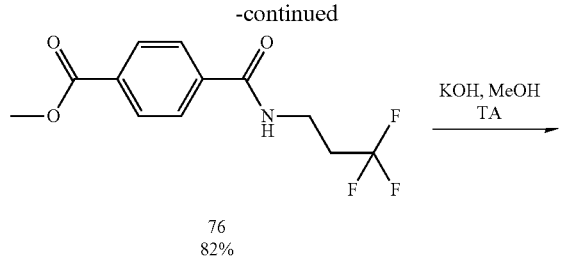
76
82%
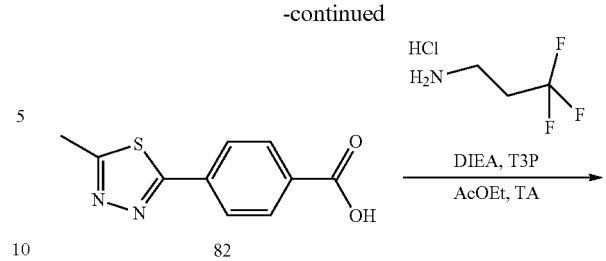
82
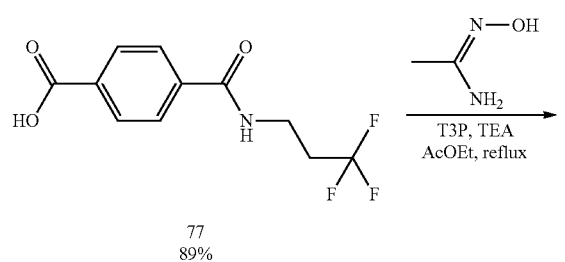
77
89%
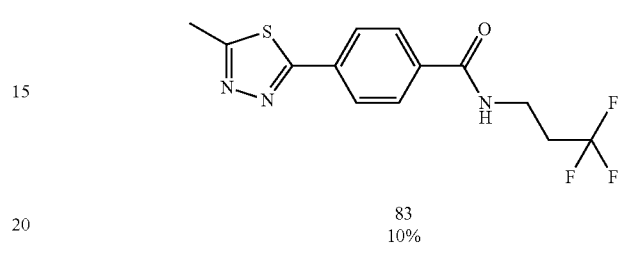
83
10%
f/
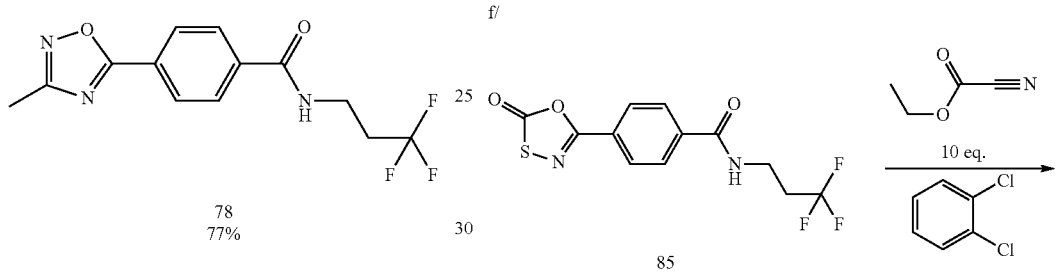
85
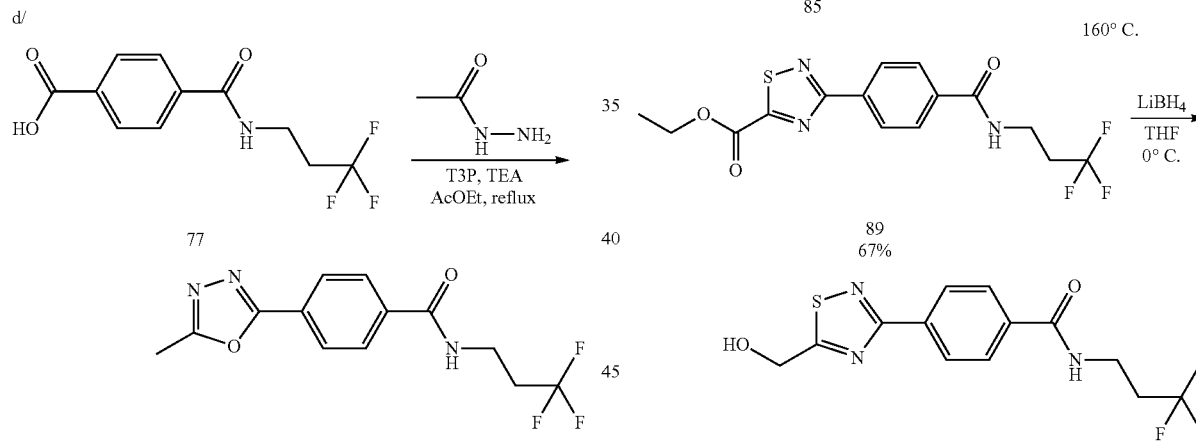
d/
77
80
90%
89
67%
90
44%
e/
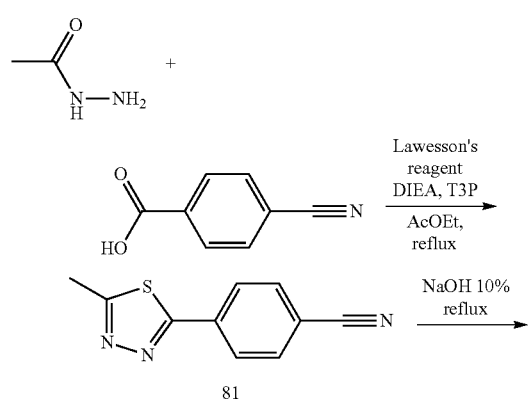
81
g/
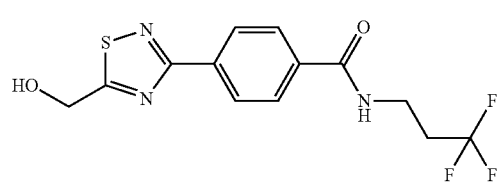
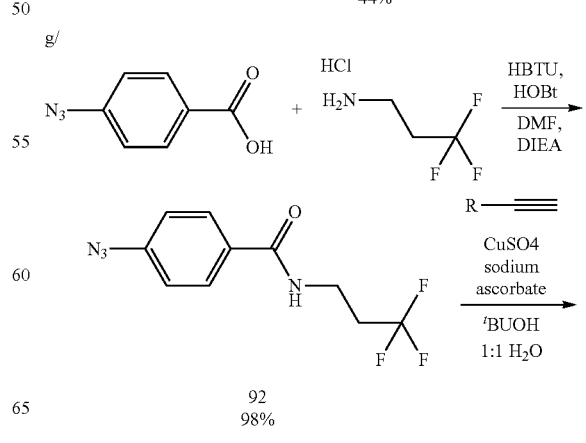
92
98%

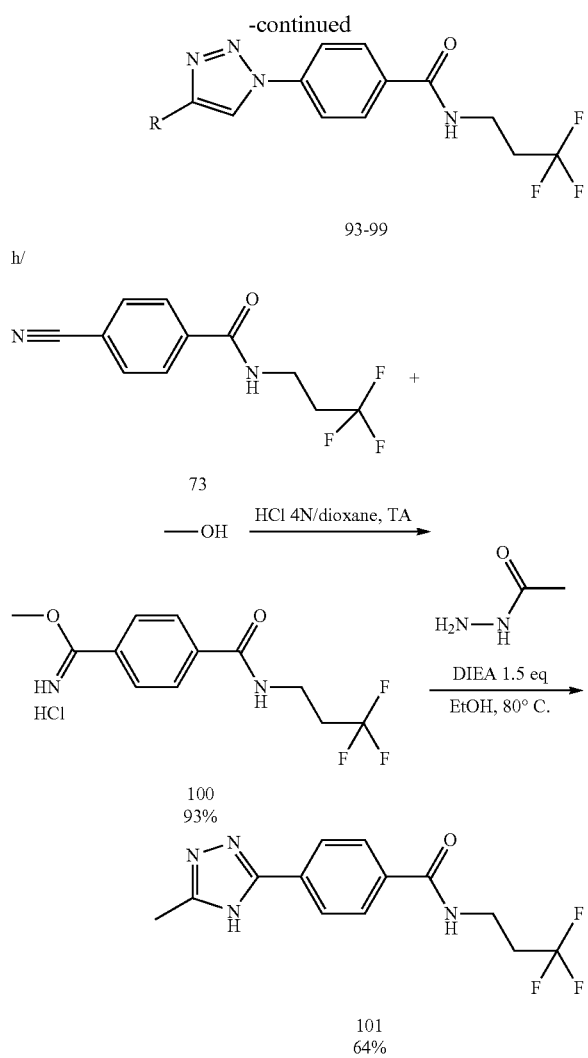

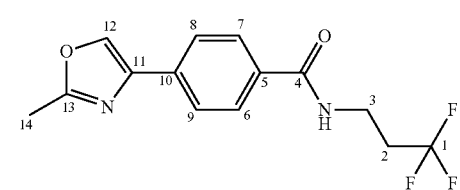

Compound 72: 4-(2-methyloxazol-4-yl)-N-(3,3,3-trifluoropropyl)benzamide 100 mg (1 eq.) 4-acetyl-N-(3,3,3-trifluoropropyl)benzamide (45) are added to a solution of 21 mg (1.2 eq.) acetamide in 300 μL toluene. The reaction medium is agitated in a microwave reactor during 10 min at 110° C. ($P_{max}$=300W). 240 mg (3 eq.) Tos-NHNH$_2$ resin are added. The solution is agitated one night at AT and then filtrated. The solution is taken over in the ethyl acetate and then washed using water (2×) and in brine (1×). The organic phase is dried on magnesium sulfate and then evaporated under reduced pressure in order to yield 68 mg (77%) of beige powder.

LC-MS: $t_R$=2.30 min (method c); m/z: [M+H]$^+$=299, [M−H]$^-$=297

NMR $^1$H (CD$_2$Cl$_2$, 300 MHz): δ ppm=7.97 (s, 12); 7.84-7.77 (m, 4H, 6+7+8+9); 3.70 (q, 2H, $^3$J=6.50 Hz, 3); 2.60-2.44 (m, 3H, 14+2)

NMR $^{13}$C (CD$_2$Cl$_2$, 75 MHz): δ ppm=167.6 (4); 162.8 (13); 140.0 (11); 134.9 (5 or 10); 134.8 (5 or 10); 133.6 (12); 127.8 (6+7 or 8+9); 127.1 (q, $^1$J$_{C-F}$=277.0 Hz, 1); 125.7 (6+7 or 8+9); 33.8 (q, $^2$J$_{C-F}$=27.1 Hz, 2); 33.8 (q, $^3$J$_{C-F}$=3.7 Hz, 3); 14.0 (3)

Compound 73: 4-cyano-N-(3,3,3-trifluoropropyl)benzamide

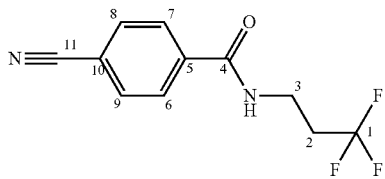

305 mg (1 eq.) 3,3,3-trifluoropropylamine hydrochloride are added to a solution of 300 mg (1 eq.) 4-cyanobenzoic acid, 1.46 mL (1.2 eq.) of T3P solution at 50% in the ethyl acetate and 1.4 mL (4 eq.) DIEA in 3 mL ethyl acetate. The reaction medium is agitated one night at AT. The solution is then washed using water (2×) and then in brine (1×). The organic phase is dried on magnesium sulfate, evaporated under reduced pressure to yield 424 mg (86%) of white solid.

LC-MS: $t_R$=2.31 min (method c); m/z: [M−H]$^-$=241

NMR $^1$H (CDCl$_3$, 300 MHz): δ ppm=7.86 (d, 2H, $^3$J=8.47 Hz, 6+7); 7.75 (d, 2H, $^3$J=8.47 Hz, 8+9); 6.50 (br, s, 0.5H, NH); 3.74 (q, 2H, $^3$J=6.30 Hz; 3); 2.49 (qt, 2H, $^3$J$_{2-1}$=10.69 Hz, $^3$J$_{2-3}$=6.38 Hz; 2)

Compound 74: 4-(N'-hydroxycarbamimidoyl)-N-(3,3,3-trifluoropropyl)benzamide

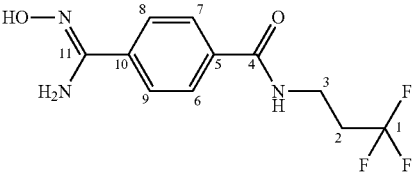

300 mg (1 eq.) 4-cyano-N-(3,3,3-trifluoro-propyl)-benzamide (73) are added to a solution of 129 mg (1.5 eq.) hydroxylamine hydrochloride and 343 μL (1.6 eq.) DIEA in 2.5 mL ethanol. The solution is agitated under reflux during 2 h. The solvent is then evaporated under reduced pressure. The residue is taken over in the ethyl acetate and then washed using water (2×) and in brine (1×). The organic phase is dried on magnesium sulfate and evaporated under reduced pressure to yield 330 mg (97%) of white powder.

LC-MS: $t_R$=3.74 min (method d); m/z: [M−H]$^-$=274

NMR $^1$H DMSO-d$_6$ 300 MHz): δ ppm=9.79 (s, 1H, OH); 8.70 (t, 1H, $^3$J=5.52 Hz, NH-amide); 7.83 (d, 2H, $^3$J=8.55 Hz, 6+7 or 8+9); 7.77 (d, 2H, $^3$J=8.48 Hz, 7+6 or 8+9); 5.89

(s, 2H, NH$_2$); 3.50 (q, 2H, $^3$J=6.49 Hz, 3); 2.55 (qt, 2H, $^3$J$_{2-1}$=11.42 Hz, $^3$J$_{2-3}$=6.94 Hz, 2).

Compound 75: 4-(5-methyl-1,2,4-oxadiazol-3-yl)-N-(3,3,3-trifluoropropyl)benzamide

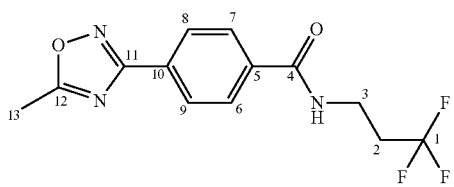

330 mg (1 eq.) 4-(N'-hydroxycarbamimidoyl)-N-(3,3,3-trifluoropropyl)benzamide (74) are added to a solution of 78 µL (1.1 eq.) acetic acid, 1.84 mL (2.5 eq.) of T3P solution at 50% in the ethyl acetate and 643 µL (3 eq.) DIEA in 9 mL ethyl acetate. The solution is agitated during one night under reflux. The conversion is incomplete. The reaction medium is then evaporated under reduced pressure. 1 mL ethyl acetate, 368 µL (0.5 eq) T3P and 107 µL (0.5 eq.) DIEA are added. The solution is agitated during 48 h under reflux. 2 mL of water are then added and the reaction is agitated during 15 min at AT The organic phase is then washed using water (2×) and then in brine (1×), dried on magnesium sulfate and evaporated under reduced pressure. The residue thus obtained is purified on a pre-packed silica column (Cyclohexane 9:1 Isopropanol) to yield 215 mg (66%) of white solid.

LC-MS: t$_R$=2.37 min (method c); m/z: [M+H]$^+$=300, [M−H]$^-$=298

NMR $^1$H (DMSO-d$_6$, 300 MHz): δ ppm=8.86 (t, 1H, $^3$J=5.54 Hz, NH); 8.09 (d, 2H, $^3$J=8.46 Hz, 8+9); 7.99 (d, 2H, $^3$J=8.55 Hz, 6+7); 3.52 (q, 2H, $^3$J=6.42 Hz, 3); 2.68-2.50 (m, 5H, 13+2)

NMR $^{13}$C (DMSO-d$_6$ 75 MHz): δ ppm=177.8 (12); 167.1 (11); 165.6 (4); 136.6 (5); 128.8 (10); 128.1 (6+7); 127.0 (8+9); 126.9 (q, =277.12 Hz, 1); 32.9 (3); 32.4 (q, 2J$_{C-F}$=27.1 Hz, 2)

Compound 76: 4-(3,3,3-trifluoropropylcarbamoyl)methyl benzoate

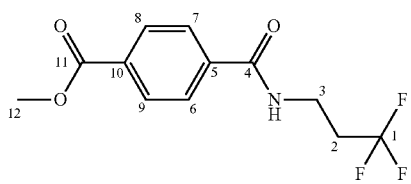

1.66 g (1 eq.) 3,3,3-trifluoropropylamine hydrochloride are added to a solution of 2 g (1 eq.) mono-methylterephtalate, 5.04 g (1.2 eq.) HBTU, 0.3 g (0.2 eq.) HOBt and 7.7 mL (4 eq.) DIEA in 45.5 mL DMF on a molecular sieve. The reaction medium is agitated at AT during 1 h. The DMF is then evaporated under reduced pressure. The residue is taken over in the ethyl acetate and then washed with a solution saturated with NaHCO$_3$ (2×), a solution of hydrochloric acid 1N (2×) using water (1×) and in brine (1×). The organic phase is then dried on magnesium sulfate and then evaporated under reduced pressure. The residue thus obtained is purified on a pre-packed silica column (Cyclohexane 9:1 AcOEt→Cyclohexane 85:15 AcOEt) to yield 1.25 g (41%) of white powder. The impure fractions are again purified on a pre-packed silica column (Cyclohexane 9:1 AcOEt) to yield 1.27 g (41%) of white powder. This results in a yield of 82%.

LCMS: t$_R$=2.44 min (method c); m/z: [M−H]$^-$=274

NMR $^1$H (CD$_2$Cl$_2$, 300 MHz): δ ppm: 8.10 (d, 2H, $^3$J=8.63 Hz, 8+9 or 6+7); 7.83 (d, 2H, $^3$J=8.55 Hz, 7+6 or 8+9); 6.60 (br s, 1H, NH); 3.95 (s, 3H, 12); 3.74 (q, 2H, $^3$J=6.45 Hz, 3); 2.53 (qt, 2H, $^3$J$_{2-1}$=10.93 Hz, $^3$J$_{2-3}$=6.63 Hz, 2)

Compound 77: 4-(3,3,3-trifluoropropylcarbamoyl)benzoic acid

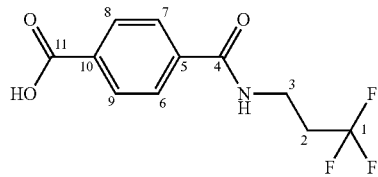

300 mg (1 eq.) 4-(3,3,3-trifluoropropylcarbamoyl)methyl benzoate (76) are added to a solution of 244.6 mg (4 eq.) potassium hydroxide in 2.66 mL MeOH. The mixture is agitated under reflux during 2 h. The reaction medium is then evaporated under reduced pressure. The white solid thus obtained is taken over in a mixture water: AcOEt. The aqueous phase is washed using ethyl acetate and then acidified by means of an aqueous solution of hydrochloric acid 1N up to pH=2. The formed white precipitate is then solubilized in the ethyl acetate. The organic phase is washed using water (2×) and then in brine (1×), dried on magnesium sulfate and then concentrated under reduced pressure to yield 254 mg (89%) of white powder.

LC-MS: t$_R$=4.28 min (method d); m/z: [M−H]$^-$=260

NMR $^1$H (DMSO-d$_6$, 300 MHz): δ ppm=13.21 (br s, 1H, COOH); 8.84 (t, 1H, $^3$J=5.56 Hz, NH); 8.02 (d, 2H, $^3$J=8.25 Hz, 6+7 or 8+9); 7.91 (d, 2H, $^3$J=8.25 Hz, 6+7 or 8+9); 3.50 (q, 2H, $^3$J=6.30 Hz, 3); 2.55 (qt, 2H, $^3$J$_{2-1}$=11.44 Hz, $^3$J$_{2-3}$=6.96 Hz, 2)

Compound 78: 4-(3-methyl-1,2,4-oxadiazol-5-yl)-N-(3,3,3-trifluoropropyl)benzamide

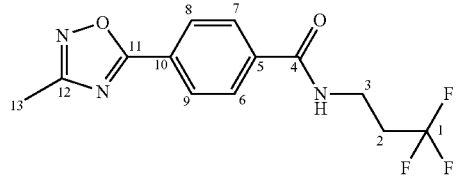

100 mg (1 eq.) 4-(3,3,3-trifluoropropylcarbamoyl)benzoic acid (77) are added to a solution of 28.4 mg (1 eq.) acetamidoxime, 570 µL (2.5 eq.) of T3P solution at 50% in the ethyl acetate, 199 µL (3 eq.) DIEA in 191 µL ethyl acetate. The mixture is agitated under reflux during 12 h. The CCM analysis of the medium shows an incomplete conversion. 228 μL (1 eq.) of T3P solution and 66 μL (1 eq.) DIEA are then added. The reaction is agitated for a further 24 h under reflux. 200 μL of water are added to the reaction medium at AT and the solution is agitated during 10 min at AT. The product is purified by preparative HPLC to yield 88 mg (77%) of white powder.

LC-MS: $t_R$=3.00 min (method c); m/z: [M−H]⁻=298

NMR ¹H (CD₂Cl₂, 300 MHz): δ ppm=8.21 (d, 2H, ³J=8.42 Hz, 8+9); 7.91 (d, 2H, ³J=8.42 Hz, 6+7); 6.54 (br s, H, NH); 3.75 (q, 2H, ³J=6.41 Hz, 3); 2.61-2.46 (m, 5H, 13+2)

NMR ¹³C (CD₂Cl₂, 75 MHz): δ ppm=174.8 (4); 168.5 (12); 166.6 (4); 138.1 (5); 128.6 (8+9); 128.0 (6+7); 127.4 (10); 127.0 (q, ¹$J_{C-F}$=276.8 Hz, 1); 34.0 (3); 33.9 (q, ²$J_{C-F}$=27.6 Hz, 2); 11.9 (13)

Compound 80: 4-(5-methyl-1,3,4-oxadiazol-2-yl)-N-(3,3,3-trifluoropropyl)benzamide

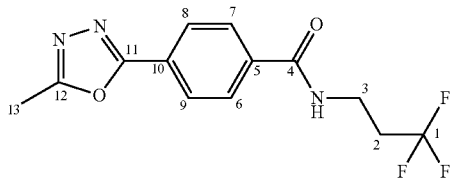

100 mg (1 eq.) 4-(3,3,3-trifluoropropylcarbamoyl)benzoic acid (77) are added to a solution of 31.2 mg (1.1 eq.) acetylhydrazine, 570 μL (2.5 eq.) of T3P solution at 50% in the ethyl acetate and 199 μL (3 eq.) DIEA in 196 μL ethyl acetate. The solution is agitated during 24 h under reflux. The LCMS analysis of the reaction medium shows the formation of 50% of the desired product and of 50% of the non-cyclized intermediate product. 66 μL (1 eq.) DIEA and 228 μL of T3P solution at 50% in the ethyl acetate are then added and the solution is agitated during 48 h under reflux. The solution is left to return at AT and then 1 mL of water is added and the mixture is agitated during 15 min at AT. The organic phase is then washed using water (2×) and in brine (1×), dried on magnesium sulfate and evaporated under reduced pressure to yield 102 mg (90%) of white powder.

LC-MS: $t_R$=4.68 min (method d); m/z: [M−H]⁻=298

NMR ¹H (CD₂Cl₂, 300 MHz): δ ppm=8.07 (d, 2H, ³J=8.44 Hz, 8+9); 7.88 (d, 2H, ³J=8.44 Hz, 6+7); 6.73 (br s, 1H, NH); 3.72 (q, 2H, ³J=6.46 Hz, 3); 2.60 (s, 3H, 13); 2.50 (qt, 2H, ³$J_{2-1}$=10.85 Hz, ³$J_{2-3}$=6.64 Hz, 2)

NMR ¹³C (CD₂Cl₂, 75 MHz): δ ppm=166.8 (4); 164.7 (12); 164.5 (11); 137.2 (5); 128.1 (6+7); 127.2 (10); 127.2 (8+9); 127.0 (q, ¹$J_{C-F}$=275.9 Hz, 1); 34.1 (q, ³$J_{C-F}$=2.8 Hz, 3); 33.9 (q, ²$J_{C-F}$=27.7 Hz, 2); 11.3 (13)

Compound 81: 4-(5-methyl-1,3,4-thiadiazol-2-yl)benzonitrile

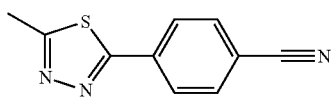

482 mg (1.5 eq.) Lawesson reagent are added at AT to a solution of 100 mg (1 eq.) 4-cyanobenzoic acid, 51 mg (1 eq.) acetylhydrazine, 606 μL (1.5 eq.) of T3P solution at 50% in the ethyl acetate and 295 μL (2.5 eq.) DIEA in 1.5 mL ethyl acetate. The solution is then heated during one night under reflux. The reaction medium is cooled at AT and then 5 mL of water are added. The solution is agitated during 15 min at AT. The organic phase is washed with an aqueous solution saturated with NaHCO₃ (2×) and then in brine (1×), dried on magnesium sulfate and evaporated under reduced pressure. The yellow oil thus obtained is used as is in the following reaction.

LC-MS: $t_R$=2.10 min (method c); m/z: [M+H]⁺=202

Compound 82: 4-(5-methyl-1,3,4-thiadiazol-2-yl)benzoic acid

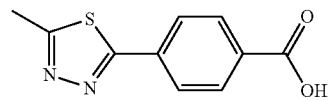

137 mg (1 eq.) 4-(5-methyl-1,3,4-thiadiazol-2-yl)benzonitrile (81) are added to 5 mL of an aqueous soda solution at 10%. The mixture is agitated during 1 h under reflux and then cooled at AT and finally washed using ethyl acetate. The aqueous phase is then acidified by means of a solution of HCl 1N up to pH=2 and then extracted using ethyl acetate. The organic phases are collected, dried on magnesium sulfate and then evaporated under, reduced pressure. The product is used as is in the following step.

LC-MS: $t_R$=1.65 min (method c); m/z: [M−H]⁻=219

Compound 83: 4-(5-methyl-1,3,4-thiadiazol-2-yl)-N-(3,3,3-trifluoropropyl)benzamide

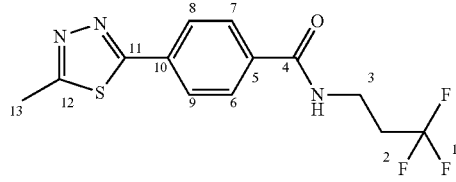

101 mg (1 eq.) 3,3,3-trifluoropropylamine hydrochloride are added to a solution of 150 mg (1 eq.) 4-(5-methyl-1,3,4-thiadiazol-2-yl)benzoic acid (82), 485 μL (1.2 eq.) of T3P solution at 50% in the ethyl acetate and 353 μL (3 eq.) DIEA in 3 mL ethyl acetate. The solution is agitated during one night at AT. 81 μL (0.2 eq.) of T3P solution are added and the mixture is agitated during 4 h at AT. 2 mL of water are added and the reaction medium is agitated during 15 min at AT. The organic phase is washed using water (2×) and then in brine (1×), dried on magnesium sulfate and then evaporated under reduced pressure. The residue thus obtained is purified on a pre-packed silica column (DCM→DCM 99:1 MeOH→DCM 98:2 MeOH) to yield 22 mg (10%) of white powder.

LC-MS: $t_R$=2.17 min (method c); m/z: [M+H]⁺=316, [M−H]⁻=314

NMR ¹H (CD₂Cl₂, 300 MHz): δ ppm=8.04 (d, 2H, ³J=8.71 Hz, 8+9); 7.95 (d, 2H, ³J=8.71 Hz, 6+7); 3.65 (t, 2H, ³J=6.99 Hz, 3); 2.83 (s, 3H, 13); 2.55 (qt, ³$J_{2-1}$=10.88 Hz, ³$J_{2-3}$=7.10 Hz, 2)

NMR $^{13}$C (CD$_2$Cl$_2$, 300 MHz): δ ppm=169.7 (11); 169.1 (4); 168.4 (12); 137.7 (5 or 10); 134.0 (5 or 10); 129.3 (6+7); 128.9 (8+9); 128.0 (q, $^1$J$_{C-F}$=276.3 Hz, 1); 34.5 (3); 34.0 (q, $^2$J$_{C-F}$=27.8 Hz, 2)

Compound 84:
N1-(3,3,3-trifluoropropyl)terephthalamide

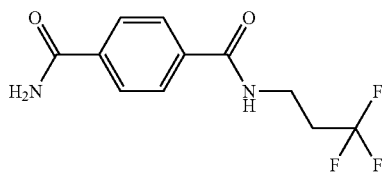

2 mL ammonia solution 7N in the methanol are added to a solution of 200 mg 4-(3,3,3-trifluoropropylcarbamoyl) methyl benzoate (76) in 2 mL methanol. The solution is agitated during 36 h under reflux. The LCMS and CCM analyses of the reaction medium show nearly no conversion of the starting ester. 500 µL of water and 163 mg (4 eq.) KOH are then added and the reaction medium is agitated during one night under reflux. The solution is acidified up, to pH=4 by means of a solution of hydrochloric acid 1N. The formed white precipitate is filtrated and dried one night in a desiccator (148 mg).

The product is then solubilized in 10 mL of a mixture DCE:SOCl$_2$ (1:1). The, solution is agitated during 4 h at 50° C. The solution is concentrated under reduced pressure and then taken over at 0° C. in 15 mL of a mixture CH$_3$CN: NH$_4$OH 28% (2:1). The solution is, agitated at AT for one night. The reaction medium is extracted using ethyl acetate. The organic phases are regrouped and then washed using water (2×) and in brine (1×), dried on magnesium sulfate and evaporated under reduced pressure to yield 115 mg (61%) of white solid.

LC-MS: t$_R$=1.77 min (method c); m/z: [M−H]$^-$=259

Compound 85: 4-(2-oxo-1,3,4-oxathiazol-5-yl)-N-(3,3,3-trifluoropropyl)benzamide

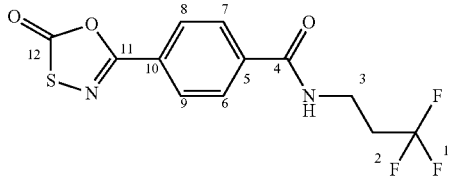 [SMILES: O=C(NCCC(F)(F)F)c1ccc(-c2nsc(=O)o2)cc1]

75 µL (2 eq.) (chlorothio)formyle chloride are added to a solution of 115 mg (1 eq.) N1-(3,3,3-trifluoropropyl)terephthalamide (84) in 1.1 mL toluene. The reaction medium is agitated during 24 h at 90° C. 38 µL (1 eq.) (chlorothio) formyle chloride are then added and the reaction is agitated at 90° C. during a further 24 h. The toluene is evaporated under reduced pressure. The residue is taken over in some dichloromethane and then filtrated to yield 95 mg (68%) of white solid.

LC-MS: t$_R$=2.57 min (method c); m/z: [M−H]$^-$=317

NMR $^1$H (DMSO-d$_6$, 300 MHz): δ ppm=8.90 (t, 1H, $^3$J=5.67 Hz, NH); 8.05-8.00 (m, 4H, 6+7+8+9); 3.52 (q, 2H, $^3$J=6.44 Hz, 3); 2.57 (qt, 2H, $^3$J$_{2-1}$=11.34 Hz, $^3$J$_{2-3}$=6.70 Hz, 2)

Compound 89: 3-(4-(3,3,3-trifluoropropylcarbamoyl)phenyl)-1,2,4-thiadiazole-5-ethyl carboxylate

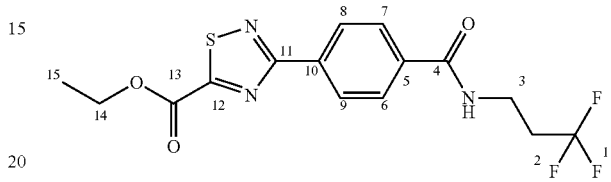

383 mL (10 eq.) ethyl cyanoformiate are added to a solution of 100 mg (1 eq.) 4-(2-oxo-1,3,4-oxathiazol-5-yl)-N-(3,3,3-trifluoropropyl)benzamide (85) in 400 µL 1,2-dichloro-benzene. The mixture is agitated during 30 min at 160° C. in a microwave reactor. The solution is cooled at AT and then 6 mL acetonitrile are then added. The formed precipitate is filtrated to yield 302 mg (85%) of white powder.

LC-MS: t$_R$=2.77 min (method c); m/z: [M+H]$^+$=374

NMR $^1$H (CD$_3$OD, 300 MHz): δ ppm=8.44 (d, 2H, $^3$J=8.56 Hz, 8+9); 7.97 (d, 2H, $^3$J=8.56 Hz, 6+7); 4.54 (q, 2H, $^3$J=7.16 Hz, 14); 3.66 (t, 2H, $^3$J=7.04 Hz, 3); 2.55 (qt, 2H, $^3$J$_{2-1}$=10.83 Hz, $^3$J$_{2-3}$=7.04 Hz, 2); 1.47 (t, 3H, $^3$J=7.13 Hz, 15)

Compound 90: 4-(5-(hydroxymethyl)-1,2,4-thiadiazol-3-yl)-N-(3,3,3-trifluoropropyl)-benzamide

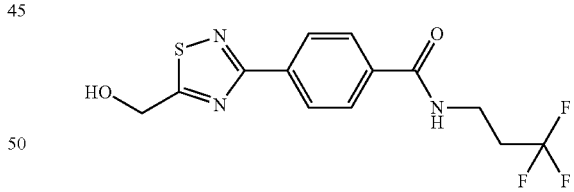

550 µL of a solution 2M of LiBH$_4$ in the THF are added at 0° C. and under argon to a solution of 140 mg 3-(4-(3,3,3-trifluoropropylcarbamoyl)phenyl)-1,2,4-thiadiazole-5-ethyl carboxylate (89) in 3.5 mL anhydrous THF. The solution is agitated during 30 min at 0° C. 0.5 mL of an aqueous solution saturated with NH$_4$Cl are then added to neutralize the excess of hydride. The medium is concentrated under reduced pressure. The residue thus obtained is then purified on a pre-packed silica column (Toluene 97:3 MeOH Toluene 95:5 MeOH) to yield 108 mg (44%) of white powder.

LC-MS: t$_R$=2.18 min (method c); m/z: [M+H]$^+$=332, [M−H]$^-$=330

Compound 92: 4-azido-N-(3,3,3-trifluoropropyl)benzamide

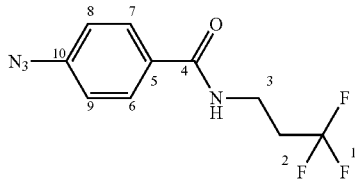

1.05 g (1 eq.) 3,3,3-trifluoropropylamine hydrochloride are added to a solution of 1.14 g (1 eq.) 4-azidobenzoic acid, 536 mg (0.5 eq) HOBt 3.19 g (1.2 eq) HBTU and 4.85 mL (4 eq.) DIEA in 5 mL DMF. The solution is agitated one night at AT and then evaporated under reduced pressure. The residue is dissolved in the ethyl acetate and washed with an aqueous solution saturated with NaHCO$_3$ (2×), an aqueous solution of HCl 1N (1×) and in brine (1×). The organic phase is dried on magnesium sulfate and then evaporated under reduced pressure to yield 1.77 g (98%) of a light brown solid.

LC-MS: $t_R$=2.65 min (method c); m/z: [M−H]$^-$=257

NMR $^1$H (CD$_3$OD, 300 MHz): δ ppm=7.86 (d, 2H, $^3$J=8.91 Hz, 6+7 or 8+9); 7.15 (d, 2H, $^3$J=8.92 Hz, 6+7 or 8+9); 3.61 (t, 2H, $^3$J=6.97 Hz, 3); 2.51 (qt, =10.99 Hz, $^3$J$_{2-3}$=7.05 Hz, 2)

Procedure (ii): General Procedure for Forming Triazole by "Click Chemistry"

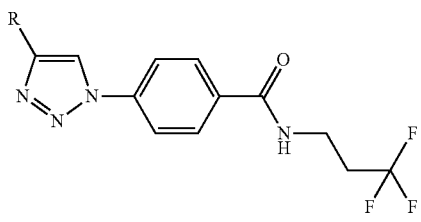

1 eq. alkyne is added to a solution of 115 mg (1 eq.) 4-azido-N-(3,3,3-trifluoropropyl)benzamide (92), 8 mg (0.1 eq.) CuSO$_4$, 99.1 mg (1 eq.) sodium ascorbate in 6 mL of a mixture t-BuOH/H$_2$O (1/1). The solution is agitated one night at AT.

Compound 93: 4-(4-isopentyl-1H-1,2,3-triazol-1-yl)-N-(3,3,3-trifluoropropyl)benzamide

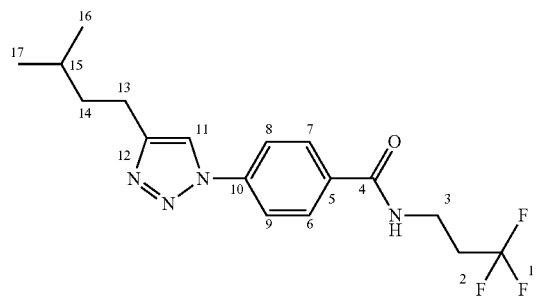 [SMILES: CC(C)CCc1cn(-c2ccc(C(=O)NCCC(F)(F)F)cc2)nn1]

Procedure (ii) with 65.7 μL 5-methylhexyne. The medium is filtrated after reaction. The product still present in the aqueous phase is extracted using ethyl acetate. The product is then dried in a desiccator to yield 93 mg (53%) of beige solid.

LC-MS: $t_R$=2.93 min (method c); m/z: [M+H]$^+$=355

NMR $^1$H (DMSO-d$_6$, 300 MHz): δ ppm=8.84 (br s, 1H, NH); 8.69 (s, 1H, 11); 8.03 (br m, 4H, 6+7+8+9); 3.53 (q, 2H, $^3$J=6.34 Hz, 3); 2.73 (t, 2H, $^3$J=7.42 Hz, 13); 2.58 (qt, $^3$J$_{2-1}$=11.40 Hz, $^3$J$_{2-3}$=7.11 Hz, 2); 1.67-1.54 (m, 3H, 14+15); 0.94 (d, 6H, $^3$J=6.13 Hz, 16+17)

Compound 94: 4-(4-isobutyl-1H-1,2,3-triazol-1-yl)-N-(3,3,3-trifluoropropyl)benzamide

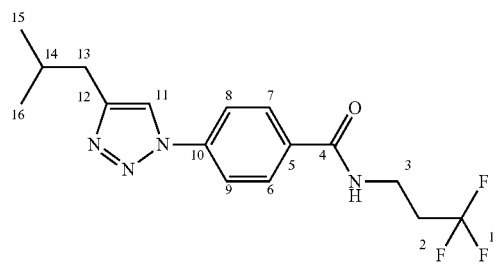

Procedure (ii) with 58.9 μL 4-methylpentyne. After one night, the conversion is not total. 1 eq. alkyne, 0.5 eq. sodium ascorbate and 0.05 eq. CuSO$_4$ are added to the reaction medium. The solution is agitated during 4 h at AT. The product is extracted using ethyl acetate. The organic phases are collected, dried on magnesium sulfate and then evaporated under reduced pressure to yield 128 mg (75%) of a light brown powder.

LC-MS: $t_R$=2.77 min (method c); m/z: [M+H]$^+$=341

NMR $^1$H (DMSO-d$_6$, 300 MHz): δ ppm=8.42 (s, 1H, 11); 8.05-7.97 (m, 4H, 6+7+8+9); 3.65 (t, 2H, $^3$J=6.98 Hz, 3); 2.67 (d, 2H, $^3$J=6.85 Hz, 13); 2.55 (qt, $^3$J$_{2-1}$=10.93 Hz, $^3$J$_{2-3}$=6.93 Hz, 2); 2.03 (n, 1H, $^3$J=6.75 Hz, 14); 0.99 (d, 6H, $^3$J=6.63 Hz, 15+16)

Compound 95: 4-(4-cyclopropyl-1H-1,2,3-triazol-1-yl)-N-(3,3,3-trifluoropropyl)-benzamide

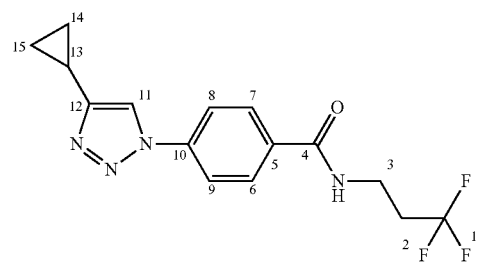 [SMILES: O=C(NCCC(F)(F)F)c1ccc(-n2cc(C3CC3)nn2)cc1]

Procedure (ii) with 42.4 μL ethynylcyclopropane. Part of the product is recovered by filtration of the formed precipitate. The remaining product in the filtrate is extracted using ethyl acetate. The organic phases are collected, dried on magnesium sulfate and then evaporated under reduced pressure to yield 73 mg (45%) of a white powder.

LC-MS: $t_R$=2.52 min (method c); m/z: [M+H]$^+$=325

NMR $^1$H (DMSO-d$_6$, 300 MHz): δ ppm=8.84 (br s, 1H, NH); 8.64 (s, 1H, 11); 8.05-7.97 (m, 4H, 6+7+8+9); 3.53 (q, 2H, $^3$J=6.44 Hz, 3); 2.58 (qt, 2H, $^3$J$_{2-1}$=11.51 Hz, $^3$J$_{2-3}$=6.95 Hz, 2); 2.09-2.00 (m, 1H, 13); 1.02-0.96+0.84-0.79 (m, 4H, 14+15)

Compound 96: 4-(4-(hydroxymethyl)-1H-1,2,3-triazol-1-yl)-N-(3,3,3-trifluoropropyl)-benzamide

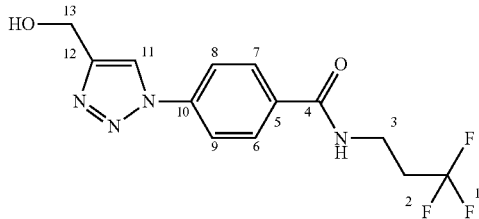 [SMILES: O=C(NCCC(F)(F)F)c1ccc(-n2cc(CO)nn2)cc1]

Procedure (ii) with 29.2 μL propargyl alcohol. The product is extracted using ethyl acetate. The organic phases are regrouped, dried on magnesium sulfate and then evaporated under reduced pressure to yield 52 mg (33%) of a beige powder.

LC-MS: t$_R$=2.03 min (method c); m/z: [M+H]$^+$=315

NMR $^1$H (CD$_3$OD, 300 MHz): δ ppm=8.57 (s, 1H, 11); 8.07-7.99 (m, 4H, 6+7+8+9); 4.79 (s, 2H, 13); 3.67 (t, 2H, $^3$J=6.97 Hz, 3); 2.57 (qt, 2H, $^3$J$_{2-1}$=10.91 Hz, $^3$J$_{2-3}$=6.98 Hz, 2)

NMR $^{13}$C (CD$_3$OD, 75 MHz): δ ppm=168.9 (4); 150.3 (12); 140.6 (5 or 10); 135.5 (5 or 10); 130.1 (6+7); 128.0 (q, $^1$J$_{C-F}$=276.1 Hz, 1); 122.3 (11); 121.2 (8+9); 56.4 (13); 34.6 (3); 34.0 (q, $^2$J$_{C-F}$=27.7 Hz, 2)

Compound 97: 4-(4-(2-hydroxyethyl)-1H-1,2,3-triazol-1-yl)-N-(3,3,3-trifluoropropyl)-benzamide

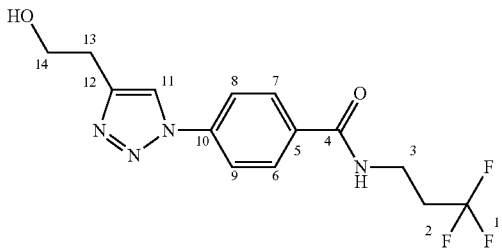 [SMILES: O=C(NCCC(F)(F)F)c1ccc(-n2cc(CCO)nn2)cc1]

Procedure (ii) with 37.9 μL 3-butyn-1-ol. No precipitate is observed. The product is extracted using ethyl acetate. The organic phases are collected, dried on magnesium sulfate and then evaporated under reduced pressure to yield 135 mg (82%) of beige solid.

LC-MS: t$_R$=2.07 min (method c); m/z: [M+H]$^+$=329

NMR $^1$H (CD$_3$OD, 300 MHz): δ ppm=8.44 (s, 1H, 11); 8.04-7.96 (m, 4H, 6+7+8+9); 3.89 (t, 2H, $^3$J=6.62 Hz, 14); 3.65 (t, 2H, $^3$J=6.98 Hz, 3); 3.00 (t, 2H, $^3$J=6.51 Hz, 13); 2.44 (qt, 2H, $^3$J$_{2-1}$=10.85 Hz, $^3$J$_{2-3}$=7.09 Hz, 2)

NMR $^{13}$C (CD$_3$OD, 75 MHz): δ ppm=168.9 (4); 147.3 (12); 140.7 (5 or 10); 135.4 (5 or 10); 130.1 (6+7); 128.0 (q, $^1$J$_{C-F}$=275.8 Hz, 1); 122.2 (11); 121.1 (8+9); 61.9 (14); 34.6 (3); 34.0 (q, $^2$J$_{C-F}$=28.1 Hz, 2); 29.9 (13)

Compound 98: 4-(4-(2-hydroxypropan-2-yl)-1H-1,2,3-triazol-1-yl)-N-(3,3,3-trifluoro-propyl)benzamide

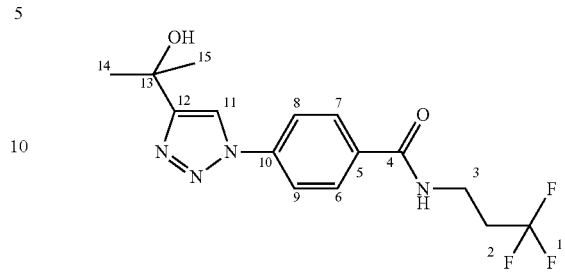

Procedure (ii) with 48.9 μL 2-methyl-3-butyn-2ol. Part of the product is recovered by filtration of the formed precipitate. The remaining product in the filtrate is extracted using ethyl acetate. The organic phases are collected, dried on magnesium sulfate and then evaporated under reduced pressure. The product is dried in a desiccator to yield 80 mg (53%) of white powder.

LC-MS: t$_R$=2.18 min (method c); m/z: [M–H]$^-$=341

NMR $^1$H DMSO-d$_6$ 300 MHz): δ ppm=8.84 (t, 1H, $^3$J=5.18 Hz, NH); 8.71 (s, 1H, 11); 8.08-8.01 (m, 4H, 6+7+8+9); 5.29 (s, 1H, OH); 3.53 (q, 2H, $^3$J=6.40 Hz, 3); 2.58 (qt, 2H, $^3$J$_{2-1}$=11.53 Hz, $^3$J$_{2-3}$=6.72 Hz, 2)

Compound 99: 1-(4-(3,3,3-trifluoropropylcarbamoyl)phenyl)-1H-1,2,3-triazole-4-methyl carboxylate

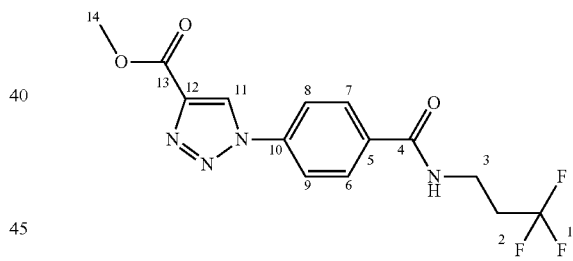

Procedure (ii) with 41.4 μL methyl propiolate. After one night, the conversion is not total. 0.5 eq. alkyne, 0.5 eq. sodium ascorbate and 0.05 eq. CuSO$_4$ are added to the reaction medium. The solution is agitated during 4 h at AT. The product is extracted using ethyl acetate. The organic phases are collected, dried on magnesium sulfate and then evaporated under reduced pressure to yield 156 mg (91%) of a beige powder.

LC-MS: t$_R$=2.37 min (method c); m/z: [M+H]$^+$=343

NMR $^1$H (DMSO-d$_6$, 300 MHz): δ ppm=9.62 (s, 1H, 11); 8.89 (t, 1H, $^3$J=5.56 Hz, NH); 8.14 (d, 2H, $^3$J=8.88 Hz, 8+9); 8.06 (d, 2H, $^3$J=8.88 Hz, 6+7); 3.91 (s, 3H, 14); 3.54 (q, $^3$J=6.46 Hz, 3); 2.59 (qt, 2H, $^3$J$_{2-1}$=11.44 Hz, $^3$J$_{2-3}$=7.06 Hz, 2)

NMR $^{13}$C (DMSO-d$_6$, 75 MHz): δ ppm=165.1 (13); 160.5 (4); 139.7 (12); 138.0 (5 or 10); 134.5 (5 or 10); 128.9 (6+7); 127.5 (11); 126.9 (q, $^1$J$_{C-F}$=277.1 Hz, 1); 120.2 (8+9); 52.1 (14); 32.9 (3); 32.4 (q, $^2$J$_{C-F}$=26.6 Hz, 2)

Compound 100: 4-(3,3,3-trifluoropropylcarbamoyl)methyl benzimidate hydrochloride

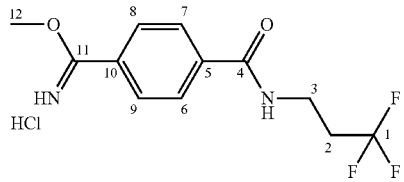

15 mL of a solution of hydrochloric acid 4N in dioxane are added under argon at 0° C. to a solution of 300 mg 4-cyano-N-(3,3,3-trifluoropropyl)benzamide (73) in 1 mL MeOH. The mixture is agitated during one night at AT. 20 mL diethyl ether are added and the solution is cooled in a refrigerator during one hour. The precipitate is then filtrated, washed using diethyl ether and dried in a desiccator to yield 359 mg (93%) of white powder.

LC-MS: $t_R$=1.85 min (method c); m/z: [M+H]$^+$=275, [M−H]$^-$=273

Compound 101: 4-(5-methyl-4H-1,2,4-triazol-3-yl)-N-(3,3,3-trifluoropropyl)benzamide

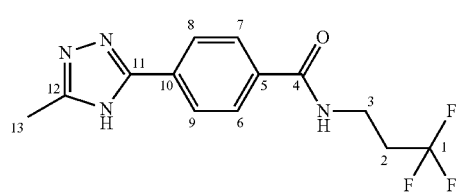

169 μL (1.5 eq.) DIEA are added to a solution of 200 mg 4-(3,3,3-trifluoropropylcarbamoyl) methyl benzimidate hydrochloride (100) in 5 mL absolute ethanol. The reaction medium is agitated during 15 min at AT. The acetylhydrazine is then added and the solution is agitated during 60 h under reflux. The ethanol is evaporated under reduced pressure. The solid rose thus obtained is purified by preparative HPLC and then lyophilized to yield 123 mg (64%) of white powder.

LC-MS: $t_R$=1.92 min (method c); m/z: [M+H]$^+$=299, [M−H]$^-$=297

NMR $^1$H (CD$_3$OD, 300 MHz 8.08 (d, 2H, $^3$J=8.59 Hz, 8+9); 7.90 (d, 2H, $^3$J=8.68 Hz, 6+7); 3.64 (t, 2H, $^3$J=7.02 Hz, 3); 2.62-2.46 (m, 5H, 13+2)

Scheme 14:

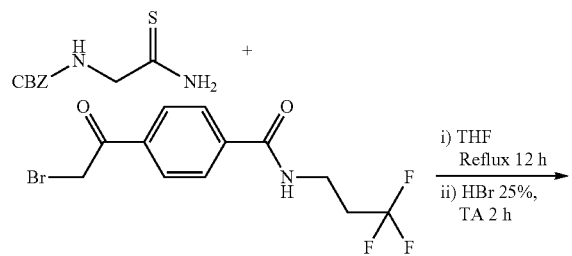

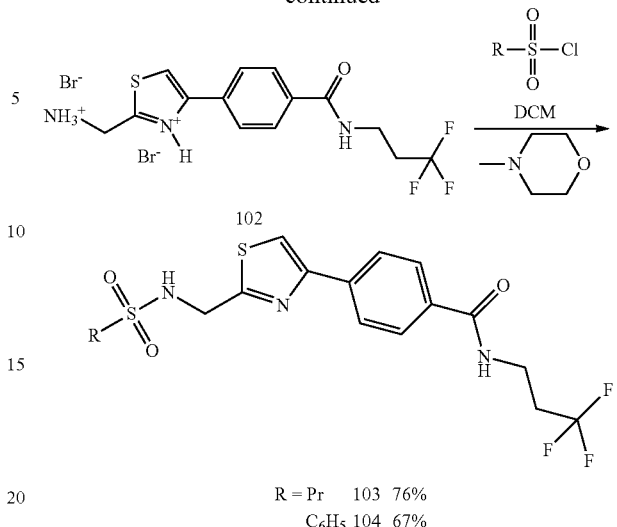

R = Pr  103  76%
C$_6$H$_5$  104  67%

Compound 102: (4-(4-(3,3,3-trifluoropropylcarbamoyl)phenyl)thiazol-2-yl) methanaminium di-bromhydrate

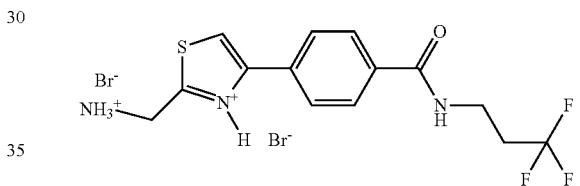

73 mg (1.1 eq.) N-benzyloxycarbonylglycine thioamide are added to a solution of 100 mg (1 eq.) 4-(2-bromoacetyl)-N-(3,3,3-trifluoropropyl)benzamide (46) in 5 mL anhydrous THF. The solution is agitated during 3 h at 70° C. The THF is then evaporated under reduced pressure and the solid thus obtained is used as is 1 mL of a HBr solution at 25% in the acetic acid is added and the reaction medium is agitated during 1 h at AT 8 mL diethyl ether are then added at AT to form a precipitate that is cooled in an ice-water bath. The precipitate is then filtrated, washed using cold diethyl ether and then dried in a desiccator to yield 157 mg of pale brown solid. The product is separated in two for the synthesis of the compounds 103 and 104.

LC-MS: $t_R$=1.85 min (method c); m/z: [M+H]$^+$=330

Compound 103: 4-(2-(propylsulfonamidomethyl)thiazol-4-yl)-N-(3,3,3-trifluoropropyl)benzamide

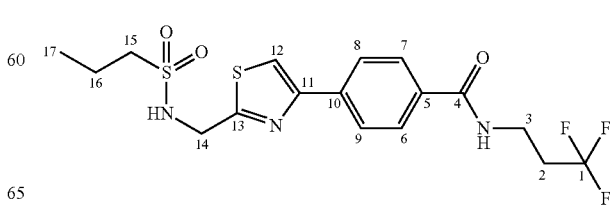

20 μL (1.2 eq.) propane sulfonic acid chloride are added to a solution of 75 mg (1 eq.) of compound 102 and 82 μL N-methylmorpholine in 1.5 mL anhydrous DCM. The reaction medium is agitated during 2 h at AT. The DCM is evaporated under reduced pressure and then the residue is taken over in the ethyl acetate and then washed using water (2×) and in brine (1×). The organic phase is dried on magnesium sulfate and then evaporated under reduced pressure to yield 54 mg (76%) of beige powder.

LC-MS: $t_R$=2.60 min (method c); m/z: [M−H]⁻=434

NMR ¹H (CD₃OD, 300 MHz): δ ppm: 8.05 (d, 2H, $^3J$=8.43 Hz, 8+9); 7.96 (s, 1H, 12); 7.89 (d, 2H, $^3J$=8.49 Hz, 6+7); 4.63 (s, 2H, 14); 3.66, (t, 2H, $^3J$=6.99 Hz, 3); 3.15-3.09 (m, 2H, 15); 2.56 (qt, 2H, $^3J_{2-1}$=10.89 Hz, $^3J_{2-3}$=7.11 Hz, 2); 1.84 (sx, 2H, $^3J$=7.60 Hz, 16); 1.04 (t, 3H, $^3J$=7.46 Hz, 17).

Compound 104: 4-(2-(phenylsulfonamidomethyl) thiazol-4-yl)-N-(3,3,3-trifluoro-propyl)benzamide

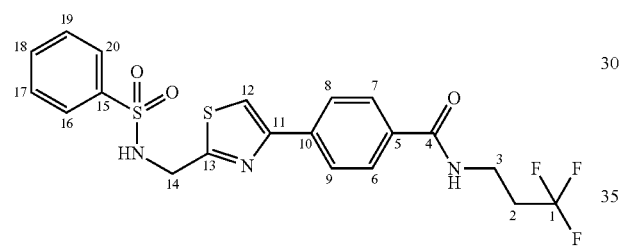

23 μL (1.2 eq.) benzene sulfonic acid chloride are added to a solution of 75 mg (1 eq.) of compound 102 and 82 μL N-methylmorpholine in 1.5 mL anhydrous DCM. The reaction medium is agitated during 2 h at AT. The DCM is evaporated under reduced pressure and then the residue is taken over in the ethyl acetate and then washed using water (2×) and in brine (1×). The organic phase is dried on magnesium sulfate and then evaporated under reduced pressure to yield 51 mg (67%) of beige powder.

LC-MS: $t_R$=2.73 min (method c); m/z: [M−H]⁻=468

NMR ¹H (CD₃OD, 300 MHz): δ ppm=7.96 (d, $^3J$=8.50 Hz, 8+9); 7.87 (m, 5H, 6+7+12+16+20); 5.57 (m, 3H, 17+18+19); 4.47 (s, 2H, 14); 3.65 (t, 2H, $^3J$=7.00 Hz, 3); 2.55 (qt, 2H, $^3J_{2-1}$=11.0 Hz, $^3J_{2-3}$=7.10 Hz, 2)

Scheme 15:

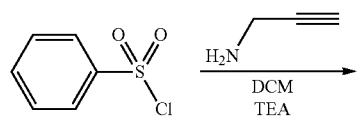

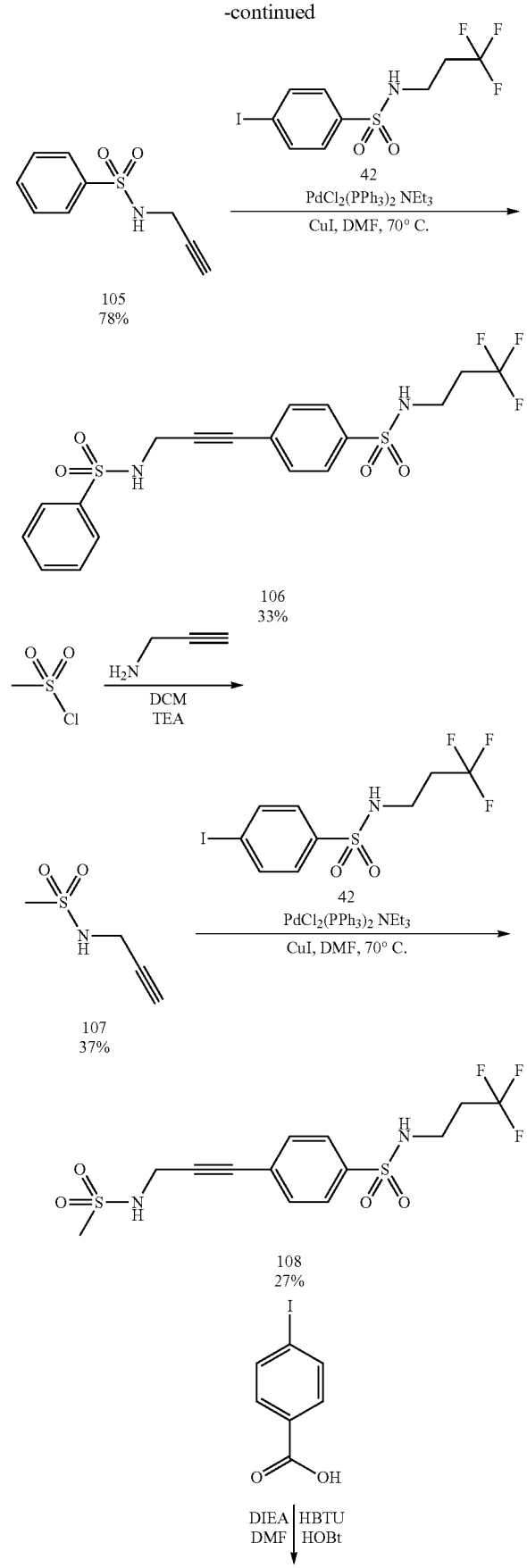

-continued

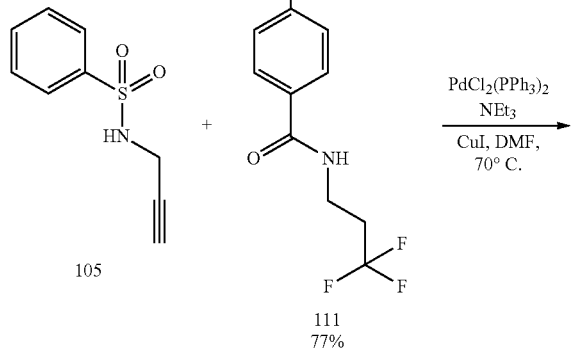

111
77%

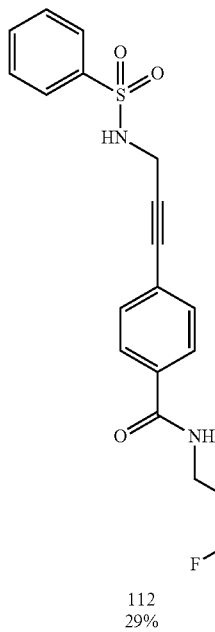

112
29%

Compound 105: N-(prop-2-ynyl)benzene sulfonamide

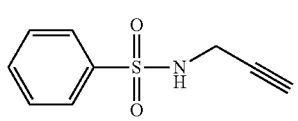

200 μL (1 eq.) benzene sulfonic acid chloride, 129 μL (1.2 eq.) propargylamine, 8 mL DCM and 1.08 mL (4 eq.) DIEA are agitated at AT during 2 h. The DCM is evaporated under reduced pressure and then the residue is taken over in the ethyl acetate, washed in water (2×) and in brine (1×). The organic phase is dried on magnesium sulfate and then evaporated under reduced pressure. The residue is purified by preparative HPLC to yield 238 mg (78%) of a transparent oil.

LC-MS: $t_R$=2.42 min (method c); m/z: [M−H]⁻=194
CCM: $R_f$=0.14 (AcOEt 2:8 Cyclohexane)

Compound 106: 4-(3-(phenylsulfonamido)prop-1-ynyl)-N-(3,3,3-trifluoropropyl)-benzene sulfonamide

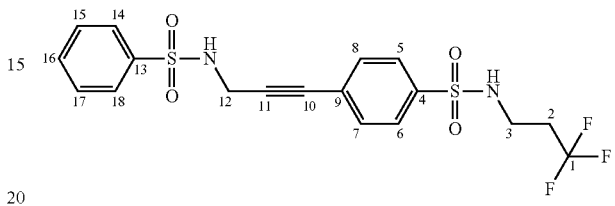

50 mg (1 eq.) N-(prop-2-ynyl)benzene sulfonamide (105), 87 mg (0.9 eq.) 4-iodo-N-(3,3,3-trifluoropropyl)benzene sulfonamide (42), 8.3 mg (0.05 eq.) bis(triphenylphosphine)palladium(II) chloride, 40.2 mg (0.9 eq.) copper iodide, and 120 μL (0.5 mL/mmol) triethylamine are placed successively in a schlenk under an argon flow. The anhydrous DMF is added via a cannula under argon at ambient temperature. The reaction mixture is agitated at 70° C. under argon during 48 h.

The reaction medium is then diluted at AT by adjunction of a mixture of AcOEt:NH₄Cl$_{sat}$ (1:1). The formed precipitate is filtrated and washed using ethyl acetate. The organic phase is washed with an aqueous solution saturated with NH₄Cl (2×) and then in brine (1×), dried on magnesium sulfate, filtrated on celite and then evaporated under reduced pressure. The solid orange thus obtained is solubilized in the minimum of acetonitrile and then the product is precipitated by adjunction of diisoprpylic ether and filtrated to yield 38 mg (33%) of beige powder.

LC-MS: $t_R$=3.13 min (method c); m/z
NMR ¹H (CD₃OD, 300 MHz): δ ppm=7.92 (m, 2H, 14+18 or 15+17); 7.74 (d, 2H, ³J=8.40 Hz, 5+6); 7.50-7.57 (m, 3H, 16+(14+18 or 15+17)); 7.30 (d, 2H, ³J=8.40 Hz, 7+8); 4.07 (s, 2H, 12); 3.08 (t, 2H, ³J=7.10 Hz, 3); 2.36 (qt, 2H, ³J$_{2-1}$=10.60 Hz, ³J$_{2-3}$=6.80 Hz, 2)
NMR ¹³C (CD₃OD, 75 MHz): δ ppm=142.3 (4); 141.2 (13); 133.7 (16); 133.2 (7+8); 130.1 (14+18ou15+17); 128.4 (14+18ou15+17); 128.3 (9); 127.9 (5+6); 127.5 (q, ¹J=276.7 Hz, 1); 88.7 (11); 83.3 (10); 37.4 (3); 35.2 (q, ²J=28.2 Hz, 2); 33.8 (12)

Compound 107: N-(prop-2-ynyl)methane sulfonamide

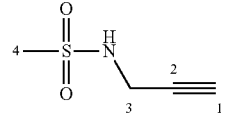

A solution of 288 μL (1 eq.) methane sulfonic acid chloride in 3 mL diethyl ether is added to a solution of 500 μL (2 eq.) propargylamine in 6 mL diethyl ether cooled at 0°

C. The mixture is agitated during 30 min. The formed precipitate is filtrated and washed twice using ether. The filtrate is evaporated under reduced pressure to yield 178 mg (37%) of a white solid.

LC-MS: $t_R$=1.92 min (method c); m/z: [M+H]$^+$=134
NMR $^1$H (CDCl$_3$ 300 MHz): δ ppm=4.69 (m, 1H, NH); 4.00 (dd, 2H, $^3J_{3\text{-}NH}$=6.20 Hz, $^4J_{3\text{-}1}$=2.50 Hz, 2); 3.10 (s, 3H, 4); 2.41 (t, 1H, $^3J$=2.50 Hz, 1)

Compound 108: 4-(3-(methylsulfonamido)prop-1-ynyl)-N-(3,3,3-trifluoropropyl)-benzene sulfonamide

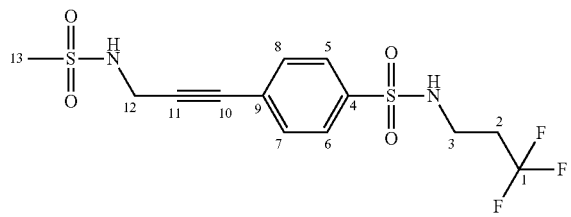 [SMILES: CS(=O)(=O)NCC#Cc1ccc(S(=O)(=O)NCCC(F)(F)F)cc1]

136 mg (1.2 eq.) tetrabutylammonium acetate, 1 mg (0.002 eq.) Pd EnCat$^{30}$, 142 mg (1 eq.) 4-iodo-N-(3,3,3-trifluoropropyl)benzene sulfonamide (42) and 50 mg (1 eq.) N-(prop-2-ynyl)methane sulfonamide (107) are added to 500 μL DMF. The solution is agitated during 24 h at 80° C. A mixture of AcOEt:NH$_4$Cl$_{sat}$ 1:1 (2 mL) is added to the reaction medium. The mixture is agitated for 10 min and then filtrated to recover the palladium beads. The product is recovered in the organic phase by extraction Water:AcOEt. The organic phase is then washed in brine (1×), dried on magnesium sulfate, filtrated on celite and evaporated under reduced pressure. The product is purified on a pre-packed silica column (Cyclohexane 95:5 Isopropanol→Cyclohexane 90:10 Isopropanol). 39 mg (27%) of a beige solid are recovered.

LC-MS: $t_R$=2.78 min (method c); m/z: [M+H]$^+$=385
NMR $^1$H (CD$_3$OD, 300 MHz): δ ppm=7.84 (d, 2H, $^3J$=8.59 Hz, 5+6 or 7+8); 7.64 (d, 2H, $^3J$=8.59 Hz, 5+6 or 7+8); 4.17 (s, 2H, 12); 3.12-3.08 (m, 5H, 13+3); 2.38 (qt, 2H, $^3J_{2\text{-}1}$=10.78 Hz, $^3J_{2\text{-}3}$=7.28 Hz, 2)

Compound 111: 4-iodo-N-(3,3,3-trifluoropropyl)benzamide

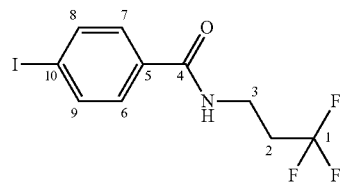

300 mg (1 eq.) 4-acetylbenzoic acid, 181 mg (1 eq.) 3,3,3-trifluoropropylamine hydrochloride, 33 mg (0.2 eq.) HOBT, 551 mg (1.1 eq.) HBTU and 10 mL DMF are successively added in a 25 mL flask. 840 μL (4 eq.) DIEA are then added and the mixture is agitated 2 h at AT The DMF is evaporated under reduced pressure. The residue is taken over in the ethyl acetate and then washed in brine (2×). The organic phase is then evaporated under reduced pressure and the product is then purified on a pre-packed silica column (Cyclohexane 8:2 AcOEt) to yield 327 mg (77%) of white powder.

LC-MS: $t_R$=3.25 min (method c); m/z: [M+H]$^+$=344
NMR $^1$H (CDCl$_3$ 300 MHz): δ ppm=7.80 (d, 2H, $^3J$=8.50 Hz); 7.47 (d, $^3J$=8.50 Hz); 6.34 (m, 1H, NH); 3.72 (q, 2H, $^3J$=6.30 Hz, 3); 2.47 (tq, 2H, $^3J_{2\text{-}1}$=10.70 Hz, $^3J_{2\text{-}3}$=6.40 Hz, 2)
NMR $^{19}$F CDCl$_3$ 282.4 MHz): δ ppm=−64.92 (t, $^3J$=10.8 Hz)

Compound 112: 4-(3-(phenylsulfonamido)prop-1-ynyl)-N-(3,3,3-trifluoropropyl)-benzamide

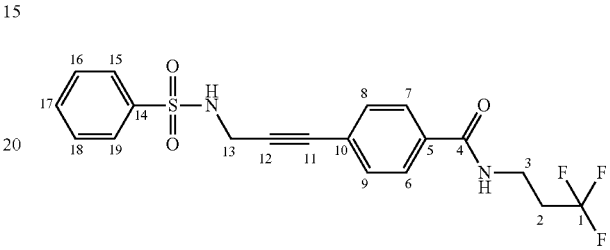

50 mg (1 eq.) N-(prop-2-ynyl)benzene sulfonamide (105), 83.5 mg (0.95 eq.) 4-iodo-N-(3,3,3-trifluoropropyl)benzamide (111), 9 mg (0.05 eq.) bis(triphenylphosphine)palladium(II) chloride, 48 mg (1 eq.) copper iodide, and 128 μL (0.5 mL/mmol) triethylamine are placed successively in a schlenk under argon flow. 1 mL anhydrous DMF is added via a cannula under argon at AT. The reaction mixture is agitated at 70° C. under argon during 48 h. The reaction medium is diluted at AT by adjunction of a mixture of 1:1 AcOEt:NH$_4$Cl$_{sat}$. The precipitate thus formed is filtrated and washed using ethyl acetate. An extraction is performed using a mixture AcOEt:NH$_4$Cl$_{sat}$. The organic phase is washed in brine (1×), dried on magnesium sulfate, filtrated on celite and then evaporated under reduced pressure. The brown oil thus obtained is purified by pre-packed silica column (DCM 95:5 AcOEt) to yield 30 mg (29%) of a light brown solid.

LC-MS: $t_R$=5.43 min (method d); m/z: [M+H]$^+$=411
NMR $^1$H (CD$_3$OD, 300 MHz): δ ppm=7.94 (dd, 2H, $^3J$=7.40 Hz, $^4J$=1.60 Hz, 15+19); 7.71 (d, 2H, $^3J$=8.40 Hz, 6+7 or 8+9); 7.55 (m, 3H, 16+17+18); 7.21 (d, 2H, $^3J$=8.40 Hz, 6+7 or 8+9); 4.07 (s, 2H, 13); 3.62 (t, 2H, $^3J$=7.00 Hz, 3); 2.52 (qt, 2H, $^3J_{2\text{-}1}$=10.90 Hz, $^3J_{2\text{-}3}$=7.00 Hz, 2);

Evaluation of the Compounds' Activity
TSA Test (Thermal Shift Assay)

The heat denaturation of proteins is a phenomenon that has been studied for a long time, by means of many techniques, based notably on calorimetry (DSC: Differential Scanning calorimetry) or fluorescence (DSF: Differential Scanning Fluorimetry or also Fluorescence Thermal Shift Assay).

The Thermal Shift Assay test uses a fluorescent marker, in our case Sypro Orange™. The fluorescence intensity of this compound is amplified when it is in a hydrophobic environment. Thus, in normal conditions, in an aqueous solution and in the presence of the native protein, the marker fluoresces little, as the hydrophobic zones of the protein are not accessible. When the protein becomes denatured under the effect of heat, the marker will be able to interact with its hydrophobic regions, causing an increase in fluorescence. It is thus possible to determine the melting temperature of the protein, denoted by $T_m$, corresponding to a state where the protein is 50% denatured.

This technique enables the stabilizing or destabilizing effect on the protein of a specific ligand to be measured. For this, the experience is carried out with the protein alone and then by incubating the protein with a potential ligand. Two different values for the melting temperature are then obtained that enable a temperature difference $\Delta T_m$ expressed in $°$ C. to be defined. If $\Delta T_m > 0$, the ligand stabilizes the protein, if $\Delta T_m < 0$, the ligand destabilizes the protein. The greater $|\Delta T_m|$, the greater the ligand's stabilizing or destabilizing effect. Yet as the stabilizing power is linked to the ligand's affinity for the protein, the higher the $\Delta T_m$ is, the greater the ligand's affinity for this protein.

This TSA fluorescence test thus enables the affinity of our ligands for the EthR protein to be quantified and for them to, be classified according to their ascending $\Delta T_m$ value.

Surface Plasmon Resonance test (SPR) (described in the article "*Ethionamide Boosters Combining Bioisosteric Replacement and Structure-Based Drug Design to Solve Pharmacokinetic Issues in a series of potent 1,2,4-Oxadiazole EthR Inhibitors*" published in 2012 in the *Journal of Medicinal Chemistry*)

After having measured the ligands' affinity for the protein, it is necessary to verify that this does indeed result in the inactivation of the transcriptional repressor, thus preventing it from binding to its operon. For this, a functional test based on the principle of surface plasmon resonance is used. Surface Plasmon Resonance (SPR) makes it possible to visualize in real time the phenomena of association or dissociation between a partner immobilized on a biosensor and, a second partner injected in a continuous flow onto this surface. In the present case, the SPR technique enables the interaction between the EthR protein (analyte injected in continuous flow) and the ethA gene promoter (partner immobilized on the surface) to be visualized. Two cells are used for the test: a measuring cell onto which the so-called relevant DNA is affixed, i.e. corresponding to the ethA gene promoter, and a control cell on which is a non-relevant (thus different) DNA strand of same length, enabling the non-specific protein/DNA interactions to be removed. In a first step, the EthR protein is injected alone, until saturation, which enables a signal $SI_{EthR}$ corresponding to the quantity of EthR protein that has come to bind to the DNA to be measured. In a second step, the experience is reiterated in the presence of a potential ligand at different concentrations. If the compound binds to the EthR, thus preventing it from coming to bind on the DNA, a diminution of the response of the dose-dependent signal ($SI_{EthR+lig}$) is observed.

By using the equation hereafter, it is possible to calculate for each concentration a percentage for the inhibition of the ligand under examination:

$$\%Inhibition = 100 \times \frac{SI_{EthR} - SI_{EthR+Lig}}{SI_{EthR}}$$

By representing the variation of the inhibition percentage depending on the ligand concentration, a value for $IC_{50}$ can be deduced.

Potentiation of Ethionamid cell test (described in the article "*Ethionamide Boosters Combining Bioisosteric Replacement and Structure-Based Drug Design to Solve Pharmacokinetic Issues in a series of potent 1,2,4-Oxadiazole EthR Inhibitors*" published in 2012 in the *Journal of Medicinal Chemistry*)

The preceding test validates the, compounds' capacity to inhibit the EethR/DNA interaction by binding to the EthR protein. The third test used makes it possible to ascertain that these compounds are capable of potentiating the bactericide activity of ethionamide on *M. tuberculosis* alone or on macrophages infected by *M. tuberculosis*. This test is a "High Content Screening" (HCS) or dense content screening test. HCS tests are performed on cell cultures that enable certain phenotypic features of a microorganism (e.g. a bacterium) in a given environment to be studied. The phenotypic changes observed can range from the increase (or decrease) of the production of certain marked proteins to the modification of the morphology of the microorganism under consideration.

This test aims to determine the ligand concentration necessary to potentiate ten times the activity of ethionamide (ETH).

To measure, the ligand concentration necessary for potentiating ten times the activity of ETH, a constant concentration of ethionamide (0.1 µg/mL corresponding to $\frac{1}{10}^{th}$ of its $CMI_{99}$) is chosen. By varying the ligand concentration, the concentration necessary to inhibit 50% of the bacterial growth, i.e. the concentration necessary to potentiate ten times the activity of ethionamide, can be determined. This concentration will be denoted $EC_{50}$.

Measurement of the Solubility

40 µL of a solution at 10 mM in DMSO of the sample are added at 1.96 mL MeOH or PBS at pH 7.4. The samples are then agitated during 24 h at AT, centrifuged during 5 min and then filtrated on filters of 0.45 µm size. 20 µL of each solution are then added to 180 µL MeOH and then analyzed by LC-MS. The solubility is determined as ratio of the surfaces of the mass signals PBS/MeOH.

Measurement of the log D

40 µL of a solution at 10 mM in the DMSO of the sample are added to 1.96 mL of a mixture of 1/1 octanol/PBS at pH 7.4. The solution is agitated during 2 h at AT. 20 µL of each phase are added to 180 µL MeOH and analyzed by LC-MS. Each compound is evaluated in triplicate. The log D is determined as being the logarithm of the ratio of the product concentrations in the octanol and PBS phases, determined par the mass signals.

Measured Biological Activities

Each of the following tables consolidates the formulas of the tested compounds or the definitions of the different variable radicals mentioned in the Markush formula preceding the respective table and corresponding to the tested compounds as well as the values of $\Delta T_m$, $EC_{50}$ experimentally measured according to the aforementioned protocols and which corresponds to the number of atoms constituting each molecule and different from the hydrogen atom.

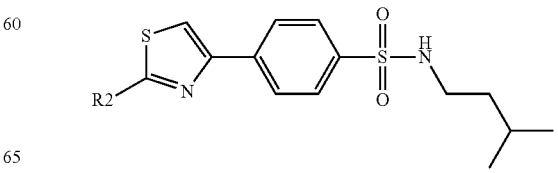

TABLE 1

| Compound | R2 | ΔT$_m$ (° C.) | EC$_{50}$ (μM) | HA |
|---|---|---|---|---|
| 6 | H$_3$C— | 6.1 | 5.7 | 21 |
| 17 | N≡C-CH$_2$— | 5.3 | 7.9 | 23 |
| 21 | H$_2$N-C(O)-CH$_2$— | 4.6 | 5.0 | 24 |

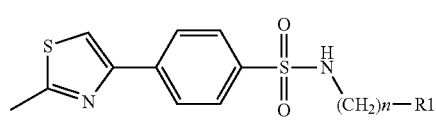

TABLE 2

| Compound | R1 | n | ΔT$_m$ (° C.) | EC$_{50}$ (μM) | HA |
|---|---|---|---|---|---|
| 6 | —CH(CH$_3$)$_2$ | 2 | 6.1 | 5.7 | 21 |
| 23 | —C(CH$_3$)$_3$ | 2 | 2.3 | >20 | 22 |
| 24 | —CF$_3$ | 2 | 8.5 | 0.29 | 22 |
| 25 | —CF$_2$CF$_3$ | 1 | 8.6 | >20 | 24 |
| 26 | —CF$_3$ | 1 | 6.3 | 7.9 | 21 |
| 27 | —CF$_3$ | 3 | 6.6 | >2.5 | 23 |
| 28 | —CF$_2$CF$_2$CF$_3$ | 1 | 7.3 | >2.5 | 27 |

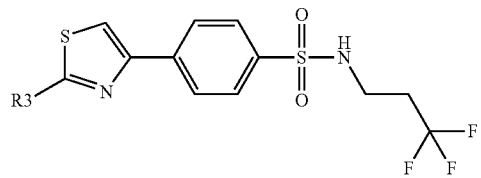

TABLE 3

| Compound | R3 | ΔT$_m$ (° C.) | EC$_{50}$ (μM) | HA |
|---|---|---|---|---|
| 24 | H$_3$C— | 8.5 | 0.29 | 22 |
| 33 | methyl ester-CH$_2$— | 9.5 | 0.86 | 26 |
| 34 | ethyl ester-CH$_2$— | 0.15 | 0.15 | 27 |
| 35 | isopropyl ester-CH$_2$— | 11.6 | 0.30 | 28 |
| 36 | isopropyl-NH-C(O)-CH$_2$— | — | 0.21 | 28 |
| 38 | isobutyl-CH$_2$-CH$_2$— | 12.4 | 0.39 | 27 |
| 39 | t-Bu-SO$_2$-CH$_2$— | 7.3 | 0.20 | 29 |

TABLE 4

| Compound | Structure | ΔT$_m$ (° C.) | EC$_{50}$ (μM) | HA |
|---|---|---|---|---|
| 41 | 4-methylthiazol-2-yl phenyl sulfonamide with CH$_2$CH$_2$CF$_3$ | 6.8 | 0.66 | 22 |
| 42 | benzothiazol-2-yl phenyl sulfonamide with CH$_2$CH$_2$CF$_3$ | — | 0.30 | 25 |

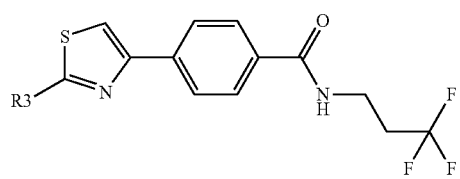

TABLE 5

| Compound | R3 | ΔT$_m$ (° C.) | EC$_{50}$ (μM) | HA |
|---|---|---|---|---|
| 43 | H3C— | 11.4 | 0.083 | 21 |
| 52 | ethyl ester group | 10.1 | 0.19 | 26 |
| 53 | isopropyl ester group | 13.2 | 0.33 | 27 |
| 50 | tert-butyl sulfone group | 9.6 | 0.041 | 28 |
| 103 | propyl sulfonamide group | 6.6 | 0.32 | 28 |
| 104 | phenyl sulfonamide group | 1.2 | 0.15 | 31 |
| 47 | isohexyl group | 13.0 | 0.030 | 26 |
| 54 | ethyl carbonate group | 9.6 | >2.5 | 25 |
| 55 | isopropyl carbonate group | 8.2 | 0.73 | 26 |
| 49 | isobutyl group | 12.6 | <0.040 | 24 |
| 56 | H | 8.1 | 0.36 | 20 |
| 57 | 4-pyridyl | 12.6 | <0.010 | 26 |

TABLE 5-continued

| Compound | R3 | ΔT$_m$ (° C.) | EC$_{50}$ (μM) | HA |
|---|---|---|---|---|
| 58 | 2-ethylpyridyl | 13.3 | <0.010 | 28 |

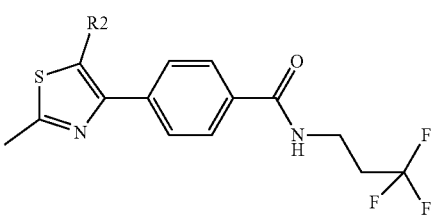

TABLE 6

| Compound | R2 | ΔT$_m$ (° C.) | EC$_{50}$ (μM) | HA |
|---|---|---|---|---|
| 62 | F | — | 0.055 | 22 |
| 64 | Cl | 8.7 | 0.35 | 22 |

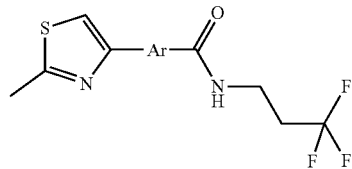

TABLE 7

| Compound | Ar | EC$_{50}$ (μM) | HA |
|---|---|---|---|
| 67 | pyridine | 0.120 | 21 |
| 71 | pyridine | 1.7 | 21 |

TABLE 8

| Compound | Structure | ΔT$_m$ (° C.) | EC$_{50}$ (μM) | HA |
|---|---|---|---|---|
| 92 | N3-substituted benzamide | 6.0 | 1.1 | 18 |

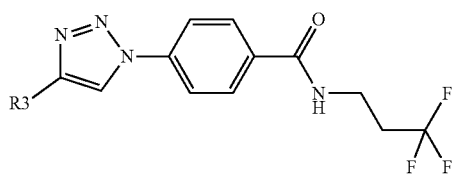

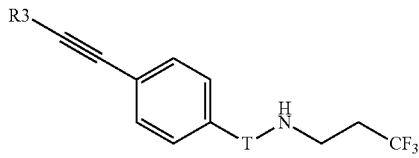

TABLE 9

| Compound | R3 | $\Delta T_m$ (° C.) | $EC_{50}$ (μM) | HA |
|---|---|---|---|---|
| 93 | (isopentyl) | 3.8 | >10 | 25 |
| 94 | (isobutyl) | 4.1 | 1.2 | 24 |
| 95 | (cyclopropylmethyl) | 3.5 | 1.7 | 23 |
| 97 | HO— | 1.2 | 2.0 | 23 |

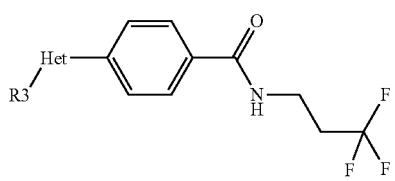

TABLE 10

| Compound | R3 | Het | $EC_{50}$ (μM) | HA |
|---|---|---|---|---|
| 72 | H₃C→ | oxazole | 0.18 | 21 |
| 75 | H₃C→ | oxadiazole | 0.062 | 21 |
| 78 | H₃C→ | oxadiazole | 0.21 | 21 |
| 80 | H₃C→ | oxadiazole | 0.96 | 21 |
| 83 | H₃C→ | thiadiazole | 1.4 | 21 |
| 90 | HO— | thiadiazole | 0.13 | 22 |

TABLE 11

| Compound | R3 | T | $\Delta T_m$ (° C.) | $EC_{50}$ (μM) | HA |
|---|---|---|---|---|---|
| 106 | PhSO₂NH— | SO₂ | 3.3 | 1.8 | 29 |
| 108 | MeSO₂NH— | SO₂ | 1.4 | >10 | 24 |
| 112 | PhSO₂NH— | CO | 4.2 | 0.23 | 28 |

TABLE 12

| Compound | $IC_{50}$ (μM) | Solubilité (μM) | LogD |
|---|---|---|---|
| 6 | 4.9 ± 0.1 | 20 | 3.55 |
| 24 | 0.55 ± 0.02 | 41.4 | 3.12 |
| 35 | — | 2.8 | 3.76 |
| 38 | — | <1 | >4 |
| 43 | 0.48 ± 0.06 | 46.9 | 2.82 |
| 49 | 0.44 ± 0.01 | 4.4 | 3.91 |
| 57 | — | 29 | 3.07 |
| 58 | — | 3.3 | 3.95 |

The invention claimed is:

1. A compound of formula (II):

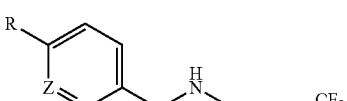

(II)

in which
Y and Z are CH;
T is chosen from CO or SO₂;
n is an integer greater than or equal to 1 and lower than or equal to 3;
R is R-7:

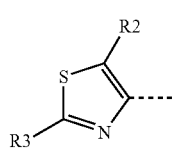

(R-7)

in which:

R2 is chosen from H, F, Cl, Br, I;

R3 is a group chosen from H, linear or branched C1-C6 alkyl chains, linear or branched C1-C6 alkyl chains substituted by at least one fluorine atom, C3-C6 cyclic groups, the cyanomethyl group, the azidomethyl group, linear or branched C1-C4 alkoxy chains, C-C4 hydroxyalkyl groups, C1-C4 alkyl methyl ester groups, C1-C4 methylcarbonylamino alkyl groups, C1-C4 methylsulfone alkyl groups, the unsubstituted phenyl group, a phenyl group substituted by one, two or three substituents chosen, independently from one another, from C1-C3 alkyl chains, trifluoromethyl, C1-3 alkoxy chains, or by a group chosen among the following groups (II-a and II-b):

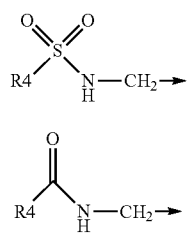

in which

R4 is a group chosen from H, linear or branched C1-C4 alkyl chains, the phenyl group, a phenyl group substituted by at least one halogen atom, a phenyl group substituted by a linear or branched C1-C4 alkyl chain, a phenyl group substituted by a linear or branched C1-C4 alkoxy chain and a phenyl group substituted by a trifluoromethyl group.

2. The compound according to claim 1, wherein T is CO and R3 is —CH$_2$SO$_2$R' wherein the radical R' is tert-butyl, methyl, isobutyl, isopentyl, or isohexyl.

3. The compound according to claim 1, wherein said compound corresponds to formula (IV):

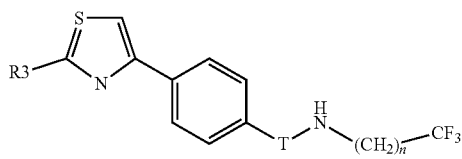

in which n, T and R3 are as defined in claim 1.

4. The compound according to claim 3, wherein T is CO and R3 is —CH$_2$SO$_2$R' wherein the radical R' is tert-butyl, methyl, isobutyl, isopentyl, or isohexyl.

5. The compound according to claim 1 chosen from the following compounds:

Compound 24: 4-(2-methylthiazol-4-yl)-N-(2,2,2-trifluoropropyl)benzene sulfonamide Compound 26: 4-(2-methylthiazol-4-yl)-N-(2,2,2-trifluoroethyl)benzene sulfonamide Compound 27: 4-(2-methylthiazol-4-yl)-N-(4,4,4-trifluorobutyl)benzene sulfonamide Compound 32: 4-(2-(cyanomethyl)thiazol-4-yl)-N-(3,3,3-trifluoropropyl)benzene sulfonamide Compound 33: 2-(4-(4-(N-(3,3,3-trifluoropropyl)sulfamoyl)phenyl)thiazol-2-yl)methyl acetate Compound 34: 2-(4-(4-(N-(3,3,3-trifluoropropyl)sulfamoyl)phenyl)thiazol-2-yl)ethyl acetate Compound 35: 2-(4-(4-(N-(3,3,3-trifluoropropyl)sulfamoyl)phenyl)thiazol-2-yl)isopropyl acetate Compound 36: N-isopropyl-2-(4-(4-(N-(3,3,3-trifluoropropyl)sulfamoyl)phenyl)thiazol-2-yl)acetamide Compound 38: 4-(2-(4-methylpentyl)thiazol-4-yl)-N-(3,3,3-trifluoropropyl)benzene sulfonamide Compound 39: 4-(2-(tert-butylsulfonylmethyl)thiazol-4-yl)-N-(3,3,3-trifluoropropyl)benzene sulfonamide Compound 43: 4-(2-methylthiazol-4-yl)-N-(3,3,3-trifluoropropyl)benzamide Compound 47: 4-(2-(4-methylpentyl)thiazol-4-yl)-N-(3,3,3-trifluoropropyl)benzamide Compound 49: 4-(2-isobutylthiazol-4-yl)-N-(3,3,3-trifluoropropyl)benzamide Compound 50: 4-(2-(tert-butylsulfonylmethyl)thiazol-4-yl)-N-(3,3,3-trifluoropropyl)benzamide Compound 51: 4-(2-(cyanomethyl)thiazol-4-yl)-N-(3,3,3-trifluoropropyl)benzamide Compound 52: 2-(4-(4-(3,3,3-trifluoropropylcarbamoyl)phenyl)thiazol-2-yl)ethyl acetate Compound 53: 2-(4-(4-(3,3,3-trifluoropropylcarbamoyl)phenyl)thiazol-2-yl)isopropyl acetate Compound 54: 4-(4-(3,3,3-trifluoropropylcarbamoyl)phenyl)thiazole-2-ethyl carboxylate Compound 55: 4-(4-(3,3,3-trifluoropropylcarbamoyl)phenyl)thiazole-2-isopropyl carboxylate Compound 56: 4-(thiazol-4-yl)-N-(3,3,3-trifluoropropyl)benzamide Compound 62: 4-(5-fluoro-2-methylthiazol-4-yl)-N-(3,3,3-trifluoropropyl)benzamide Compound 64: 4-(5-chloro-2-methylthiazol-4-yl)-N-(3,3,3-trifluoropropyl)benzamide Compound 103: 4-(2-(propylsulfonamidomethyl)thiazol-4-yl)-N-(3,3,3-trifluoropropyl)benzamide; and Compound 104: 4-(2-(phenylsulfonamidomethyl)thiazol-4-yl)-N-(3,3,3-trifluoropropyl)-benzamide.

6. A method of treatment of bacterial and mycobacterial infection comprising administering, to a patient in need thereof, an effective amount of a compound according to claim 1.

7. A method of treatment of tuberculosis, leprosy or atypical mycobacterial infection comprising administering, to a patient in need thereof, an effective amount of a compound of claim 1.

8. A method of treatment of bacterial and mycobacterial infection comprising administering, to a patient in need thereof, an effective amount of a compound according to claim 3.

9. A method of treatment of tuberculosis, leprosy or atypical mycobacterial infection comprising administering, to a patient in need thereof, an effective amount of a compound of claim 3.

* * * * *